(12) United States Patent
Narkunan et al.

(10) Patent No.: US 7,687,496 B2
(45) Date of Patent: Mar. 30, 2010

(54) C7-SUBSTITUTED CAMPTOTHECIN ANALOGS

(75) Inventors: Kesavaram Narkunan, San Antonio, TX (US); Xinghai Chen, San Antonio, TX (US); Harry Kochat, San Antonio, TX (US); Frederick Hausheer, Boerne, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 2 days.

(21) Appl. No.: 11/974,754

(22) Filed: Oct. 16, 2007

(65) Prior Publication Data

US 2009/0099224 A1    Apr. 16, 2009

(51) Int. Cl.
*A61K 31/4375* (2006.01)
*A61P 35/00* (2006.01)
*C07F 7/10* (2006.01)

(52) U.S. Cl. .................. 514/233.2; 514/283; 544/69; 546/14

(58) Field of Classification Search ............ 546/14; 544/59; 514/233.2, 283
See application file for complete search history.

(56) References Cited

U.S. PATENT DOCUMENTS

| 5,726,181 | A | 3/1998 | Hausheer et al. |
| 5,910,491 | A | 6/1999 | Hausheer et al. |
| 6,194,579 | B1 | 2/2001 | Hausheer |

FOREIGN PATENT DOCUMENTS

WO    WO 02/062340    *    8/2002

OTHER PUBLICATIONS

Remington's Pharmaceuticals Sciences, pp. 420-425, 1980.*
U.S. Appl. No. 10/627,444.

* cited by examiner

*Primary Examiner*—Brandon J Fetterolf
*Assistant Examiner*—Anna Pagonakis
(74) *Attorney, Agent, or Firm*—Scott A. Whitaker, J.D.

(57) ABSTRACT

The novel C7-modified camptothecin analogs, and pharmaceutically-acceptable salts thereof, of the present invention: (i) possess potent antitumor activity (i.e., in nanomolar or subnanomolar concentrations) for inhibiting the growth of human and animal tumor cells in vitro; (ii) are potent inhibition of Topoisomerase I; (iii) lack of susceptibility to MDR/MRP drug resistance; (iv) require no metabolic drug activation: (v) lack glucuronidation of the A-ring or B-ring; (vi) reduce drug-binding affinity to plasma proteins; (vii) maintain lactone stability; (viii) maintain drug potency; and (ix) possess a low molecular weight (e.g., MW<600).

6 Claims, No Drawings

C7-SUBSTITUTED CAMPTOTHECIN ANALOGS

FIELD OF THE INVENTION

The present invention relates to novel analogs of camptothecin. More specifically, the present invention relates to camptothecin analogs, and pharmaceutically-acceptable salts thereof, wherein various types of covalent linkages will connect one of the a silicon or germanium-containing side chains to the C7 position on the B-ring of, e.g., Karenitecin®.

BACKGROUND OF THE INVENTION

I. Camptothecin (CPT)

Camptothecin (CPT; IUPAC Nomenclature: (S)-4-Ethyl-4-hydroxy-1H-pyrano[3',4':6,7]indolizino[1,2-b]quinoline-3,14(4H,12H)-dione) and certain of its analogs have been shown to possess varying degrees of anti-neoplastic activity. Presently, two CPT analogs (Irinotecan™ and Topotecan™, as discussed below) have been approved for therapeutic use in the United States by the Food and Drug Administration (FDA) for various forms of solid neoplasms.

CPT was initially isolated in 1966 by Wall, et al., from *Camptotheca accuminata*, (Nyssaceae family) a Chinese yew. See, Wall, M. E., et al., Plant chemotherapeutic agents. I. The Isolation and Structure of Camptothecin, a Novel Alkaloidal Leukemia and Tumor Inhibitor from *Camptotheca Acuminata. J. Am. Chem. Soc.* 88:3888-3890 (1966)).

The structure of this originally isolated camptothecin (CPT) is shown below:

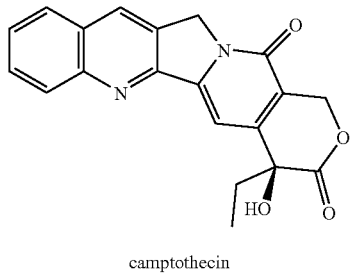

camptothecin

The pentacyclic ring system includes a pyztolo[3,4-b] quinoline (rings A, B and C), a conjugated pyridone ring D), and six membered lactone (ring E) with an 20-hydroxyl group. By the early 1970's, CPT had reached Phase I and Phase II clinical trials and although it was found to possess anti-tumor activity, there were numerous deleterious physiological side-effects associated with its use. The side-effects included, but were not limited to, severe and unpredictable myelosuppression, gastrointestinal toxicity, hemorrhagic cystitis, alopecia, diarrhea, nausea, vomiting and the like. These toxicities, found during early clinical studies, rendered the drug "unmanageable" during this time period. See, Muggia, F. M.; et al., Phase I Clinical Trial of Weekly and Daily Treatment With Camptothecin (NSC-100880): Correlation With Preclinical Studies. *Cancer Chemother. Rep.* 56:515-521 (1972); Schaeppi, U., et al., Toxicity of Camptothecin (NSC-100880). *Cancer Chemother. Rep.* 5:25-36 (1974).

In order to demonstrate both the utility and novelty of the present invention, it will be instructive to engage in brief review of the published literature dealing with human clinical trials conducted with administered in a parenteral manner.

Physicochemical studies of CPT found that the closed E-ring lactone form of CPT possessed extremely poor solubility in water (i.e., approximately 0.1 µg of drug dissolving in 1 mL of water). In addition, of the two CPT enantiomers, the naturally occurring (S)-isomer was found to be more potent than the (R)-isomer. See, e.g., Motwani, M. V., et al., Flavopiridol (Flavo) Potentiates the SN-38-Induced Apoptosis in Association with Downregulation of Cyclin Dependent Kinase Inhibitor p21waf1/cip1 in HCT116 Cells. *Proc. Am. Assoc. Cancer Res.* 41:32-43 (2000). These different properties of the various analogs are caused by the different chemical substituents on the core structure of CPT.

Thus, because of its extremely poor water solubility, in order for CPT to be administered in human clinical trials, it was initially formulated using sodium hydroxide. It is important to note, that all of these early clinical studies used sodium hydroxide formulations of CPT in order to markedly increase the water solubility (i.e., hydrophilicity) of the molecule to allow sufficient quantities of the agent to be administered parenterally to patients. The sodium hydroxide formulation of CPT created more water soluble CPT species that permitted clinicians to administer larger concentrations of CPT with smaller medication volumes of administration, thereby allowing sufficiently higher doses of the drug to be administered to cancer subjects undergoing Phase I and Phase II clinical trials. However, it was subsequently established that this formulation resulted in hydrolysis of the lactone E-ring of the camptothecin molecule, thus forming the water soluble carboxylate form of CPT which only possessed approximately one-tenth or less of the anti-tumor potency of the original, non-hydrolyzed lactone form of CPT. The clinical trials performed using the sodium hydroxide-formulated CPT provide to be highly disappointing, due to both the frequently-observed significant systemic toxicities and the lack of anti-neoplastic activity. It was subsequently ascertained that the drug's relative low hydrophilicity, was the most important reason for these side-effects. This low aqueous solubility of CPT in the lactone form greatly limited the practical clinical utility of the drug because prohibitively large volumes of fluid had to be administered to the subject in order to provide an effective dose of the drug. Because of the potent anti-neoplastic activity and poor water solubility of CPT lactone forms and many of its analogs in water, a great deal of effort was directed at generating new CPT lactone analogs that possessed greater aqueous solubility. Water soluble CPT analogs should not exist in large amounts in the open E-ring form but, alternately, should predominantly remain in the closed-ring lactone form, in order to be active. Thus, CPT analogs where equilibrium favors the closed-ring lactone form are desirable for administration.

II. Pharmacological Activity of CPT

Despite these earlier disappointing side-effects, increasing clinical interest in CPT was evoked during the 1980s, as a result of the revelation of its mechanism of action (i.e., Topoisomerase I inhibition). This new information regarding the mechanism of action of CPT analogs served to rekindle the interest in developing new Topoisomerase I inhibitors for use as anti-neoplastic drugs and subsequently several research groups began attempting to develop new CPT analogs for cancer therapy. See, Hsiang, Y. H., et al., Camptothecin Induces Protein-Linked DNA Breaks Via Mammalian DNA Topoisomerase I. *J. Biol. Chem.* 260:14873-14878 (1985); Hsiang, Y. H.; Liu, L. F., Identification of Mammalian DNA Topoisomerase I as an Intracellular Target of the Anticancer Drug Camptothecin. *Cancer Res.* 48:1722-1726 (1988);

Hsiang, Y. H., et al., Arrest of Replication Forks by Drug-Stabilized Topoisomerase I DNA Cleavable Complexes as a Mechanism of Cell Killing by Camptothecin. *Cancer Res.* 49:5077-5082 (1989).

Several clinically important anticancer drugs kill tumor cells by affecting DNA Topoisomerases. Topoisomerases are essential nuclear enzymes that function in DNA replication and tertiary structural modifications (e.g., overwinding, underwinding, and catenation) which normally arise during replication, transcription, and perhaps other DNA processes. Two major Topoisomerases that are ubiquitous to all eukaryotic cells: (i) Topoisomerase I (Topo I) which cleaves single stranded DNA and (ii) Topoisomerase II (Topo II) which cleaves double stranded DNA. Topoisomerase I is involved in DNA replication; it relieves the torsional strain introduced ahead of the moving replication fork.

Topoisomerase I (Topo I) is a monomeric 100 kDal polypeptide containing 765 amino acids, and is encoded by a gene located on chromosome 20q12-13.2. See, e.g., Creemers, G. J., et al., Topoisomerase I Inhibitors: Topotecan and Irinotecan. *Cancer Treat. Rev.* 20:73-96 (1994); Takimoto, C. H.; Arbuck, S. G. The Camptothecins. *Cancer Chemother and Biother. 2nd edition* (B. L. Chabner, D. L. Longo (eds)), 463-384 (1996). It is an essential enzyme in DNA replication and RNA transcription, and is present in all eukaryotic (including tumor) cells. Since normal DNA is super-coiled, and tightly fitted in the chromosomes, the DNA-replication fork is unable to synthesize new DNA out of this topological con-strained DNA. Topo I acts in an ATP-independent fashion, by binding to super-coiled DNA and cleaving a phosphodiester bond, resulting in a single-strand break. At the same time, Topo I forms a covalent reversible adduct between a tyrosine residue at position 723 of Topo I and the 3' end of the single-strand DNA molecule, called the cleavable complex. The DNA molecule is able to rotate freely around the intact single DNA strand, and relaxation of the DNA occurs. After the religation of the cleavage, Topo I dissociates from the DNA. The cleavable complex usually is present for only a short time, just to allow the single uncleaved DNA strand to unwind.

Specifically, it was found that CPT forms a reversible complex comprising: Topo I-CPT-DNA. In brief, the primary mechanism of action of CPT is the inhibition of Topo I by blocking the rejoining step of the cleavage/relegation reaction of Topo I, thus resulting in the accumulation of covalent reaction intermediates (i.e., the cleavable complex). CPT-based cellular apoptosis is S-phase-specific killing through potentially lethal collisions between advancing replication forks and Topo I DNA complexes. Two repair responses to Topo I-mediated DNA damage involving covalent modification of Topo I have been identified. The first involves activation of the Ubiquitin/26S proteasome pathway, leading to degradation of Topo I (CPT-induced Topo I down-regulation). The second involves the Small Ubiquitin-like Modifier (SUMO) conjugation to Topo I. These repair mechanisms for Topo I-mediated DNA damage play an important role in determining CPT sensitivity and resistance in tumor cells.

Topo I purified from human colon carcinoma cells or calf thymus has been shown to be inhibited by CPT. CPT, Irino-tecan™ (CPT-11) and an additional Topo I inhibitor, Topote-can, has been in used in clinical trials to treat certain types of human cancer. For the purpose of this invention, CPT analogs include: 7-ethyl-10-[4-(1-piperidino)-1-piperidino]carbony-loxy camptothecin (Irinotecan™ or CPT-11), 10-hydroxy-7-ethyl camptothecin (HECPT), 9-aminocamptothecin, 10,11 methylenedioxy camptothecin and 9-dimethylaminomethyl-10-hydroxy camptothecin (Topotecan). These CPT analogs use the same mechanism to inhibit Topo I; they stabilize the covalent complex of enzyme and strand-cleaved DNA, which is an intermediate in the catalytic mechanism. These analogs have no binding affinity for either isolated DNA or Topo I but do bind with measurable affinity to the enzyme-DNA complex. The stabilization of the Topo I "cleavable complex" by CPT and analogs is readily reversible.

Topoisomerase II (Topo II) works in a similar way to Topo I, with the difference being that the former enzyme acts ATP-dependently, to cause reversible doublestrand DNA cleavage, in the relaxation of DNA. Direct interference of CPTs with Topo II has not been described. However, it has been reported that Irinotecan™ (CPT-11) treatment sensitizes some tumor-xenografts in mice to Topo II inhibitors, by increasing the Topo II mRNA expression after 24 and 48 hours. This suggests that combination therapies with Topo I and Topo II targeting chemotherapy for human solid tumors might be valuable. The CPT analogs inhibit the religation reaction of Topo I by selectively inducing a stabilization of the cleavable complexes at Topo I sites bearing a guanine residue at the 5'-terminus of the enzyme mediated breaks. See, e.g., Sve-jstrup, J. Q., et al., Technique for Uncoupling the Cleavage and Religation Reactions of Eukaryotic Topoisomerase I. The Mode of Action of Camptothecin at a Specific Recognition Site. *J. Mol. Biol.* 222:669-678 (1991); Jaxel, C., et al., Effect of Local DNA Sequence on Topoisomerase I Cleavage in the Presence or Absence of Camptothecin. *J. Biol. Chem.* 266: 20418-20423 (1991); Tanizawa, A., et al., Induction of Cleavage in Topoisomerase I c-DNA by Topoisomerase I Enzymes From Calf Thymus and Wheat Germ in the Presence and Absence of Camptothecin. *Nucl. Acids Res.* 21:5157-5166 (1994). Although this stabilization in itself is reversible, an irreversible doublestrand break occurs when a replication fork meets a cleavable complex. The higher the levels of Topo I, the higher the frequency of cleavable complexes, and the higher the number of DNA breaks. These breaks may lead to cell cycle arrest in the S/G2-phase, activation of apoptosis pathways, and finally to cell death. See, e.g., Hsiang, Y. H., et al., Arrest of Replication Forks by Drug-Stabilized Topoi-somerase I DNA Cleavable Complexes as a Mechanism of Cell Killing by Camptothecin. *Cancer Res.* 49:5077-5082 (1989). As a result of this, Topo I inhibitors are only lethal in the presence of ongoing DNA replication or RNA transcription. See, e.g., D'Arpa, P., et al., Involvement of Nucleic Acid Synthesis in Cell Killing Mechanisms of Topoisomerase I Poisons. *Cancer Res.* 50:6919-6924 (1990). S-phase synchronized cells appeared to be much more sensitive to Topo I inhibitors, compared to G1- or G2/M-cells, suggesting an S-phase specific cytotoxicity for this type of drugs. See, e.g., Takimoto, C. H., et al., Phase I and Pharmacologic Study of Irinotecan Administered as a 96-Hour Infusion Weekly to Adult Cancer Patients. *J. Clin. Oncol.* 18:659-667 (2000). In colon, prostate, ovary and esophagus tumors, elevated Topo I levels have been found, whereas in kidney tumors and non-Hodgkin lymphomas this was not the case See, e.g., Van der Zee, A., et al., P-glycoprotein Expression and DNA Topoi-somerase I and II Activity in Benign Tumors of the Ovary and in Malignant Tumors of the Ovary, Before and After Plati-num/Cyclophosphamide Chemotherapy. *Cancer Res.* 51: 5915-5920 (1991). Recent investigations have indicated that Irinotecan™ and Topotecan™ are also inhibitors of angio-genesis, a property that might contribute to their chemotherapeutic activity. Neovascularization has been positively correlated with increasing invasion and metastases of various human tumors. In mice cornea models, anti-angiogenic effects of some CPTs, including Irinotecan™ (CPT-11), were studied. Angiogenesis was induced by fibroblast growth factor, but by increasing the dose of Irinotecan™, the area of angiogenesis in the tumor decreased, following a negative, almost exponential, curve. At dose levels of 210 mg/kg a significant reduction of neovascularization was observed.

Although CPT and the aforementioned CPT analogs have no discernable direct effects on Topo II, these CPT analogs are believed to stabilize the Topo I "cleavable complex" in a manner analogous to the way in which epipodophyllotoxin glycosides and various anthracyclines inhibit Topo II.

Inhibition of Topo I by CPT and analogs induces protein-associated-DNA single-strand breaks. Virtually all of the DNA strand breaks observed in vitro cells treated with CPT are protein linked. However, an increase in unexplained protein-free breaks can be detected in L1210 cells treated with CPT. The analogs appear to produce identical DNA cleavage patterns in end-labeled linear DNA. It has not been demonstrated that CPT or CPT analogs cleaves DNA in the absence of the Topo I enzyme.

III. Cell Cycle-Specific Activity of Camptothecin

The activity of CPT is cell cycle-specific. The greatest quantitative biochemical effect observed in cells exposed to CPT is DNA single-strand breaks that occur during the S-phase. Because the S-phase is a relatively short phase of the cell cycle, longer exposure to the drugs results in increased cell killing. Brief exposure of tumor cells to the drugs produces little or no cell killing, and quiescent cells are refractory. These aforementioned results are likely due to two factors:

(i) This class of drugs inhibit the normal activity of Topo I, reversibly. Although they may produce potentially lethal modifications of the DNA structure during DNA replication, the DNA strand breaks may be repaired after washout of the drug; and (ii) Cells treated with Topo I inhibitors, such as CPT tend to stay in $G_0$ of the cell cycle until the drug is removed and the cleaved DNA is repaired. Inhibitors of these enzymes can affect many aspects of cell metabolism including replication, transcription, recombination, and chromosomal segregation.

IV. Previously-Tested Camptothecin Analogs

As discussed above, CPT and many of its analogs (see e.g., Wall and Wani, Camptothecin and Taxol: Discovery to Clinic-Thirteenth Bruce F. Cain Memorial Award Lecture *Cancer Research* 55:753-760 (1995)) are poorly water soluble and are reportedly also poorly soluble in a number of pharmaceutically-acceptable organic solvents as well. However, there are numerous reports of newly created water soluble analogs of CPT (Sawada, S., et al., Synthesis and Antitumor Activity of Novel Water Soluble Analogs of Camptothecin as Specific Inhibitors of Topoisomerase I. *Jour. Med. Chem.* 38:395-401 (1995)) which have been synthesized in an attempt to overcome some of the significant technical problems in drug administration of poorly water soluble camptothecins to subjects with cancer. Several water soluble CPT analogs have been synthesized in an attempt to address the poor water solubility and difficulties in administration to subjects. Several examples of these water soluble CPT analogs are set forth below in Table I:

TABLE I 9-dimethylaminomethyl-10-hydroxycamptothecin (Topotecan ™)
7-[(4-methylpiperazino)methyl]-10,11-ethylenedioxycamptothecin
7-[(4-methylpiperazino)methyl]-10,11-methylenedioxycamptothecin
7-ethyl-10-[4-(1-piperidino)-1-piperidino]carbonyloxycamptothecin (Irinotecan ™ or CPT-11)
9-nitrocamptothecin (Rubitecan)

Other substituted CPT analogs with different solubility and pharmacologic properties have been synthesized as well; examples of these camptothecin analogs include 9-aminocamptothecin and 9-nitrocamptothecin (Rubitecan) that are poorly soluble in both aqueous and non-aqueous media and have been tested in humans. Rubitecan (9-nitrocamptothecin) is a prodrug of 9-aminocamptothecin, and has been shown to spontaneously convert to 9-aminocamptothecin in aqueous media and in vivo in mice, dogs and humans (see, Hinz, et al., Pharmacokinetics of the in vivo and in vitro Conversion of 9-Nitro-20(S)-camptothecin to 9-Amino-20 (S)-camptothecin in Humans, Dogs and Mice, *Cancer Res.* 54:3096-3100 (1994)).

The pharmacokinetic behavior of 9-nitrocamptothecin and 9-aminocamptothecin is similar to the water-soluble camptothecin analogs (i.e., Topotecan™ and Irinotecan™) in that the plasma half lives are markedly shorter than the more lipid soluble CPT analogs. An additional major problem with 9-aminocamptothecin is that its chemical synthesis using the semi-synthetic method is performed by nitration of CPT, followed by reduction to the amino group, which is a very low yield type of synthesis. 9-aminocamptothecin is also light sensitive, heat sensitive and oxygen sensitive which render both the initial synthesis and subsequent stability (i.e., shelf-life) of 9-aminocamptothecin problematic, at best. Moreover, the chemical decomposition reactions of 9-aminocamptothecin frequently result in the formation of analogs that exhibit a large degree of toxicity in nude mice, whereas pure 9-aminocamptothecin is significantly less toxic.

As previously discussed, 9-aminocamptothecin is also difficult to administer to subjects because it is poorly soluble in both aqueous and organic solvents. Alternately, while 9-nitrocamptothecin is easier to produce and is more chemically stable, the chemical conversion to 9-aminocamptothecin causes the drug is reportedly susceptible to MDR/MRP tumor-mediated drug resistance, which further limits its utility in the unfortunately common setting of drug resistant neoplasms. Based on pharmacokinetic behavior and chemical properties, 9-aminocamptothecin is predicted to have reduced tissue penetration and retention relative to more lipid soluble camptothecin analogs. Further, its poor solubility diminishes the amount of the drug that can cross the blood/brain barrier.

Of this diverse group of substituted CPT analogs undergoing human clinical development, Irinotecan™ (CPT-11) has been one of the most extensively studied in both Phase I and Phase II clinical trials in human patients with cancer. It is noteworthy that 7-ethyl-10-[4-(1-piperidino)-1-piperidino] carbonyloxy camptothecin (Irinotecan™), which is a water soluble prodrug, is biologically inactive and requires activation by a putative carboxylesterase enzyme. The active species of Irinotecan™ is the depiperidenylated 10-hydroxy-7-ethyl camptothecin (as claimed in Miyasaka, et al., U.S. Pat. No. 4,473,692, (1984)), which is also known as SN38. SN38 is a toxic lipophilic metabolite, which is formed by an in vivo bioactivation of Irinotecan™ by a putative carboxylesterase enzyme.

SN38 is very poorly soluble in water and has not been directly administered to human patients with cancer. Recently, it has been reported in human patients that SN38 undergoes further metabolism to form a glucuronide species, which is an inactive form of the drug with respect to anti-tumor activity, and also appears to be involved in producing human toxicity (e.g., diarrhea, leukopenia) and substantial interpatient variability in drug levels of the free metabolite and its glucuronide conjugate.

Irinotecan™ has been tested in human clinical trials in the United States, Europe and Japan. Clinical studies in Japan alone, have reported approximately 100 patient deaths which have been directly attributable to Irinotecan™ drug toxicity. The Miyasaka, et al. patents (U.S. Pat. No. 4,473,692 and U.S. Pat. No. 4,604,463) state that the object of their invention is to " . . . provide 10-substituted camptothecins which are strong in anti-tumor activity and possess good absorbability in living bodies with very low toxicity" and " . . . to provide new camptothecin analogs which are strong in anti-tumor activity and possess good solubility in water and an extremely low toxicity".

Having multiple drug-related human deaths and serious patient toxicity, is clearly a failure of the aforementioned 10-substituted camptothecins synthesized by Miyasaka, et al., to fulfill their stated objectives. It is notable that tremendous interpatient variability with regard to drug levels of various forms, drug metabolism, certain pharmacokinetic properties and toxicity has been reported with the use of Irinotecan™ in human subjects with cancer. Parenteral administration of Irinotecan™ can achieve micromolar plasma concentrations of Irinotecan™ that, through metabolism to form SN38, can yield nanomolar concentrations of the active metabolite SN38. It has recently been reported in human subjects that SN38 undergoes further metabolism to form the SN38 glucuronide (see, e.g., Gupta, et al., Metabolic Fate of Irinotecan in Humans: Correlation of Glucuronidation with Diarrhea. *Cancer Res.* 54:3723-3725 (1994)).

This further metabolic conversion of Irinotecan™ is important, since there is also reportedly large variability in the conversion of Irinotecan™ to SN38 and large interpatient variability in the metabolism of SN38 to form the inactive (and toxic) SN38 glucuronide conjugate in human subjects. (see, e.g., Gupta, et al., Metabolic Fate of Irinotecan in Humans: Correlation of Glucuronidation with Diarrhea. *Cancer Res.* 54:3723-3725 (1994) and Ohe, et al., Phase I Study and Pharmacokinetics of CPT-11 with 5-Day Continuous Infusion. *JNCI* 84(12):972-974 (1992)).

Since the amount of Irinotecan™ and SN38 metabolized is not predictable in individual patients, significant clinical limitations are posed and create the risk of life-threatening drug toxicity, and/or risk of drug inactivity due to five putative biological mechanisms: (i) conversion of greater amounts of Irinotecan™ to SN38; (ii) inactivation of SN38 by glucuronidation; (iii) conversion of SN38 glucuronide to free SN38; (iv) lack of anti-neoplastic activity due to the conversion of lesser amounts of Irinotecan™ to form SN38; and (v) lack of anti-neoplastic activity by more rapid and extensive conversion of SN38 to form the glucuronide species. It is important to note that even a doubling of the plasma concentration of the potent Irinotecan™ metabolite SN38 may result in significant toxicity, because free SN38 exhibits anti-neoplastic activity at nanomolar concentrations.

Another source of interpatient variability and toxicity is the in vivo de-glucuronidation of SN38 and similar CPT analogs to produce a free and active species of the drug. Deglucuronidation of a CPT analog that is susceptible to A-ring glucuronidation, such as SN38, results in an increase in the plasma or local tissue concentration of the free and active form of the drug, and if high enough levels were reached, patient toxicity, and even death may result.

In addition to the two aforementioned FDA-approved drugs, there are currently at least nine camptothecin analogs that have been evaluated in various stages of clinical testing. These camptothecin analogs include:

1. Karenitecin® (BNP1350)

Karenitecin® (BNP1350) is a highly lipophilic camptothecin analog having a 7-trimethylsilylethyl moiety and is claimed in U.S. Pat. No. 5,910,491, along with formulations and uses thereof. Formulations of Karenitecin® with N-methylpyrrolidinone (NMP) are claimed in, e.g., U.S. Pat. No. 5,726,181.

2. Lurtotecan (NX 211)

NX211 is a water-soluble camptothecin having a 10,11-ethylenedioxy moiety and a cleavable 4-methylpiperazino methyl moiety at C7. By way of example, U.S. Pat. No. 5,559,235 discloses and claims the analogs and formulations, and uses thereof.

3. Exatecan (DX-8951f)

DX-8951f is a hexacyclic camptothecin analog, having 10-methyl and 11-fluoro substitutions, and with its sixth ring fused between C7 and C9. By way of example, and not of limitation, U.S. Pat. No. 5,637,770 describes and claims the analog, and formulations and uses thereof.

4. Diflomotecan (BN 80915)

BN 80915 is a 10,11-difluorocamptothecin, with a 7-member E-ring. By way of example, and not of limitation, U.S. Pat. No. 5,981,542 describes and claims the analog, and its uses and formulations.

5. Rubitecan (9-Nitro CPT)

9-Nitrocamptothecin, as mentioned above is poorly soluble in both aqueous and organic solvents and is described and is not claimed any United States Patents, with the first publication of the analog occurring in Japanese Patent Application No. 82-160944 in 1982. Several patents have issued since then, all regarding processes for preparing the analog as well as uses thereof.

6. Afeletecan (CPT Glycoconjugate)

Afeletecan is an C20 glycoconjugated, water-soluble analog of camptothecin and is described and claimed in U.S. Pat. No. 6,492,335.

7. Gimatecan (ST1481)

ST1481 is non-water-soluble compound having a C7 imino moiety, bonded to a terminal tert-butoxy group. The analog is described and claimed in U.S. Pat. No. 6,242,457.

8. Mureletecan (PNU166148)

Mureletecan is another water-soluble prodrug having a cleavable peptide moiety bonded to C20 to form an ester.

9. Pegbetotecan, Pegcamotecan, Peglinxotecan (PEG CPT; Prothecan®)

This prodrug includes a cleavable water-soluble polyethylene glycol moiety that forms an ester at C20. By way of example, the analog is described and claimed in U.S. Pat. No. 5,840,900.

The various chemical structures of the nine aforementioned camptothecin analogs are set forth in Table II, below:

TABLE II
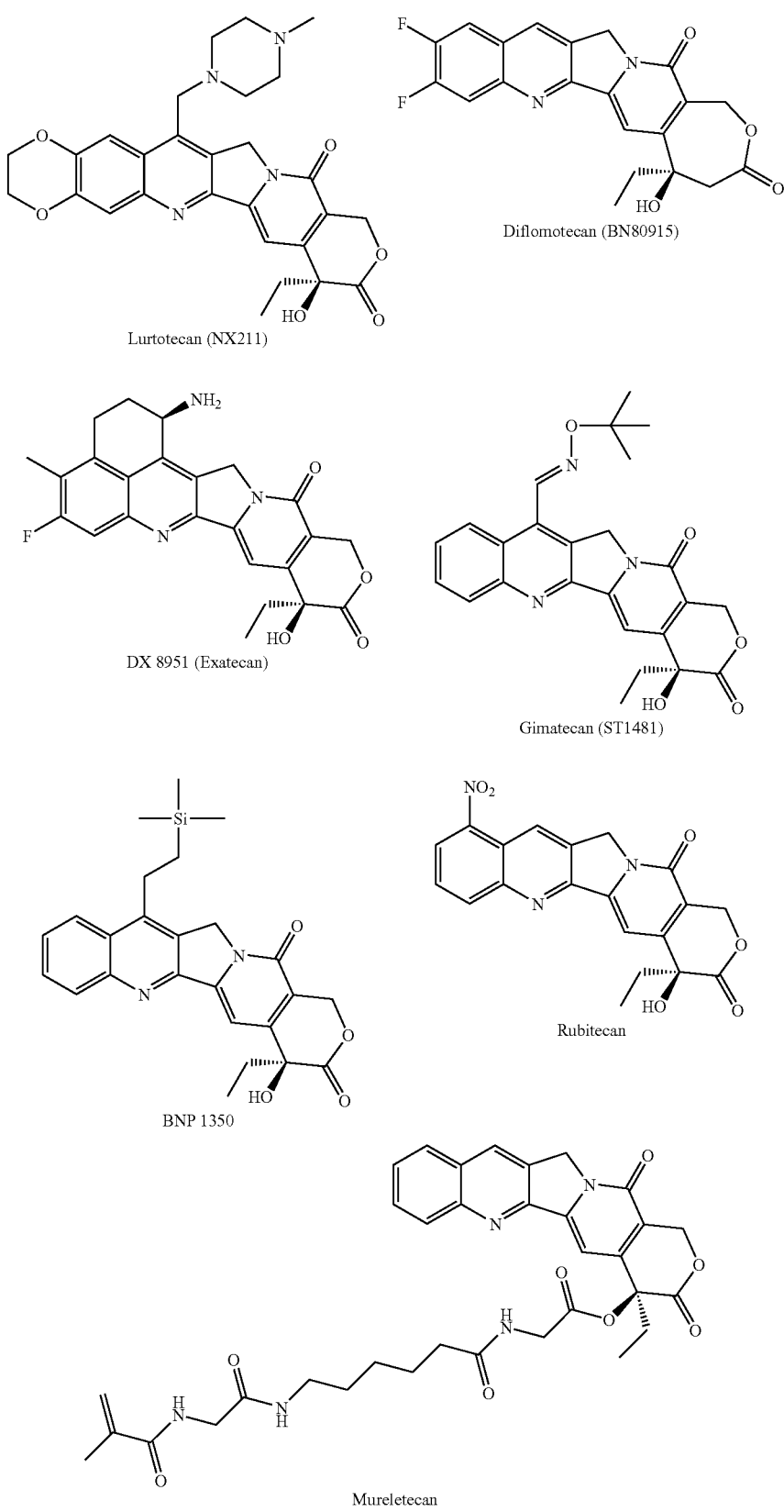

TABLE II-continued

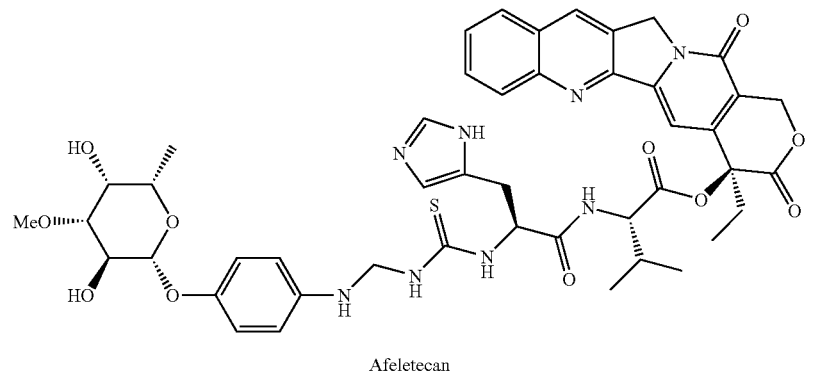

Afeletecan

Poorly water-soluble (i.e., hydrophobic) camptothecins are necessarily formulated for administration by dissolution or suspension in organic solvents. U.S. Pat. No. 5,447,936; No. 5,726,181; No. 5,859,022; No. 5,859,023; No. 5,880, 133; No. 5,900,419; No. 5,935,967; No. 5,955,467; and other describe pharmaceutical formulations of highly lipophilic, poorly water-soluble camptothecin analogs in various organic solvents, namely N,N-dimethylacetamide (DMA); N,N-dimethylisosorbide (DMI); and N-methylpyrrolidinone (NMP).

VI. Formulation and Administration of CPT and Analogs

In the early-1970's, clinical studies utilizing the sodium salt of camptothecin were begun at the Baltimore Cancer Research Center. In this clinical trial, CPT was administered as a rapidly running IV solution over a 5-10 minute period at a concentration of 2 mg of camptothecin sodium per milliliter of saline. Doses of CPT sodium from 0.5 to 10.0 mg/kg of actual or ideal body weight (whichever was less) were used. These investigators reported that because hemorrhagic sterile cystitis was noted in several of the early trials, patients receiving camptothecin sodium were well-hydrated either intravenously (i.v.) or orally for 72 hours after drug administration. It is noteworthy that the mean urine recovery of CPT was 17.4% over the first 48 hours (with the range from: 3.6% to 38.9%) with most of the excretion occurring in the initial 12 hours. When these investigators excluded the five patients with impaired excretion, the mean urine recovery of CPT was 22.8%. These investigators noted that non-metabolized camptothecin in high concentrations rapidly appeared in the urine after iv drug administration and went further to state that this finding probably accounted for the sterile hemorrhagic cystitis noted in three moderately dehydrated patients. Although maintaining a copious urine outflow seems able to prevent this complication, the investigators reported that they were exploring various alterations in urine pH as another possible way of decreasing the risk of this debilitating type of toxicity.

Muggia, et. al. (Phase I Clinical Trial of Weekly and Daily Treatment with Camptothecin (NSC-100880): Correlation with Preclinical Studies. *Cancer Chemotherapy Reports, Part 1.* 56(4):515-521 (1972)) reported results of a Phase I clinical trial in fifteen patients treated with CPT sodium at four weekly dose levels ranging from 20-67 mg/m². No clinical benefit was observed in eight patients with measurable disease who were treated with the 5-day courses at dose levels associated with toxicity. The CPT was administered in concentrations of 1 or 10 mg/mL and it was always administered by intravenous push. Cystitis was the most prominent non-hematologic toxic effect observed in this study. Bladder toxicity was dose limiting in three patients receiving doses of 20 to 30 mg/m², and occurred in two additional patients at doses of 30 and 44 mg/m². Cystitis, another toxic effect occurring frequently after treatment with camptothecin, was not predicted by preclinical toxicological studies. Clinical experience present inventors would suggest that the occurrence of cystitis may be related to the duration of the patient's exposure to the drug. It is their experience that CPT is excreted unchanged by the kidneys, although a large percentage of the drug administered cannot be accounted for in the urine. It is possible that relatively less drug is excreted in the urine of animals since an extremely active transport of CPT into bile has been demonstrated. Alternatively, one needs to postulate that the mucosa of the human bladder is more susceptible to the toxic action of CPT or that the effect on the human bladder is due to some unrecognized CPT metabolite.

In 1972, Moertel and coworkers (Phase II study of camptothecin (NSC-100880) in the treatment of advanced gastrointestinal cancer. *Cancer Chemother Rep.* 56(1):95-101 (1972)) administered CPT sodium dissolved in physiologic saline at a concentration of 2 mg/mL and administered by rapid intravenous infusion over 5-10 minutes. Two schedules of administration were used in this study: (i) a single injection repeated at 3-week intervals; and (ii) a 5-day course repeated every 4 weeks. The initial dose for the single-dose method was 180 mg/m². Because of toxic effects, which were considered excessive by the investigators, later patients were treated at doses ranging between 90 and 120 mg/m². Dosages for the 5-day course ranged between 11 and 22 mg/m²/day (total course: 55-110 mg/m²). The toxicity and response data from this aforementioned study is summarized, below, in Table III-Table VI. Diarrhea was only a problem at higher doses, although it could be quite severe to the point of fecal incontinence and could persist for as long as 4 weeks. Cystitis usually began about 7-10 days after treatment and was characterized clinically by dysuria and frequency. With more severe toxicity, gross hematuria developed. Pathologically, this was characterized by multiple necrotic ulcerations which could involve the entire urinary tract from kidney pelvis to bladder. According to these investigators, the occurrence of hemorrhagic cystitis did not preclude further treatment with CPT, and its severity could be titrated down by lowering the dose in subsequent courses. These investigators also reported that the more prolonged schedule produced more severe toxicity at a given total dose level, but the difference was not as great as might have been predicted by preclinical animal studies.

These investigators proposed that a reasonable initial dose of CPT sodium is 110-120 mg/m² for the single-injection method or 17 mg/m²/day (total dose: 85 mg/m²) for the 5-day course. They noted that after 2 months (8 or 9 weeks) only two of their 61 patients showed evidence of partial objective improvement and none showed improvement at 3 months. Both patients who demonstrated an objective response at 2 months had large bowel cancer. These investigators concluded that CPT " . . . is a drug of protean and unpredictable toxicity that has no clinical value in the management of gastrointestinal cancer."

TABLE III

Toxic Reactions: Single-Dose Method
Number of Patients with Non-Hematologic Toxicity:

| Dose (mg/m²) | No. of Patients Treated | Diarrhea | Cystitis |
|---|---|---|---|
| 90 | 10 | | |
| 100 | 6 | | 2 |
| 110 | 2 | 1 | 1 |
| 120 | 7 | 4 | 2 |
| 180 | 9 | 2 | 3 |

TABLE IV

Toxic Reactions: 5-day Course
Non-Hematologic Toxicity No. of Patients With:

| Dose (mg/m² × 5) | No. of Patients Treated | Diarrhea | Cystitis |
|---|---|---|---|
| 11 | 2 | | 1 |
| 15 | 9 | 1 | 4 |
| 17 | 5 | 4 | 2 |
| 20 | 10 | 4 | 6 |
| 22 | 1 | 1 | |

TABLE V

Relationship of Method of Administration to Cystitis

| | Method of Administration | |
|---|---|---|
| Cystitis | Single Dose (% of 34 Patients) | 5-Day Course (% of 27 Patients) |
| | 24 | 48 (P < 0.05) |

TABLE VI

Objective Results
Single-Dose Method (34 Patients Total)

| | Time after start of therapy | | | |
|---|---|---|---|---|
| Objective Results* | 3 wks | 6 wks | 9 wks | 12 wks |
| Improved | 4 | 2 | 2 | — |
| Stable | 17 | 11 | 8 | 6 |
| Worse | 13 | 21 | 24 | 28 |

TABLE VI-continued

Objective Results
5-Day Course (27 Patients Total)

| | Time after start of therapy | | |
|---|---|---|---|
| Objective results* | 4 wks | 8 wks | 12 wks |
| Improved | 1 | — | — |
| Stable | 12 | 7 | 6 |
| Worse | 14 | 20 | 21 |

*A total of 3 patients showed a 25%-50% response at 3 wks, only.

In another study, Gottlieb and Luce (Treatment of Malignant Melanoma with Camptothecin (NSC-100880) *Cancer Chemotherapy Reports, Part* 1 56(1): 103-105 (1972)) reported the results of treatment of patients with malignant melanoma with CPT sodium (1972). Fifteen patients with advanced malignant melanoma were treated with CPT at doses of 90-360 mg/m² repeated every 2 weeks. CPT-sodium was administered as a single rapid intravenous (IV) injection starting at a dose of 120 mg/m² repeated at 2-week intervals. The dose in subsequent courses was increased by increments of 60 mg/m² per dose (to a maximum of 360 mg/m²) in eight patients who tolerated their initial doses with minimal toxicity. To prevent the known bladder toxicity of this drug, patients were well hydrated for 3 days after therapy. None of the patients had a 50% or greater decrease in tumor diameter. Less pronounced transient tumor regression was noted in three patients, but no clinical benefit was associated with these responses. The remaining patients had no change or progression in their disease. Toxic effects included myelosuppression (11 patients), nausea and vomiting, alopecia, diarrhea, and hemorrhagic cystitis. These investigators concluded that CPT, at least as administered in this study, had little to offer the patient with advanced disseminated melanoma.

Creaven, et al., (Plasma Camptothecin (NSC-100880) Levels During a 5-Day Course of Treatment: Relation to Dose and Toxicity. *Cancer Chemotherapy Reports Part* 1 56(5): 573-578 (1979)) reported studies of plasma CPT levels during a 5-day course of treatment. These investigators state that the toxicity of CPT has been widely and unpredictably variable in the course of initial clinical evaluation. Severe toxic effects occurred even though patients with obvious renal disease were excluded. In this study they investigated plasma CPT levels 24 hours after the administration of sodium CPT administered on a once daily over a 5 day total schedule to determine whether such measurements would be of value in predicting toxicity, and observed that plasma CPT levels have little relation to the dose given when the dose is in the range of 6.5-20 mg/m²/day.

There are several features which establish a commonality with these aforementioned studies with those utilizing sodium CPT. First, is the use of sodium-CPT which made the CPT more water soluble by hydrolysis of lactone E ring to form the carboxylate species (i.e., by formulating CPT in sodium hydroxide). The anti-tumor activity of the carboxylate form of CPT is reduced by at least 10-fold, which partially accounts for the lack of clinical response in these studies. Second, is the rapid intravenous administration of the drug. CPT is an S-phase specific drug and therefore will exert a greater chemotherapeutic effect under conditions of prolonged exposure, as in a continuous intravenous infusion. The short infusion (i.v. "push" or rapid i.v. infusion) times in all of these studies do not allow a long enough exposure time to the drug at suitable levels, and is further compounded by the administration of the water soluble carboxylate form of CPT. A third common feature is the notable frequency of cystitis in these studies using sodium CPT.

SUMMARY OF THE INVENTION

There remains a need for camptothecin analogs which, for example, (i) are highly lipophilic; (ii) possess substantial lactone stability; (iii) possess a long plasma half-life; (iv) reduce drug-binding affinity to plasma proteins; (v) increase the amount of free drug in human plasma which will improve the drug's bioavailability of the parent compound; (vi) augment intracellular drug uptake; and (vii) decrease to formation of glucuronide species (glucuronidation), which is an inactive form of the drug with respect to anti-tumor activity.

The camptothecin analogs, and pharmaceutically-acceptable salts thereof, disclosed and claimed in the present invention represent a novel class of chemotherapeutic compounds that have exhibited potent chemotherapeutic activity against various types of cancer. While the analogs disclosed in the instant invention possess Topoisomerase I inhibitory activity similar to that of other camptothecin derivatives, they also possess novel structural modifications rationally designed for superior bioavailability and tissue penetration, while concomitantly avoiding untoward metabolism and drug resistance mechanisms which are common in human and other mammalian cancers.

The present invention discloses analogs of the anti-tumor agent camptothecin wherein various types of covalent linkages will connect one of substituent groups to the silicon-containing side chain bound to the C7 position on the B-ring of, e.g., Karenitecin®. However, it should be noted that the silicon of Karenitecin® may also be substituted with germanium. These analogs are amphipathic and exploit the polar side chains to decrease protein binding and to augment intracellular uptake and tissue retention. The polar group on the side chain of these camptothecin analogs will reduce drug-binding affinity to plasma proteins, so as to improve plasma protein binding properties while concomitantly maintaining both lactone stability and drug potency. The increased free (i.e., non-plasma protein bound) drug in human plasma will improve the bioavailability of the parent compound. Moreover, as previously discussed, the hydrolysis of the lactone E-ring of the camptothecin molecule (thus forming the water soluble carboxylate form) only possesses approximately one-tenth or less of the anti-tumor potency of the original, non-hydrolyzed closed lactone E-ring form of the camptothecin molecule.

The analogs of the present invention have significant utility as highly efficacious chemotherapeutic drugs, and are significantly less toxic than previously disclosed camptothecin derivatives. The novel analogs may also not undergo A-ring or B-ring glucuronidation (and implicitly deglucuronidation); nor prodrugs requiring metabolic activation. Furthermore, the lack of glucuronidation decreases deleterious physiological side-effects (e.g., diarrhea, leukopenia) and may also mitigate substantial interpatient variability in drug levels of the free metabolite and its glucuronide conjugate.

Thus, in summation, many of the novel camptothecin analogs, and pharmaceutically-acceptable salts thereof, of the present invention: (i) possess potent antitumor activity (i.e., in nanomolar or subnanomolar concentrations) in inhibiting the growth of human and animal tumor cells in vitro; (ii) are potent inhibition of Topoisomerase I; (iii) lack of susceptibility to MDR/MRP drug resistance; (iv) require no metabolic drug activation: (v) lack glucuronidation of A-ring or B-ring; and (vi) possess a low molecular weight (e.g., MW<600).

The C7 position of the B-ring is one of the preferred sites of chemical modification using novel chemical substituent groups which impart useful pharmacological, biological and chemical properties to these new compositions of matter.

It is an object of the present invention to provide fascile and extremely efficient synthetic methodologies for the preparation of novel C7-substituted camptothecins analogs.

Another object is to provide new and useful camptothecin analogs which are highly efficacious as anti-cancer agents.

Other objects will become apparent from a reading of the following Specification and Claims.

DETAILED DESCRIPTION OF THE INVENTION

Definitions

"Scaffold" means the fixed structural part of the molecule of the formula given.

"Fragments", "Moieties" or "Substituent Groups" are the variable parts of the molecule, designated in the formula by variable symbols, such as $R_x$, X or other symbols. Fragments may consist of one or more of the following:

"$C_x$-$C_y$ alkyl" generally means a straight or branched-chain aliphatic hydrocarbon containing as few as x and as many as y carbon atoms. Examples include "$C_1$-$C_6$ alkyl" (also referred to as "lower alkyl"), which includes a straight or branched chain hydrocarbon with no more than 6 total carbon atoms, and $C_1$-$C_{16}$ alkyl, which includes a hydrocarbon with as few as one up to as many as sixteen total carbon atoms, and the like. In the present application, the term "alkyl" is defined as comprising a straight or branched chain hydrocarbon of between 1 and 20 atoms, which can be saturated or unsaturated, and may include heteroatoms such as nitrogen, sulfur, and oxygen;

"$C_x$-$C_y$ alkylene" means a bridging moiety formed of as few as "x" and as many as "y" —$CH_2$— groups. In the present invention, the term "alkylene" is defined as comprising a bridging hydrocarbon having from 1 to 6 total carbon atoms which is bonded at its terminal carbons to two other atoms (—$CH_2$—)$_x$ where x is 1 to 6;

"$C_x$-$C_y$ alkenyl or alkynyl" means a straight or branched chain hydrocarbon with at least one double bond (alkenyl) or triple bond (alkynyl) between two of the carbon atoms;

"$C_x$-$C_y$ alkoxy" means a straight or branched hydrocarbon chain with as few as x and as many as y carbon atoms, with the chain bonded to the scaffold through an oxygen atom;

"Alkoxycarbonyl" (aryloxycarbonyl) means an alkoxy (aryloxy) moiety bonded to the scaffold through a carbonyl;

"Halogen" or "Halo" means chloro, fluoro, bromo or iodo;

"Acyl" means —C(O)—R, where R is hydrogen, $C_x$-$C_y$ alkyl, aryl, $C_x$-$C_y$ alkenyl, $C_x$-$C_y$ alkynyl, and the like;

"Acyloxy" means —O—C(O)—R, where R is hydrogen, $C_x$-$C_y$ alkyl, aryl, and the like;

"$C_x$-$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Aryl" generally means an aromatic ring or ring system consisting of one or more rings, preferably one to three rings, fused or unfused, with the ring atoms consisting entirely of carbon atoms. In the present invention, the term "aryl" is defined as comprising as an aromatic ring system, either fused or unfused, preferably from one to three total rings, with the ring elements consisting entirely of 5-8 carbon atoms;

"Arylalkyl" means an aryl moiety as defined above, bonded to the scaffold through an alkyl moiety (the attachment chain);

"Arylalkenyl" and "Arylalkynyl" mean the same as "Arylalkyl", but including one or more double or triple bonds in the attachment chain;

"Amine" means a class of organic analogs of nitrogen that may be considered as derived from ammonia ($NH_3$) by replacing one or more of the hydrogen atoms with alkyl groups. The amine is primary, secondary or tertiary, depending upon whether one, two or three of the hydrogen atoms are replaced. A "short chain amine" is one in which the alkyl group contain from 1 to 10 carbon atoms;

"Amine" means a coordination analog formed by the union of ammonia with a metallic substance in such a way that the nitrogen atoms are linked directly to the metal. It should be noted the difference from amines, in which the nitrogen is attached directly to the carbon atom;

"Amphipathic" means a molecule possessing a polar, water-soluble group covalently bound to a nonpolar, non-water-soluble hydrocarbon chain.

"Azide" means any group of analogs having the characteristic formula $R(N_3)x$. R may be almost any metal atom, a hydrogen atom, a halogen atom, the ammonium radical, a complex $[Co(NH_3)_6]$, $[Hg(CN)_2M]$ (with M=Cu, Zn, Co, Ni), an organic radical like methyl, phenyl, nitrophenol, dinitrophenol, p-nitrobenzyl, ethyl nitrate, and the like. The azide group possesses a chain structure rather than a ring structure;

"Imine" means a class of nitrogen-containing analogs possessing a carbon-to-nitrogen double bond (i.e., R—CH=NH); and "Heterocycle" means a cyclic moiety of one or more rings, preferably one to three rings, fused or unfused, wherein at least one atom of one of the rings is a non-carbon atom. Preferred heteroatoms include oxygen, nitrogen and sulfur, or any combination of two or more of those atoms. The term "Heterocycle" includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

"Substituted" modifies the identified fragments (moieties) by replacing any, some or all of the hydrogen atoms with a moiety (moieties) as identified in the specification. Substitutions for hydrogen atoms to form substituted analogs include halo, alkyl, nitro, amino (also N-substituted, and N,N di-substituted amino), sulfonyl, hydroxy, alkoxy, phenyl, phenoxy, benzyl, benzoxy, benzoyl, and trifluoromethyl.

The term "Highly Lipophilic Camptothecin Derivatives (HLCDs)", as utilized herein, are defined as camptothecin analogs having a water solubility of less than 5 μg/mL of water.

The terms, "camptothecin analogs" or "Karenitecin® analogs", as utilized herein, refer to camptothecin analogs wherein various types of covalent linkages will connect the substituent group to a silicon or germanium-containing side-chain (bound to C7 on the B-ring) at either the 9, 10, or 11 position of said camptothecin analog or Karenitecin® analog, as well as pharmaceutically-acceptable salts, prodrugs, conjugates, hydrates, solvates, polymorphs, and/or tautomeric forms thereof. The silicon atom may also be replaced by germanium.

As utilized herein, the term "pharmaceutically acceptable carriers" refers to carriers useful with the compounds described herein, and are conventional. See, e.g., *Remington's Pharmaceutical Sciences*, by E. W. Martin, Mack Publishing Co., Easton, Pa., 15th Edition (1975), which describes compositions and formulations suitable for pharmaceutical delivery. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As utilized herein, the term "pharmaceutically acceptable salts" includes salts of the active compounds of the present invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included, are salts of amino acids such as arginate and the like, and salts of organic acids like glucuronic or galacturonic acids and the like (see, e.g., Berge, et al., Pharmaceutical Salts. *J. Pharm. Sci.* 66:1-19 (1997)). Certain specific compounds of the present invention contain both basic and acidic functionalities that allow the compounds to be converted into either base or acid addition salts.

As utilized herein the term "cancer" refers to all known forms of cancer including, solid forms of cancer (e.g., tumors), lymphomas, and leukemias.

As used herein "anti-neoplastic agent" or "anti-cancer" or "chemotherapeutic agent" or "chemotherapy agent" refer to an agent that reduces, prevents, mitigates, limits, and/or delays the deleterious physiological manifestations, the growth or metastases of neoplasms, or by killing neoplastic cells directly by necrosis or apoptosis of neoplasms or any other mechanism. Chemotherapeutic agents include, for example, fluoropyrimidine; pyrimidine nucleosides; purine nucleosides; anti-folates, platinum analogs; anthracycline/anthracenedione; epipodopodophyllotoxin; camptothecin; hormones; hormonal analogs; antihormonals; enzymes, proteins, and antibodies; vinca alkaloids; taxanes; antimicrotubule agents; alkylating agents; antimetabolites; topoisomerase inhibitors; antivirals; and miscellaneous cytostatic agents. "Chemotherapy" refers to treatments using recognized chemotherapeutic agents or chemotherapy agents.

As used herein, an "effective amount" or a "pharmaceutically-effective amount" in reference to the compounds or compositions of the instant invention refers to the amount sufficient to induce a desired biological, pharmacological, or therapeutic outcome in a subject with neoplastic disease. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In the present invention, the result will generally include the reduction, prevention, mitigation, delay in the onset of, attenuation of the severity of, and/or a hastening in the resolution of, or reversal of chemotherapy-associated toxicity; an increase in the frequency and/or number of treatments; and/or an increase in duration of chemotherapeutic therapy.

As used herein "adverse symptom" means a manifestation or condition that is reported by the patient (e.g., pain, nausea, chills, depression, numbness, tingling, anorexia, dysguesia, and the like); whereas an "adverse sign" means an objective finding that is a physically observable manifestation of a condition, adverse event or disease in the patient (e.g., palpable purpura, maculopapular rash, spider angioma, Chvostek's sign, Babinski's sign, Trousseau's sign, opisthotonos, and the like).

Unless otherwise explained, all technical and scientific terms used herein have the same meaning as commonly understood by one of ordinary skill in the art to which this disclosure belongs. Although methods and materials similar or equivalent to those described herein can be used in the practice or the disclosed methods and compositions, suitable methods and materials are described below. All publications, patent applications, patents, and other references mentioned herein are incorporated by reference in their entirety. In case of conflict, the present Specification, including explanations of terms, will control. In addition, the materials, methods, and examples are for illustrative purposes only, and are not intended to be limiting.

I. Karenitecin®/BNP1350

Highly lipophilic camptothecin derivatives (HLCDs), particularly those containing silicon-based moieties, are effective anti-cancer drugs. One of the most noted of the silicon-containing HLCDs is Karenitecin® (also known as BNP1350; IUPAC Nomenclature: (4S)-4-ethyl-4-hydroxy-11-[2-(trimethylsilyl)ethyl]-1H-pyrano[3':4':6,7]indolizino[1,2-b]quinoline-3,14(4H,12H)-dione, and also referred to as 7-(2'-trimethylsilyl)ethyl camptothecin)), currently in human clinical trials in the United States and internationally. U.S. Pat. Nos. 5,910,491 and 6,194,579; and U.S. patent application Ser. No. 10/627,444, filed Jul. 25, 2003, which are incorporated by reference herein in their entirety, describe the compositions, formulations, and processes for making Karenitecin® and other related HLCDs.

For example, the Karenitecin® analogs disclosed and claimed in the present invention, in a non-limiting manner, represent a novel class of chemotherapeutic compounds that have exhibited potent antineoplastic activity against common types of cancer including but not limited to cancers of the lung, breast, prostate, pancreas, head and neck, ovary, colon, as well as melanoma. While these Karenitecin® analogs possess Topoisomerase I inhibitory activity similar to that of other camptothecin derivatives, they also possess novel structural modifications that are rationally designed for superior bioavailability and tissue penetration, while concomitantly avoiding untoward metabolism and drug resistance mechanisms which are common in human and other mammalian cancers.

The present invention discloses analogs of the anti-tumor agent Karenitecin® wherein various types of covalent linkages will connect one of novel substituent groups to the silicon-containing side chain bound to the C7 position on the B-ring of Karenitecin®. However, it should be noted that the silicon of Karenitecin® may also be substituted with germanium. These analogs are amphipathic and exploit the polar side chains to decrease protein binding and to augment intracellular uptake and tissue retention. The polar group on the side chain of these Karenitecin® analogs will reduce drug-binding affinity to plasma proteins, so as to improve plasma protein binding properties while concomitantly maintaining both lactone stability and drug potency. The increased free (i.e., non-plasma protein bound) drug in human plasma will improve the bioavailability of the parent compound. Moreover, as previously discussed, the hydrolysis of the lactone E-ring of the camptothecin molecule (thus forming the water soluble carboxylate form) only possesses approximately one-tenth or less of the anti-tumor potency of the original, non-hydrolyzed closed lactone E-ring form of the camptothecin molecule.

It may be ascertained from the pharmacological and biochemical data presented in Section IV, in THE BACKGROUND OF THE INVENTION section, that many of the previously synthesized camptothecin analogs possess a number of inherent limitations which markedly decreases their usefulness as anti-cancer agents. In contrast, Karenitecin® is a highly lipophilic camptothecin derivative characterized by substantial lactone stability and long plasma half-life. In vitro studies conducted on a panel of over 20 human cancer cell lines indicate that Karenitecin® is significantly more potent antitumor agent than either Topotecan™ or SN-38, the active metabolite of Irinotecan™. Equilibrium dialysis studies with human plasma demonstrated that Karenitecin® is 98 to 99% protein-bound. The free drug concentration in blood plasma is generally considered to be the pharmacologically active form in clinical pharmacology.

The C7 position of the B-ring is one of the preferred sites of chemical modification using new chemical substituents which impart useful pharmacological, biological and chemical properties to these new compositions of matter. Certain lipophilic substitutions at the C7 position of camptothecin incorporate chemical groups via Minisci-type free radical alkylations on a protonated camptothecin or on modified derivatives (e.g., Karenitecin®). Minisci-type regiospecific alkylations permit the creation of a one carbon less alkyl chain with respect to the starting aldehyde or alcohol or carboxylic acid. The reaction mechanism suggests that in the case of an aldehyde the introduction of the side chain occurs via an in situ decarbonylation to generate a one carbon less alkyl radical with concomitant evolution of carbon monoxide.

The present invention also teaches a process of regiospecific homolytic acylation of camptothecin at the C7 position based upon a Minisci-type reaction. A slight variation to the earlier stated methodology for C7 alkylation permits the stabilization of the transient acyl radical that enables acylation of camptothecin in high yields. The present invention additionally describes processes to furnish certain key versatile synthons for making transformations at the C7 position.

In addition, the analogs of the present invention have significant utility as highly efficacious chemotherapeutic drugs, and are significantly less toxic than previously disclosed camptothecin derivatives. These novel analogs also may not undergo A-ring or B-ring glucuronidation (and implicitly deglucuronidation), similar to the parent Karenitecin® molecule. The lack of glucuronidation decreases deleterious physiological side-effects (e.g., diarrhea, leukopenia) and may also mitigate substantial interpatient variability in drug levels of the free metabolite and its glucuronide conjugate. Furthermore, these novel analogs are not prodrugs, requiring metabolic activation.

Thus, in summation, the many of the novel Karenitecin® analogs of the present invention: (i) possess potent antitumor activity (i.e., in nanomolar or subnanomolar concentrations) for inhibiting the growth of human and animal tumor cells in vitro; (ii) are potent inhibition of Topoisomerase I; (iii) lack of susceptibility to MDR/MRP drug resistance; (iv) require no metabolic drug activation: (v) lack glucuronidation of the A-ring or B-ring; (vi) reduce drug-binding affinity to plasma proteins; (vii) maintain lactone stability; (viii) maintain drug potency; and (ix) possess a low molecular weight (e.g., MW<600).

The novel Karenitecin® analogs disclosed and claimed in the present invention possess the generic structural formula illustrated, below.

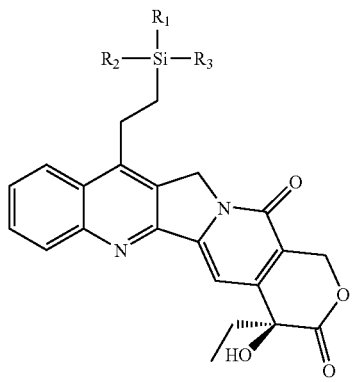

wherein:

$R_1$, $R_2$, $R_3$=short alkyl chain or alkyl chain containing polar functional groups linked to the silicon-containing (or germanium-containing) side chain (bound to C7 on the B-ring) of Karenitecin®.

II. General Reaction Procedures

A. Minisci Reaction

To a slurry of ferrous sulfate heptahydrate (0.8 g) in 30% sulfuric acid (5 mL), a solution of aldehyde or their corresponding acetals (11.6 mmol) in 1,2-dimethoxyethane (20 mL) was introduced and the reaction mixture was stirred at room temperature. To the above reaction mixture, a solution of camptothecin (1.0 g, 2.9 mmol) in 30% sulfuric acid (55 mL) containing $H_2O_2$ (30%, 0.33 mL) was added dropwise during 10 min and the reaction mixture was stirred for 15 min. Finally, additional $H_2O_2$ (30%, 1.0 mL) was directly introduced into the reaction mixture and allowed to stir overnight. The reaction mixture was first washed with n-hexane (100 mL) to remove non-polar impurities and the required product was obtained by extracting the aqueous layer with chloroform (2×50 mL). The combined chloroform layer was washed once with process water (15 mL) and the layers were separated. The organic layer was dried and concentrated under reduced pressure to dryness and the crude material was purified on a silica gel column using ethanol-dichloromethane mixture to obtain the pure product in mentioned yields.

B. Acetylation

To a slurry of camptothecin derivative (1.1 mmol) in dichloromethane (5 mL) at 0° C., pyridine (2.5 mL) and acetic anhydride (2.0 mL) were added in sequence and the reaction mixture was stirred under argon. The reaction content was stirred for 5 min at 0° C. and a catalytic amount of 4-dimethyl amino pyridine (DMAP; ~5 mg) was introduced and the reaction mixture was stirred at room temperature for 2 days. The reaction mixture was concentrated under reduced pressure to dryness and the residue was partitioned between dichloromethane (30 mL) and saturated ammonium chloride solution (15 mL). The layers were separated and the organic solution was dried, concentrated under reduced pressure and purified on a silica gel column using ethanol-dichloromethane mixture to obtain the acetylated product in mentioned yield.

C. Deacetylation

To a solution of the acetylated camptothecin derivative (50 mg) in methanol (2.5 mL), $K_2CO_3$ (25 mg) was added and stirred at room temperature between 6-24 hours (based upon TLC). The reaction mixture was quenched with acetic acid (0.5 mL) and the reaction mixture was concentrated under reduced pressure. The obtained residue was partitioned between 1N HCl (2 mL) and chloroform (2×10 mL). The combined organic layer was dried and concentrated to obtain the crude product, which was purified on a silica gel using ethanol-dichloromethane mixture to obtain the required product in mentioned yield.

D. Hydrogenation

A slurry of camptothecin derivative (800 mg) and Pd/C (10%, 80 mg) in methanol (30 mL) containing trifluoroacetic acid (0.5 mL) was hydrogenated using a balloon pressure of hydrogen for 16 hours at room temperature. Pd/C was separated off from the reaction mixture and the reaction mixture was concentrated under reduced pressure to obtain the required product in quantitative yields.

E. Urea Formation

To a slurry of amino camptothecin derivative (0.1 mmol) in dry tetrahydrofuran (THF; 2 mL), $K_2CO_3$ (0.3 mmol) and phenyl isocyanate or diethylcarbamyl chloride or dimethylcarbamyl chloride (0.2 mmol) were added and the reaction mixture was stirred at room temperature for 3 hours. The reaction mixture was quenched with acetic acid (0.2 mL) and concentrated under reduced pressure. The residue was purified on a silica gel column using ethanol-dichloromethane mixture to afford the required product in mentioned yields.

F. Mercaptoetherification

A mixture of camptothecin derivative (0.1 mmol) and mercaptan (0.2 mmol) in N,N-dimethyl formamide (DMF; 1 mL), containing $NaHCO_3$ (0.2 mmol) was heated at 70° C. under argon for 3 hours. The DMF was removed under vacuum and the crude residue was purified on a silica gel using ethanol-dichloromethane mixture to afford the required product in good yields.

III. Synthesis of Karenitecin® Analogs 1. Synthesis of 3,3-dimethoxypropyl dimethylvinylsilane

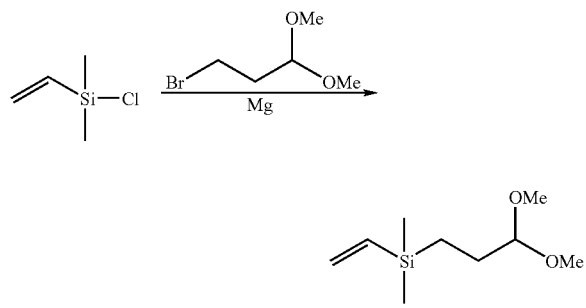

To a stirring magnesium granules (365 mg) in anhydrous tetrahydrofuran (15 mL), few drops of dibromoethane (~50 μL) was added at room temperature under argon and the resultant mixture was stirred for 10 min. The reaction mixture was cooled to 10° C. and 3-bromopropionaldehyde dimethyl acetal (2.2 g) was introduced dropwise during 10 min. and allowed to stir at room temperature for 2 hours. After the completion of the Grignard formation, the reaction mixture was cooled to 0° C. and chlorodimethylvinylsilane (1.2 g) was added dropwise and the reaction mixture was stirred overnight at room temperature. The reaction mixture was quenched with water (20 mL) at 0° C. and the organics were extracted with t-butyl methyl ether (2×20 mL). The combined organic layers were dried and concentrated under reduced pressure to obtain the crude product. The pure product was obtained upon vacuum distillation of the crude material at 100° C. (2 mm Hg) in 80% yield (1.5 g).

$^1$H NMR (300 MHz, δ, CDCl$_3$) 6.12 (dd, 1H, J=14.7, 19.8 Hz), 5.95 (dd, 1H, J=4.2, 14.7 Hz), 5.67 (dd, 1H, J=4.2, 20.1 Hz), 4.28 (t, 1H, J=5.7 Hz), 3.31 (s, 6H), 1.65-1.50 (m, 2H), 0.65-0.50 (m, 2H), 0.07 (s, 6H).

2. Synthesis of 11-(4S)-[2-(dimethylvinylsilanyl)-ethyl]-4-ethyl-4-hydroxy-1,12-dihydro-4H-2-oxa-6,12a-diaza-dibenzo[b,h]fluorene-3,13-dione (Compound 1)

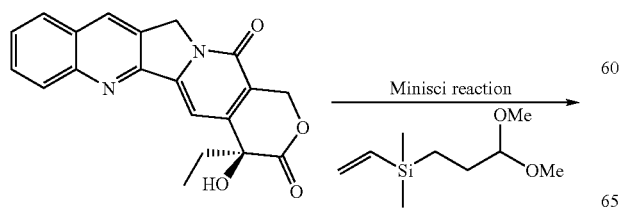

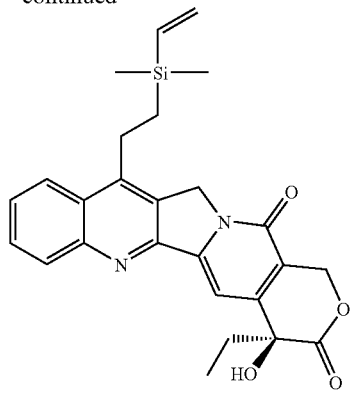

Prepared according to Procedure A using 3,3-dimethoxypropyl dimethylvinylsilane, the crude product was purified on a silica gel column using 1% ethanol in dichloromethane to obtain the pure product in 35% yield.

$^1$H NMR (300 MHz, δ, CDCl$_3$) 8.23 (d, 1H, J=8.4 Hz), 8.03 (d, 1H, J=8.4 Hz), 7.85-7.74 (m, 1H), 7.71-7.60 (m, 2H), 6.40-6.04 (m, 2H), 5.90-5.70 (m, 2H), 5.31 (d, 1H, J=16.2 Hz), 5.23 (s, 2H), 3.78 (s, 1H), 3.20-3.00 (m, 2H), 2.05-1.80 (m, 2H), 1.15-0.85 (m, 5H), 0.25 (s, 6H).

3. Synthesis of acetic acid 11-(4S)-[2-(dimethylvinylsilanyl)-ethyl]-4-ethyl-3,13-dioxo-3,4,12,13-tetrahydro-1H-2-oxa-6,12a-diaza-dibenzo[b,h]fluoren-4-yl ester (Compound 2)

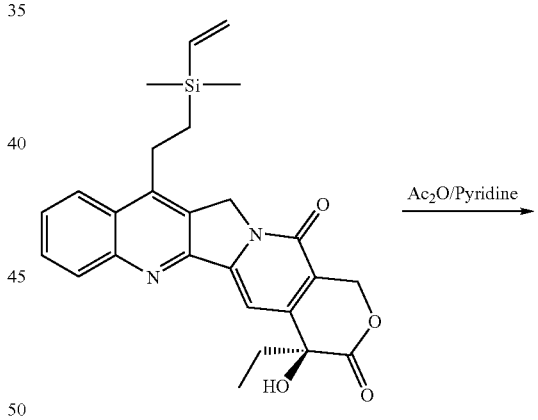

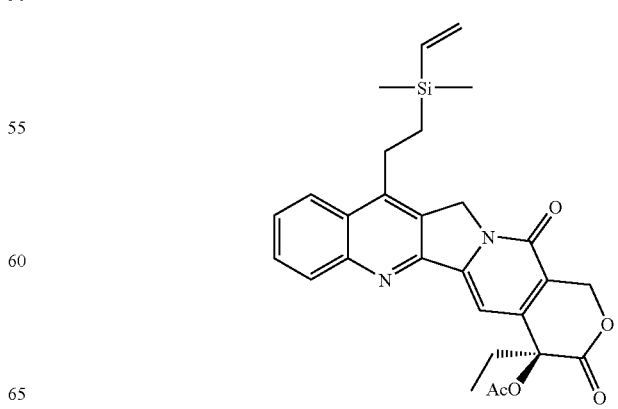

Prepared according to Procedure B using Compound 1 (500 mg), the crude product was purified on a silica gel column using 1% ethanol in dichloromethane to obtain the pure product in 79% yield (431 mg).

$^1$H NMR (300 MHz, δ, CDCl$_3$) 8.23 (d, 1H, J=8.3 Hz), 8.04 (d, 1H, J=8.4 Hz), 7.86-7.60 (m, 2H), 7.24 (s, 1H), 6.40-6.04 (m, 2H), 5.90-5.73 (m, 1H), 5.68 (d, 1H, J=16.5 Hz), 5.40 (d, 1H, J=16.2 Hz), 5.22 (s, 2H), 3.20-3.00 (m, 2H), 2.40-2.00 (m, 2H), 2.22 (s, 3H), 1.10-0.85 (m, 5H), 0.25 (s, 6H).

4. Synthesis of chloromethyldimethylsilyl-3-propanal

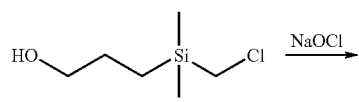
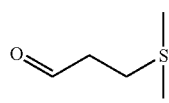

To a solution of chloromethyldimethylsilyl-3-propanol (2.0 g) and 2,2,6,6-tetramethyl-1-piperidinyloxy (20 mg) in dichloromethane (20 mL), NaBr (100 mg) and deionized water (20 mL) were added and stirred for 15 min. A stock solution of NaOCl (34 mL, 4% solution) and deionized water (6 mL) and NaHCO$_3$ (2 g) was prepared and slowly introduced in to the above reaction mixture slowly and allowed to stir at room temperature for 1 hour. The layers were separated and the aqueous portion was once extracted with dichloromethane (20 mL). The combined organic layer was washed once with water (10 mL), dried and concentrated under water aspirator to obtain the crude product in 80% yield, which was advanced to Minisci type reaction without further purification.

$^1$H NMR (300 MHz, δ, CDCl$_3$) 9.77 (s, 1H), 2.80 (s, 2H), 2.60-2.40 (m, 2H), 1.00-0.80 (m, 2H), 0.14 (s, 6H).

5. Synthesis of 11-(4S)-[2-(chloromethyldimethylsilanyl)-ethyl]-4-ethyl-4-hydroxy-1,12-dihydro-4H-2-oxa-6,12a-diaza-dibenzo[b,h]fluorene-3,13-dione (Compound 3)

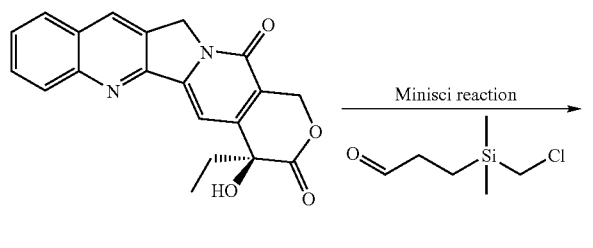

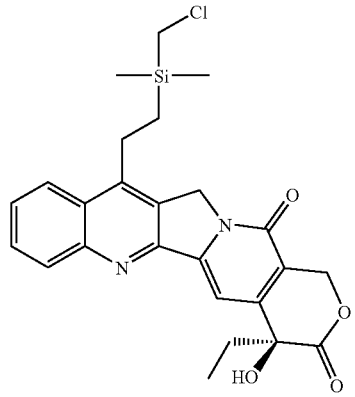

Prepared according to Procedure A, using chloromethyldimethylsilyl-3-propanal, the crude product was purified on a silica gel column using 1% ethanol in dichloromethane to obtain the pure product in 55% yield.

$^1$H NMR (300 MHz, δ, CDCl$_3$) 8.25 (d, 1H, J=8.4 Hz), 8.08 (d, 1H, J=7.8 Hz), 7.80 (t, 1H, J=7.6 Hz), 7.78-7.60 (m, 2H), 5.78 (d, 1H, 16.5 Hz), 5.30 (d, 1H, J=16.5 Hz), 5.25 (s, 2H), 3.24-3.12 (m, 2H), 2.95 (s, 2H), 2.00-1.80 (m, 2H), 1.20-1.00 (m, 5H), 0.30 (s, 6H).

6. Synthesis of 11-(4S)-[2-(iodomethyldimethylsilanyl)-ethyl]-4-ethyl-4-hydroxy-1,12-dihydro-4H-2-oxa-6,12a-diaza-dibenzo[b,h]fluorene-3,13-dione (Compound 4)

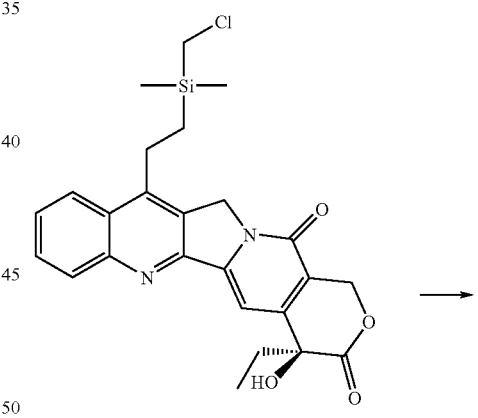

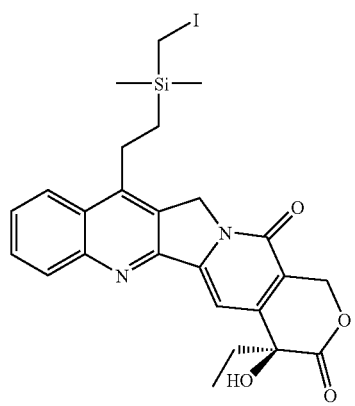

A solution of Compound 3 (200 mg) and sodium iodide (200 mg) in 2-butanone (4 mL) was heated at 80° C. for 24 hours. Solvent was removed under reduced pressure and directly purified on a silica gel using 1% ethanol in dichloromethane to obtain the required product in 85% yield (200 mg).

$^1$H NMR (300 MHz, δ, CDCl$_3$) 8.24 (d, 1H, J=8.4 Hz), 8.12 (d, 1H, J=7.8 Hz), 7.82 (t, 1H, J=7.6 Hz), 7.78-7.60 (m, 2H), 5.76 (d, 1H, J=16.5 Hz), 5.40-5.22 (m, 3H), 3.25-3.10 (m, 2H), 2.15 (s, 2H), 2.00-1.80 (m, 2H), 1.20-1.00 (m, 5H), 0.33 (s, 6H).

7. Synthesis of 11-(4S)-{2-[(benzylaminomethyl)-dimethylsilanyl]-ethyl}-4-ethyl-4-hydroxy-1,12-dihydro-4H-2-oxa-6,12a-diaza-dibenzo[b,h]fluorene-3,13-dione (Compound 5)

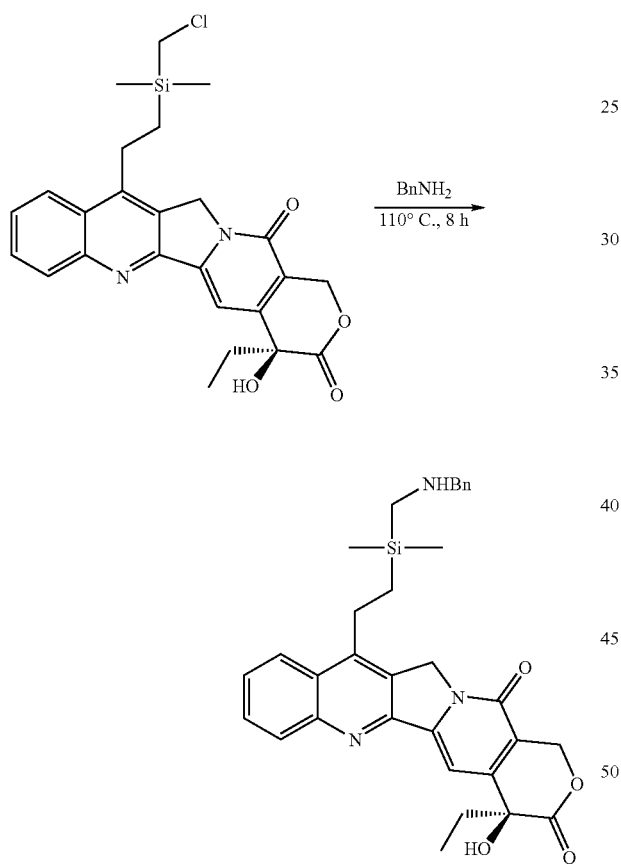

A solution of Compound 3 (100 mg) and benzylamine (70 μL) in acetonitrile (2 mL) was heated at 110° C. over 8 hours. Solvent was removed under reduced pressure and the crude product was stirred in trifluoroacetic acid (1 mL) for 2 hours at room temperature. Finally, trifluoroacetic acid was removed under reduced pressure and the crude product was partitioned between chloroform (20 mL) and 7% aqueous NaHCO$_3$ solution (10 mL). The chloroform layer was dried and concentrated and purified on a silica gel column using 4% ethanol in dichloromethane to obtain the product in 50% yield (57 mg).

$^1$H NMR (300 MHz, δ, CDCl$_3$) 8.20 (d, 1H, J=8.4 Hz), 7.97 (d, 1H, J=8.4 Hz), 7.82-7.58 (m, 3H), 7.40-7.20 (m, 5H), 5.58 (d, 1H, J=16.2 Hz), 5.40-5.17 (m, 3H), 4.02 (bs, 2H), 3.20-3.00 (m, 2H), 2.29 (s, 2H), 2.00-1.78 (m, 2H), 1.22-1.08 (m, 2H), 1.01 (t, 3H, 7.2 Hz), 0.26 (s, 3H), 0.22 (s, 3H).

HRMS m/z: [M+Na]$^+$ found 576.2274, calcd 576.2289 (C$_{32}$H$_{35}$N$_3$O$_4$SiNa).

8. Synthesis of acetic acid-(4S)-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl ester (Compound 6)

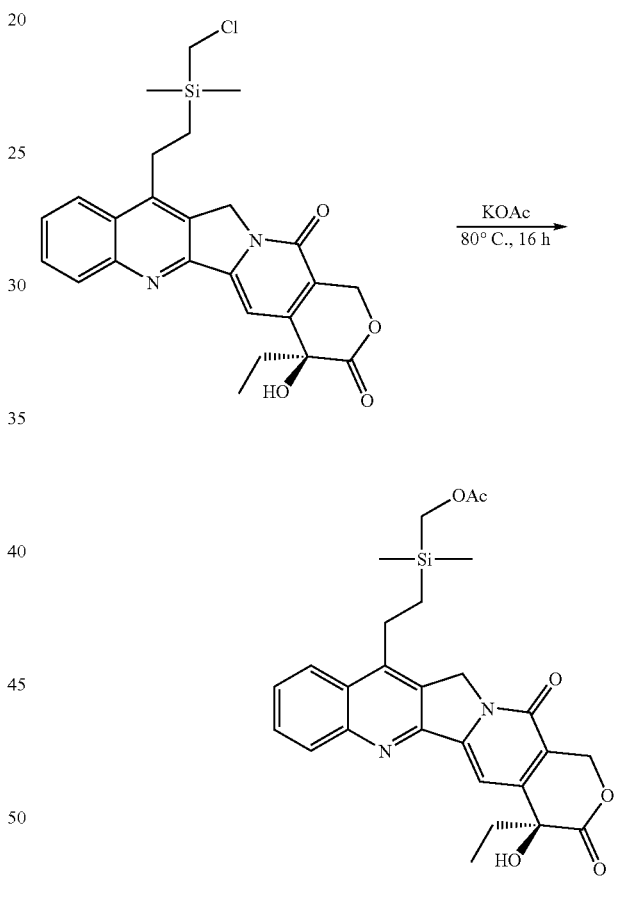

A solution of Compound 3 (200 mg) and potassium acetate (200 mg) in dry N,N-dimethylformamide (4 mL) was heated at 80° C. for 16 hours. The reaction mixture was cooled to room temperature and the N,N-dimethylformamide was removed under vacuum with mild heating. The obtained crude material was directly purified on a silica gel column using 1-2% ethanol in dichloromethane to obtain the required product in 72% yield (150 mg).

$^1$H NMR (300 MHz, δ, CDCl$_3$) 8.30 (d, 1H, J=8.2 Hz), 8.08 (d, 1H, J=8.4 Hz), 7.90-7.60 (m, 3H), 5.78 (d, 1H, J=16.5 Hz), 5.40-5.20 (m, 3H), 3.95 (s, 2H), 3.24-3.10 (m, 2H), 2.14 (s, 3H), 2.00-1.80 (m, 2H), 1.20-0.95 (m, 5H), 0.25 (s, 6H).

9. Synthesis of (4S)-4-ethyl-4-hydroxy-11-[2-(hydroxymethyldimethylsilanyl)-ethyl]-1,12-dihydro-4H-2-oxa-6,12a-diaza-dibenzo[b,h]fluorene-3,13-dione (Compound 7)

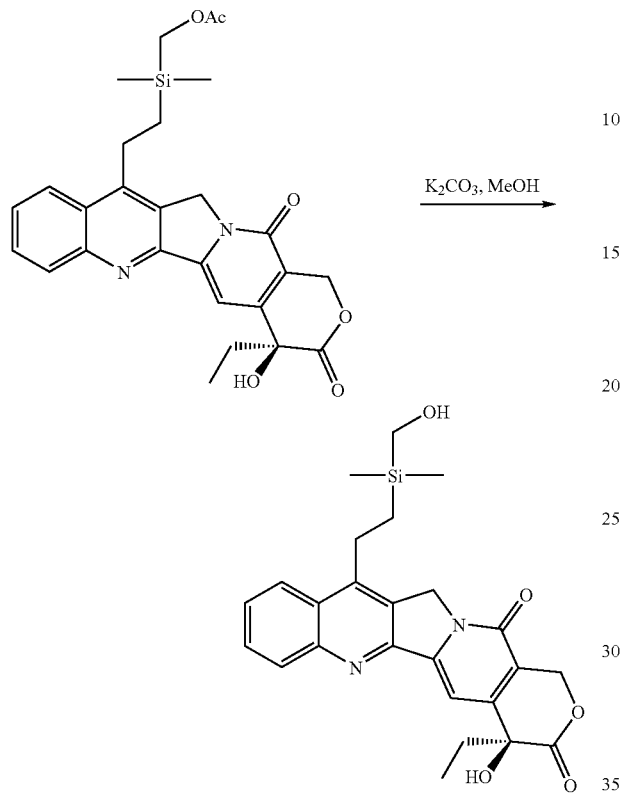

Prepared according to Procedure C, using Compound 6 (25 mg), the crude product was purified on a silica gel column using 2% ethanol in dichloromethane to obtain the required product in 78% yield (18 mg).

$^1$H NMR (300 MHz, δ, CDCl$_3$) 8.30 (d, 1H, J=8.4 Hz), 8.14 (d, 1H, J=8.7 Hz), 7.90-7.60 (m, 3H), 5.74 (d, 1H, J=16.5 Hz), 5.40-5.22 (m, 3H), 3.61 (s, 2H), 3.30-3.18 (m, 2H), 2.00-1.80 (m, 2H), 1.20-0.95 (m, 5H), 0.22 (s, 6H).

10. Synthesis of (2R,4S)-2-tert-butoxycarbonylamino-3-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-methylsulfanyl)-propionic acid methyl ester (Compound 8)

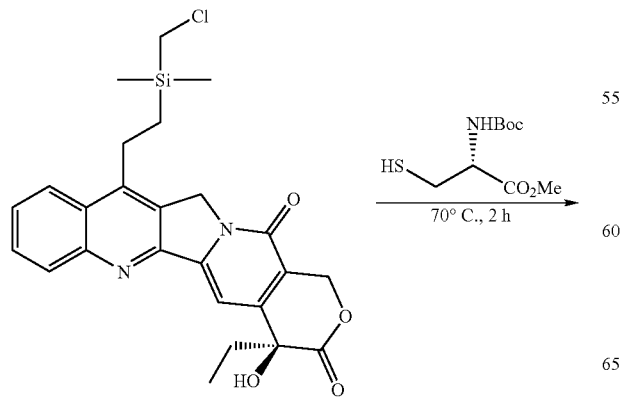

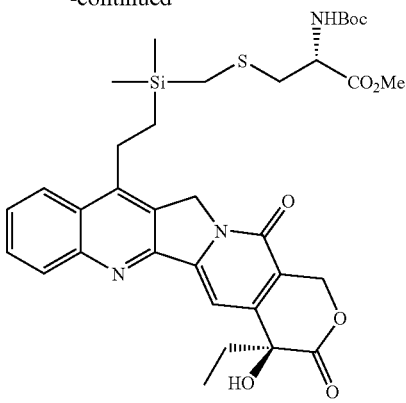

Prepared according to Procedure F, using Compound 3 and N-(t-butoxycarbonyl)-L-cysteine methyl ester, the crude product was purified on a silica gel column using 2% ethanol in dichloromethane to obtain the pure product in 57% yield.

$^1$H NMR (300 MHz, δ, CDCl$_3$) 8.23 (d, 1H, J=8.4 Hz), 8.10 (d, 1H, J=8.4 Hz), 7.80 (t, 1H, J=7.2 Hz), 7.68 (s, 1H), 7.70-7.60 (m, 1H), 5.75 (d, 1H, J=16.5 Hz), 5.40-5.20 (m, 3H), 4.70-4.50 (m, 1H), 3.77 (s, 3H), 3.25-2.90 (m, 4H), 2.15-1.80 (m, 4H), 1.36 (s, 9H), 1.10-0.90 (m, 5H), 0.25 (s, 6H).

11. Synthesis of thioacetic acid S-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)ester (Compound 9)

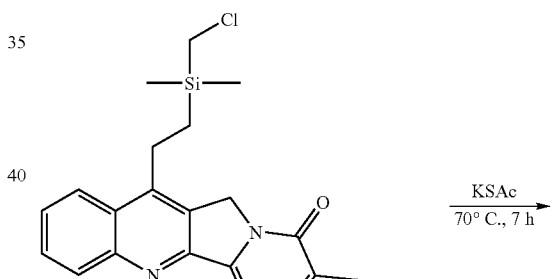

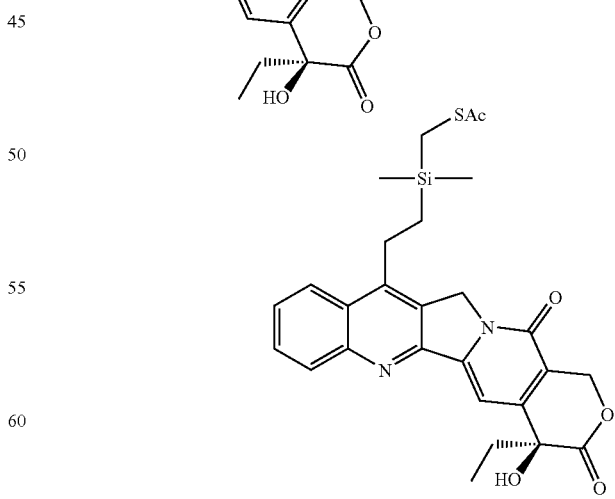

A mixture of Compound 3 (300 mg) and potassium thioacetate (400 mg) in N,N-dimethylformamide (2 mL) was heated at 70° C. under argon for 16 hours. The N,N-dimethylformamide was removed under vacuum and the resulting residue was directly eluted on a silica gel using 1% ethanol in dichloromethane to obtain the required product in 74% yield (240 mg).

$^1$H NMR (300 MHz, δ, CDCl$_3$) 8.24 (d, 1H, J=8.4 Hz), 8.04 (d, 1H, J=8.5 Hz), 7.85-7.60 (m, 3H), 5.76 (d, 1H, J=16.5 Hz), 5.30 (d, 1H, J=16.4 Hz), 5.24 (s, 2H), 3.24-3.04 (m, 2H), 2.43 (s, 3H), 2.27 (s, 2H), 2.00-1.80 (m, 2H), 1.18-0.98 (m, 5H), 0.26 (s, 6H).

12. Synthesis of allyl-(2-[1,3]dioxolan-2-yl-ethyl)dimethylsilane

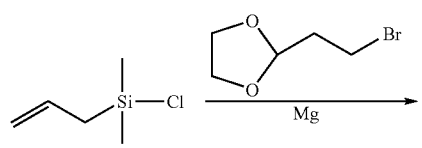

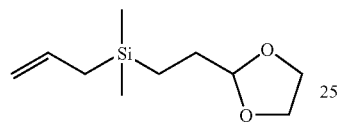

To a slurry of magnesium (2.43 g) in dry tetrahydrofuran (50 mL), few drops of dibromoethane (~50 µL) was added under argon and stirred at room temperature for 10 min. The reaction mixture was cooled to 10° C. and 2-(2-bromoethyl)-1,3-dioxolane (10.9 g) was introduced dropwise during 10 min and allowed to stir at room temperature for 2 hours. The resulting reaction mixture was cooled to −10° C. and allyldimethylchlorosilane (6.73 g) was added dropwise during 10 min. and stirred over night at room temperature. Finally, the reaction content was quenched with aqueous NaHCO$_3$ (15 mL) and extracted with ether (3×50 mL). The combined organic layer was dried and concentrated under mild vacuum to obtain the crude product, which was advanced to the next step without further purification (yield 9.5 g).

$^1$H NMR (300 MHz, δ, CDCl$_3$) 5.86-5.65 (m, 1H), 4.90-4.75 (m, 3H), 4.05-3.80 (m, 4H), 1.70-1.40 (m, 4H), 0.70-0.50 (m, 2H), 0.0 (s, 6H).

13. Synthesis of 3-(2-[1,3]dioxolan-2-yl-ethyl)dimethylsilanylpropan-1-ol

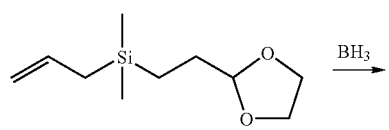

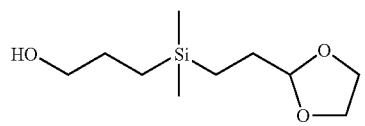

A solution of allyl-(2-[1,3]dioxolan-2-yl-ethyl)dimethylsilane (2.0 g) in dry tetrahydrofuran (5 mL) was added dropwise to a 1 molar borane solution in tetrahydrofuran (4 mL) at 0° C. under argon. The reaction mixture was allowed to stir at room temperature for 2 hours and quenched by an addition of aqueous 3 N NaOH solution (1.7 mL) under ice. Hydrolysis of the borate complex was done under ice by a careful addition of H$_2$O$_2$ (30%, 1.6 mL) and the resulting mixture was allowed to stir for 2 hours at room temperature. The crude product was obtained by adding K$_2$CO$_3$ (500 mg) to the reaction mixture and extracting with t-butyl methyl ether (2×20 mL). The combined organic layer was washed once with brine (10 mL), dried and concentrated under reduced pressure to obtain the required product in 86% yield, which was advanced to Minisci type reaction without further purification.

$^1$H NMR (300 MHz, δ, CDCl$_3$) 4.80 (t, 1H, J=4.7 Hz), 4.00-3.80 (m, 4H), 3.58 (t, 2H, J=6.6 Hz), 1.72-1.45 (m, 4H), 0.65-0.40 (m, 4H), 0.0 (s, 6H).

14. Synthesis of 4S-4-ethyl-4-hydroxy-11-{2-[(3-hydroxypropyl)-dimethylsilanyl]-ethyl}-1,12-dihydro-4H-2-oxa-6,12a-diaza-dibenzo[b,h]fluorene-3,13-dione (Compound 10)

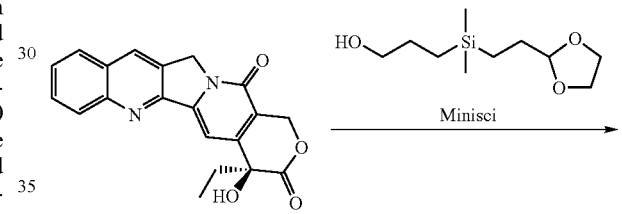

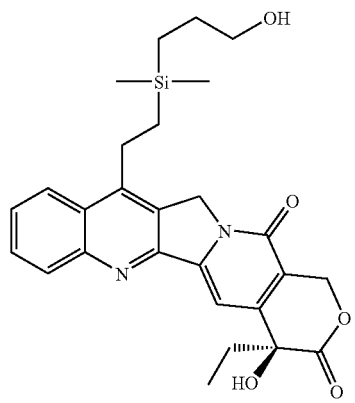

Prepared according to Procedure A, using 3-(2-[1,3]dioxolan-2-yl-ethyl)dimethylsilylpropan-1-ol, the crude product was purified on a silica gel column using 2% ethanol in dichloromethane to obtain the pure product in 53% yield.

$^1$H NMR (300 MHz, δ, CDCl$_3$) 8.25 (d, 1H, J=7.8 Hz), 8.04 (d, 1H, J=8.0 Hz), 7.85-7.60 (m, 2H), 7.72 (s, 1H), 5.74 (d, 1H, J=16.2 Hz), 5.30 (d, 1H, J=16.2 Hz), 5.24 (s, 2H), 3.68 (t, 2H, J=6.6 Hz), 3.20-3.00 (m, 2H), 2.00-1.80 (m, 2H), 1.75-1.58 (m, 2H), 1.04 (t, 3H, J=7.4 Hz), 1.00-0.88 (m, 2H), 0.80-0.64 (m, 2H), 0.19 (s, 3H), 0.18 (s, 3H).

MS (m/z, M+1): 493

15. Synthesis of (4S)-11-{2-[(3-bromopropyl)-dimethylsilanyl]-ethyl}-4-ethyl-4-hydroxy-1,12-dihydro-4H-2-oxa-6,12a-diaza-dibenzo[b,h]fluorene-3,13-dione (Compound 11)

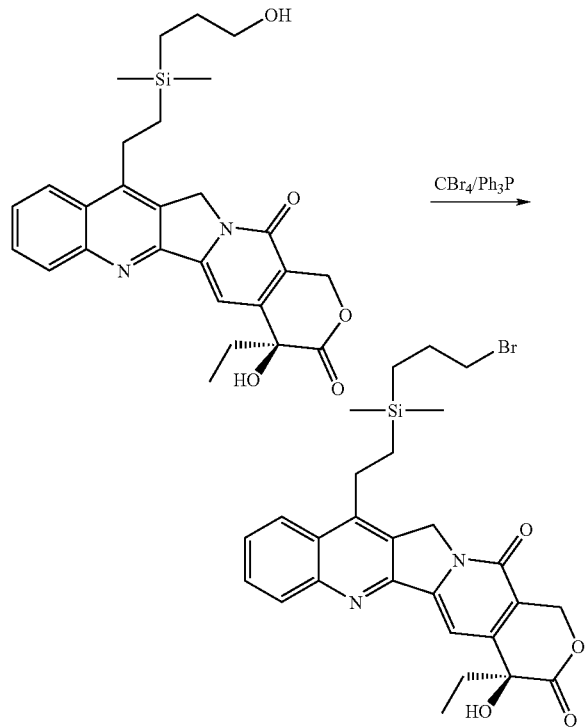

To a slurry of Compound 10 (1.5 g) and carbon tetrabromide (2.02 g) in dry tetrahydrofuran (10 mL) at room temperature, a solution of Ph$_3$P (880 mg) in tetrahydrofuran (10 mL) was added dropwise and the reaction mixture was allowed to stir for 3 hours under argon. Concentration of the reaction mixture under reduced pressure and elution of the residue through a silica gel using 1% ethanol in dichloromethane yielded the required product in 94% yield (1.6 g).

$^1$H NMR (300 MHz, δ, CDCl$_3$) 8.24 (d, 1H, J=7.9 Hz), 8.00 (d, 1H, J=8.1 Hz), 7.85-7.58 (m, 2H), 7.69 (s, 1H), 5.76 (d, 1H, J=16.3 Hz), 5.27 (d, 1H, J=16.5 Hz), 5.22 (s, 2H), 3.44 (t, 2H), 3.20-3.00 (m, 2H), 2.00-1.76 (m, 4H), 1.10-0.70 (m, 7H), 0.20 (s, 6H).

16. Synthesis of (4S)-11-{2-[(3-iodopropyl)-dimethylsilanyl]-ethyl}-4-ethyl-4-hydroxy-1,12-dihydro-4H-2-oxa-6,12a-diaza-dibenzo[b,h]fluorene-3,13-dione (Compound 12)

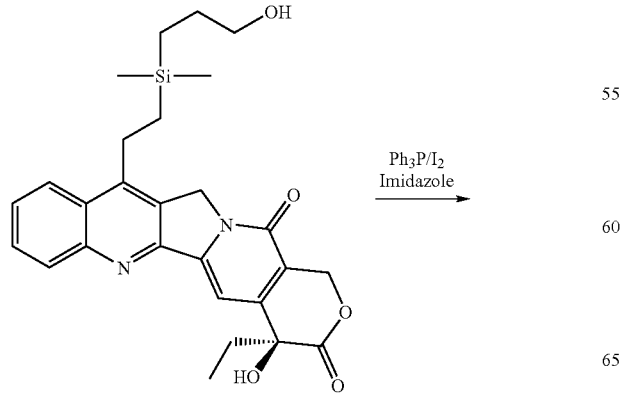

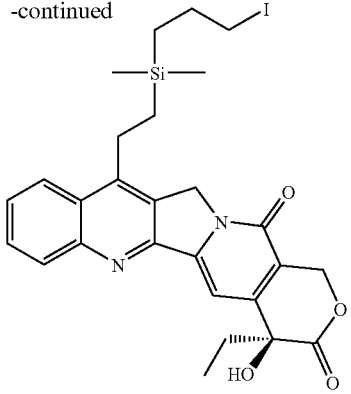

To a slurry of Compound 10 (200 mg), Ph$_3$P (160 mg) and imidazole (55 mg) in dry tetrahydrofuran (5 mL), a solution of iodine (155 mg) in tetrahydrofuran (5 mL) was added dropwise and the reaction mixture was stirred at room temperature for 3 hours under argon. The reaction mixture was concentrated under reduced pressure and the crude residue was partitioned between dichloromethane (20 mL) and saturated aqueous Na$_2$S$_2$O$_3$ solution (10 mL). The organic layer was separated, dried and concentrated to obtain the crude product, which was purified on a silica gel column using 1% ethanol in dichloromethane to obtain the required product in 74% yield (180 mg).

$^1$H NMR (300 MHz, δ, CDCl$_3$) 8.25 (d, 1H, J=7.5 Hz), 8.04 (d, 1H, J=8.4 Hz), 7.86-7.60 (m, 3H), 5.76 (d, 1H, J=16.5 Hz), 5.32 (d, 1H, J=16.2 Hz), 5.25 (s, 2H), 3.25 (t, 2H, J=7.05 Hz), 3.20-3.00 (m, 2H), 2.00-1.80 (m, 4H), 1.04 (t, 3H, J=7.5 Hz), 1.00-0.83 (m, 2H), 0.82-0.68 (m, 2H), 0.20 (s, 6H).

17. Synthesis of (4S)-11-{2-[(3-benzenesulfonylpropyl)-dimethylsilanyl]-ethyl}-4-ethyl-4-hydroxy-1,12-dihydro-4H-2-oxa-6,12a-diaza-dibenzo[b,h]fluorene-3,13-dione (Compound 13)

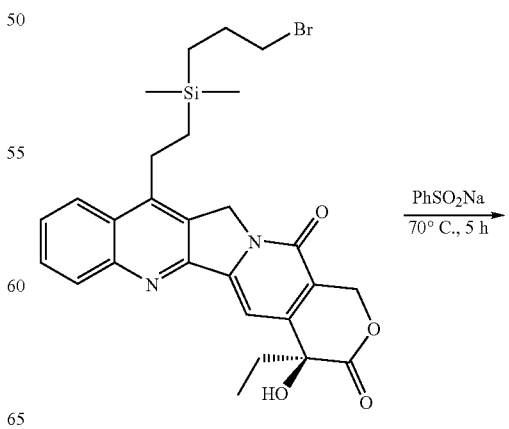

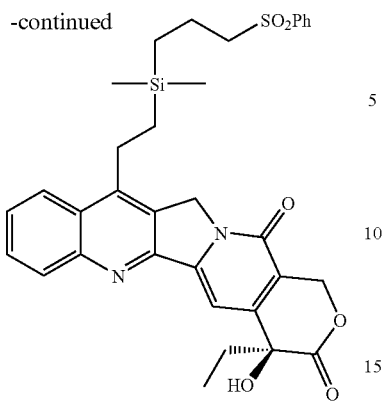

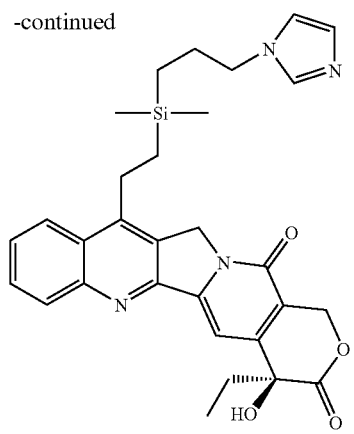

A slurry of Compound 11 (25 mg) and benzenesulfinic acid, sodium salt (15 mg) in N,N-dimethylformamide (0.5 mL) was heated at 70° C. for 5 hours under argon. The N,N-dimethylformamide was removed from the reaction mixture under vacuum and the residue was directly eluted on a silica gel using 2% ethanol in dichloromethane to obtain the required product in quantitative yield (28 mg).

$^1$H NMR (300 MHz, δ, CDCl$_3$) 8.22 (d, 1H, J=7.8 Hz), 8.06-7.38 (m, 9H), 5.75 (d, 1H, J=16.5 Hz), 5.28 (d, 1H, J=16.4 Hz), 5.20 (s, 2H), 3.22-3.00 (m, 4H), 2.02-1.70 (m, 4H), 1.03 (t, 3H, J=7.5 Hz), 1.00-0.82 (m, 2H), 0.80-0.66 (m, 2H), 0.17 (s, 6H).

MS (m/z, M+1): 617

A solution of Compound 11 (60 mg) and imidazole (37 mg) in dry N,N-dimethylformamide (1 mL) was heated at 70° C. for 16 hours under argon. The N,N-dimethylformamide was removed from the reaction mixture under vacuum and the residue was directly eluted on a silica gel column using 3% ethanol in dichloromethane to obtain the required product in 77% yield (45 mg).

$^1$H NMR (300 MHz, δ, CDCl$_3$) 8.20 (dd, 1H, J=0.75, 8.6 Hz), 7.93 (d, 1H, J=8.1 Hz), 7.76 (t, 1H, J=7.2 Hz), 7.68 (s, 1H), 7.63 (t, 1H, J=7.2 Hz), 7.55 (s, 1H), 7.06 (s, 1H), 6.93 (t, 1H, J=1.2 Hz), 5.71 (d, 1H, J=16.2 Hz), 5.28 (d, 1H, J=16.5 Hz), 5.18 (s, 2H), 3.95 (t, 1H, J=6.9 Hz), 3.10-2.95 (m, 2H), 2.00-1.65 (m, 4H), 1.01 (t, 3H, J=7.4 Hz), 0.96-0.82 (m, 2H), 0.62-0.50 (m, 2H), 0.17 (s, 6H).

MS (m/z, M+1): 543

18. Synthesis of (4S)-4-ethyl-4-hydroxy-11-{2-[(3-imidazol-1-yl-propyl)-dimethyl-silanyl]-ethyl}-1,12-dihydro-4H-2-oxa-6,12a-diaza-dibenzo[b,h]fluorene-3,13-dione (Compound 14)

19. Synthesis of (4S)-11-{2-[dimethyl-(3-[1,2,4]triazol-1-yl-propyl)-silanyl]-ethyl}-4-ethyl-4-hydroxy-1,12-dihydro-4H-2-oxa-6,12a-diaza-dibenzo[b,h]fluorene-3,13-dione (Compound 15)

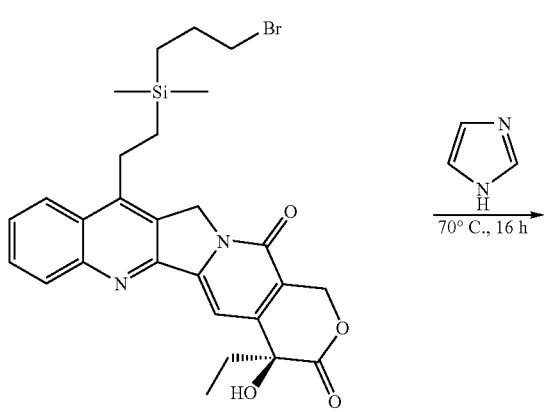

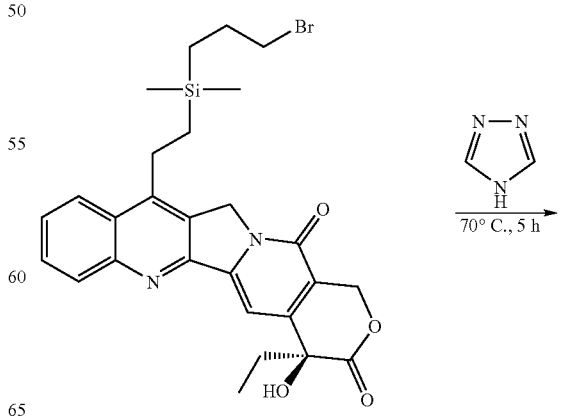

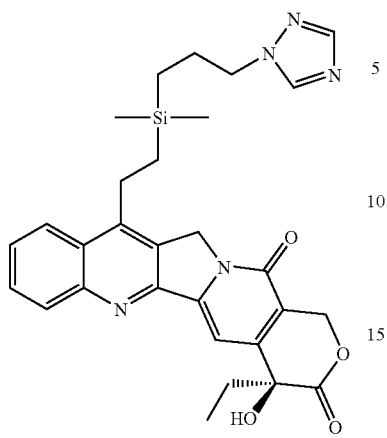

A solution of Compound 11 (50 mg), 1,2,4-triazole (31 mg) and NaHCO₃ (15 mg) in dry N,N-dimethylformamide (1 mL) was heated at 70° C. for 5 hours under argon. The N,N-dimethylformamide was removed from the reaction mixture under vacuum and the residue was directly eluted on a silica gel column using 4% ethanol in dichloromethane to obtain the required product in 61% yield (30 mg).

¹H NMR (300 MHz, δ, CDCl₃) 8.20 (d, 1H, J=7.6 Hz), 8.17 (s, 1H), 8.00 (s, 1H), 7.96 (d, 1H, J=7.5 Hz), 7.82-7.58 (m, 2H), 7.67 (s, 1H), 5.74 (d, 1H, 16.5 Hz), 5.26 (d, 1H, J=16.5 Hz), 5.20 (s, 2H), 4.20 (t, 2H), 3.18-2.98 (m, 2H), 2.02-1.80 (m, 4H), 1.03 (t, 3H, J=7.4 Hz), 1.00-0.84 (m, 2H), 0.70-0.50 (m, 2H), 0.18 (s, 6H).

MS (m/z, M+1): 544

20. Synthesis of (4S)-11-{2-[(3-dimethylaminopropyl)-dimethylsilanyl]-ethyl}-4-ethyl-4-hydroxy-1,12-dihydro-4H-2-oxa-6,12a-diaza-dibenzo[b,h]fluorene-3,13-dione (Compound 16)

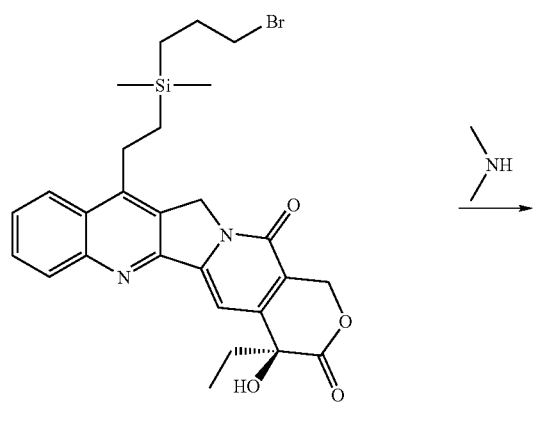

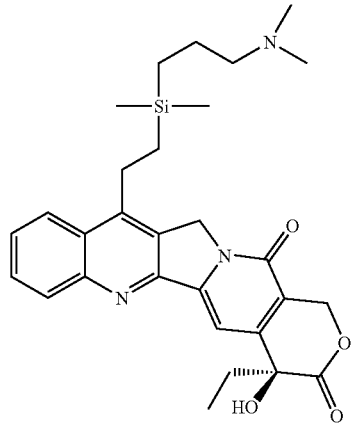

A mixture of Compound 11 (50 mg) and potassium carbonate (37 mg) in deionized water (1 mL) was stirred at room temperature for 30 min. To the resulting mixture, t-BuOH (1 mL) and 2 molar dimethylamine in tetrahydrofuran (0.14 mL) were added and stirred at room temperature for 24 hours. Finally, the reaction mixture was concentrated under vacuum and the resulting residue was dissolved in a mixture of acetic acid (10 mL) and trifluoroacetic acid (1 mL) and stirred at room temperature for 8 hours. The crude material was obtained by concentrating the acetic acid solution under vacuum and the residue was partitioned between 7% aqueous NaHCO₃ solution (5 mL) and chloroform (2×10 mL). The combined organic layer was dried and concentrated and the residue was eluted on a silica gel column using 10% ethanol in dichloromethane to obtain the required product in 56% yield (26 mg).

¹H NMR (300 MHz, δ, CDCl₃) 8.20 (d, 1H, J=7.5 Hz), 8.02 (d, 1H, J=7.5 Hz), 7.94-7.58 (m, 2H), 7.65 (s, 1H), 5.75 (d, 1H, J=16.2 Hz), 5.30 (d, 1H, J=16.2 Hz), 5.23 (s, 2H), 3.20-3.00 (m, 2H), 2.60-2.25 (m, 8H), 2.00-1.80 (m, 2H), 1.70-1.50 (m, 2H), 1.04 (t, 3H, J=7.4 Hz), 1.00-0.84 (m, 2H), 0.76-0.60 (m, 2H), 0.19 (s, 6H).

MS (m/z, M+1): 520

21. Synthesis of (4S)-11-(2-{dimethyl-[3-(2-oxo-2H-pyridin-1-yl)-propyl]-silanyl}-ethyl)-4-ethyl-4-hydroxy-1,12-dihydro-4H-2-oxa-6,12a-diaza-dibenzo[b,h]fluorene-3,13-dione (Compound 17)

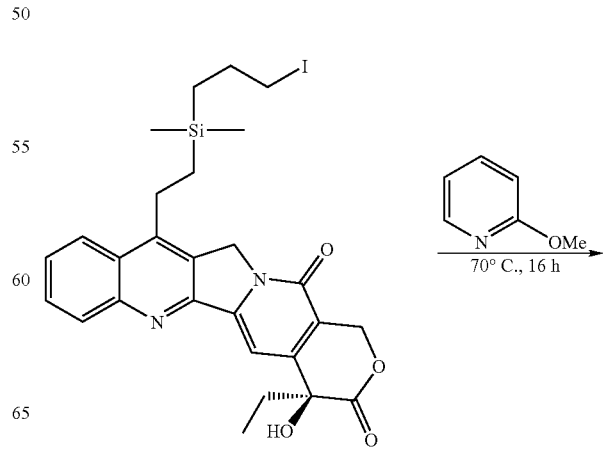

-continued

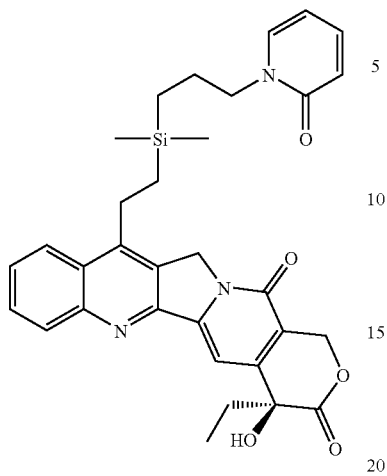

A solution of Compound 12 (60 mg) and 2-methoxypyridine (0.1 mL) in N,N-dimethylformamide (1 mL) was heated at 70° C. for 16 hours. The reaction mixture was concentrated under vacuum and the residue was directly eluted on a silica gel column using 4% ethanol in dichloromethane to obtain the required product in 60% yield (34 mg).

$^1$H NMR (300 MHz, δ, CDCl$_3$) 8.22 (d, 1H, J=8.2 Hz), 8.00 (d, 1H, J=8.4 Hz), 7.82-7.60 (m, 2H), 7.67 (s, 1H), 7.38-7.20 (m, 2H), 6.59 (d, 1H, J=9.2 Hz), 6.26-6.12 (m, 1H), 5.76 (d, 1H, J=16.2 Hz), 5.27 (d, 1H, J=16.2 Hz), 5.21 (s, 2H), 3.95 (t, 2H), 3.18-3.00 (m, 2H), 2.05-1.68 (m, 4H), 1.03 (t, 3H, J=7.4 Hz), 1.00-0.83 (m, 2H), 0.74-0.60 (m, 2H), 0.18 (s, 6H).

MS (m/z, M+1): 570

-continued

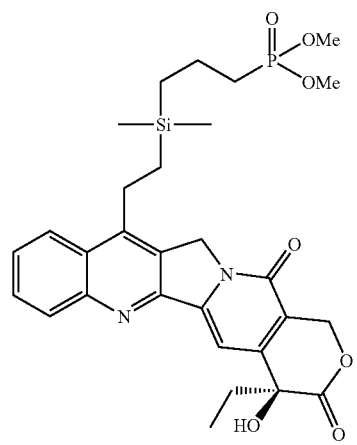

A solution of Compound 12 (60 mg) in trimethyl phosphite (1 mL) was heated under argon at 80° C. for 10 hours. Trimethyl phosphite was removed from the reaction mixture under vacuum and the residue was eluted on a silica gel using 4% ethanol in dichloromethane to obtain the required product in 76% yield (44 mg).

$^1$H NMR (300 MHz, δ, CDCl$_3$) 8.22 (d, 1H, J=7.6 Hz), 8.00 (d, 1H, J=8.3 Hz), 7.84-7.58 (m, 2H), 7.66 (s, 1H), 5.74 (d, 1H, J=16.5 Hz), 5.27 (d, 1H, J=16.4 Hz), 5.20 (s, 2H), 3.76 (s, 3H), 3.72 (s, 3H), 3.20-3.00 (m, 2H), 2.00-1.60 (m, 6H), 1.03 (t, 3H, J=7.5 Hz), 1.00-0.84 (m, 2H), 0.82-0.70 (m, 2H), 0.19 (s, 6H).

MS (n/z, M+1): 585

22. Synthesis of (4S)-(3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-propyl)-phosphonic acid dimethyl ester (Compound 18)

23. Synthesis of (4S)-acetic acid 11-{2-[(3-bromopropyl)-dimethylsilanyl]-ethyl}-4-ethyl-3,13-dioxo-3,4,12,13-tetrahydro-1H-2-oxa-6,12a-diaza-dibenzo[b,h]fluoren-4-yl ester (Compound 19)

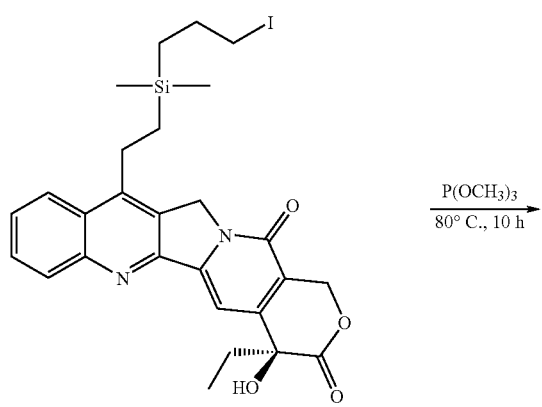

P(OCH$_3$)$_3$
80° C., 10 h

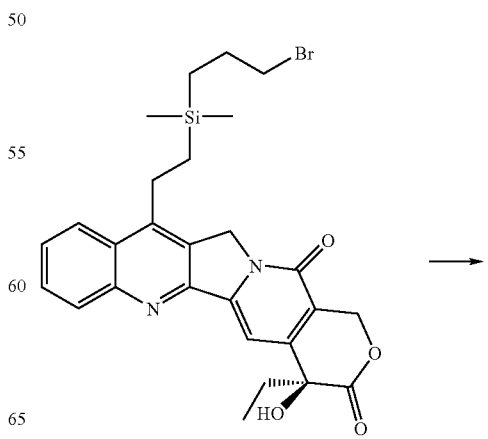

→

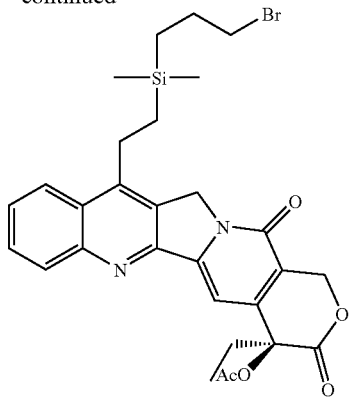

Prepared according to Procedure B, using Compound 11 (500 mg), the crude product was purified on a silica gel column using 1% ethanol in dichloromethane to obtain the pure product in 80% yield (430 mg).

$^1$H NMR (300 MHz, δ, CDCl$_3$) 8.24 (d, 1H, J=7.9 Hz), 8.04 (d, 1H, J=8.1 Hz), 7.85-7.62 (m, 2H), 7.27 (s, 1H), 5.68 (d, 1H, J=16.3 Hz), 5.40 (d, 1H, J=16.5 Hz), 5.24 (s, 2H), 3.44 (t, 2H), 3.20-3.00 (m, 2H), 2.40-2.02 (m, 2H), 2.22 (s, 3H), 2.00-1.80 (m, 2H), 1.10-0.70 (m, 7H), 0.20 (s, 6H).

24. Synthesis of (4S)-acetic acid 11-{2-[(3-azidopropyl)-dimethylsilanyl]-ethyl}-4-ethyl-3,13-dioxo-3,4,12,13-tetrahydro-1H-2-oxa-6,12a-diaza-dibenzo[b,h]fluoren-4-yl ester (Compound 20)

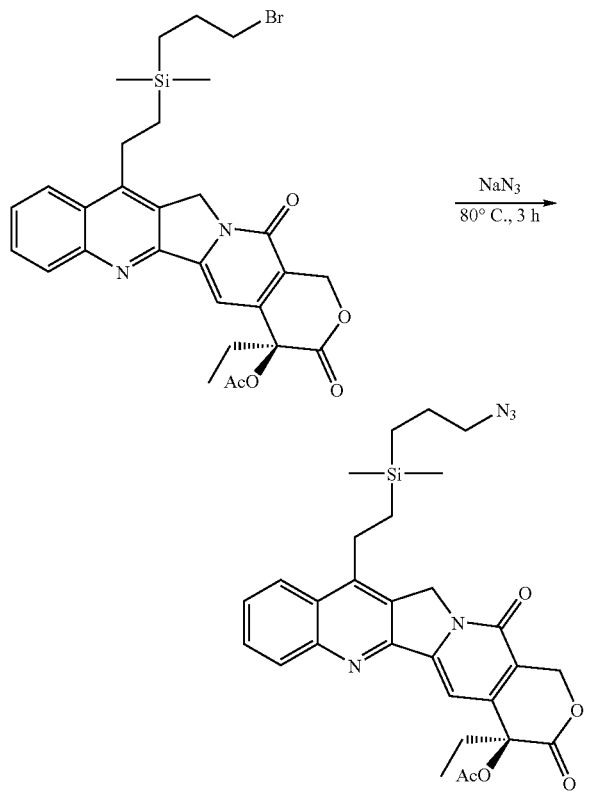

A solution of Compound 19 (1.96 g) and sodium azide (725 mg) in N,N-dimethylformamide (15 mL) was heated at 80° C. for 3 hours. The N,N-dimethylformamide was concentrated under reduced pressure and the residue was partitioned between chloroform (25 mL) and 1 N HCl (10 mL). The organic layer was separated, dried and concentrated to obtain the crude product and was purified by eluting on a silica gel column using 1-2% ethanol in dichloromethane to yield 95% of the required product (1.75 g).

$^1$H NMR (300 MHz, δ, CDCl$_3$) 8.24 (d, 1H, J=8.1 Hz), 8.05 (d, 1H, J=8.1 Hz), 7.90-7.60 (m, 2H), 7.26 (s, 1H), 5.68 (d, 1H, J=17.1 Hz), 5.41 (d, 1H, J=17.1 Hz), 5.24 (s, 2H), 3.31 (t, 2H, J=6.8 Hz), 3.20-3.00 (m, 2H), 2.40-2.00 (m, 2H), 2.22 (s, 3H), 1.74-1.50 (m, 4H), 0.97 (t, 3H, J=7.5 Hz), 1.05-0.85 (m, 2H), 0.80-0.63 (m, 2H), 0.20 (s, 6H).

25. Synthesis of trifluoroacetate-(4S)-3-{[2-(4-acetoxy-4-ethyl-3,13-dioxo-3,4,12,13-tetrahydro-1H-2-oxa-6,12a-diaza-dibenzo[b,h]fluoren-11-yl)-ethyl]-dimethylsilanyl}-propylammonium (Compound 21)

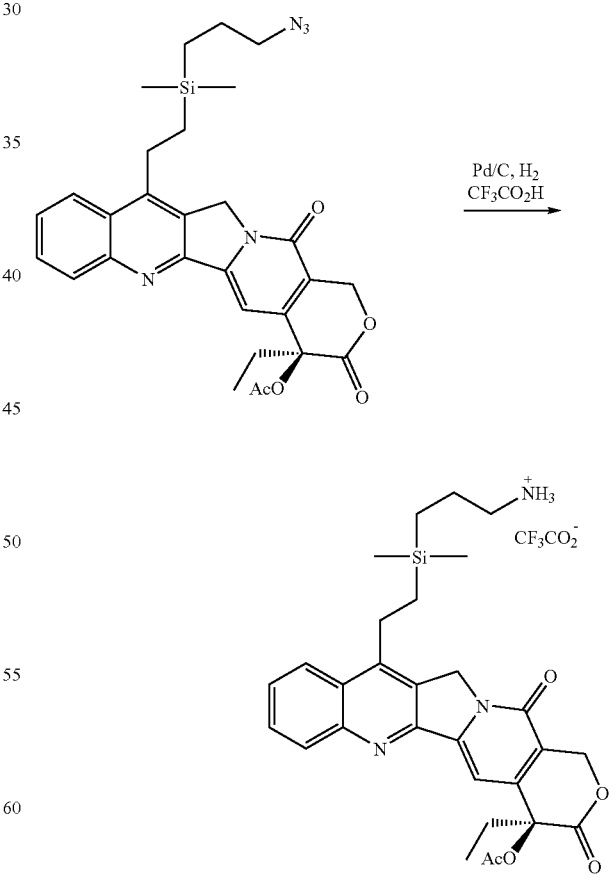

Prepared according to Procedure D, using Compound 20 as starting material, the required product was obtained in quantitative yields.

26. Synthesis of acetic acid (4S)-11-(2-{dimethyl-[3-(2,2,2-trifluoroacetylamino)-propyl]-silanyl}-ethyl)-4-ethyl-3,13-dioxo-3,4,12,13-tetrahydro-1H-2-oxa-6,12a-diaza-dibenzo[b,h]fluoren-4-yl ester (Compound 22)

27. Synthesis of (4S)—N-(3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl)-2,2,2-trifluoro-acetamide (Compound 23)

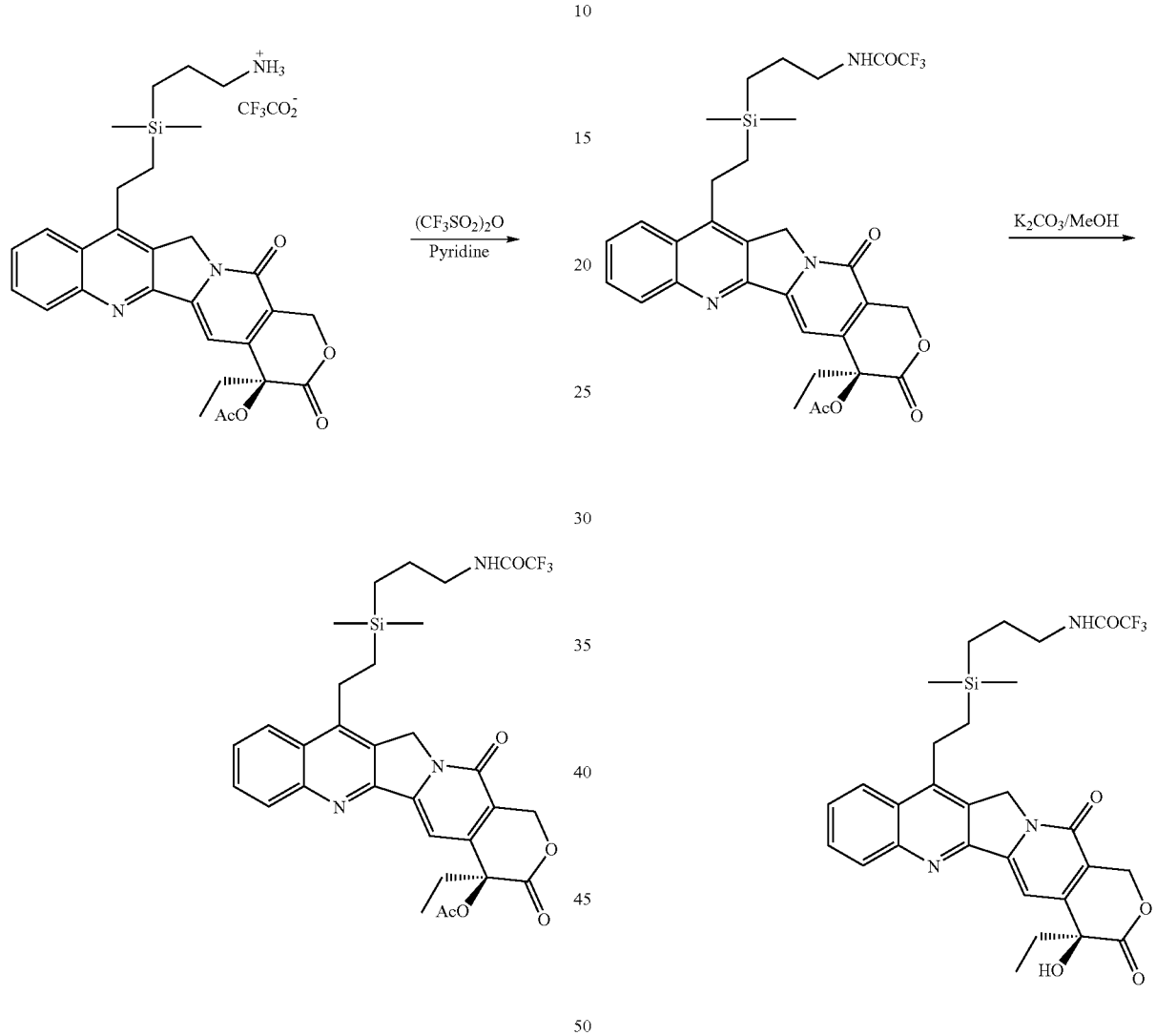

To a solution of Compound 21 (150 mg) in dichloromethane (2 mL) at 0° C., trifluoromethanesulfonic anhydride (80 µL) and pyridine were added and stirred at room temperature for 2 hours. Solvents were dried under vacuum and the crude residue was finally shaken between chloroform (2×10 mL) and 1 N HCl (5 mL). The collective organic layer was dried, evaporated and purified on a silica gel column using 2% ethanol in dichloromethane to obtain 96% of the required product (140 mg).

$^1$H NMR (300 MHz, δ, CDCl$_3$) 8.21 (d, 1H, J=8.4 Hz), 8.02 (d, 1H, J=8.3 Hz), 7.84-7.60 (m, 2H), 7.20 (s, 1H), 5.64 (d, 1H, J=16.7 Hz), 5.39 (d, 1H, J=16.5 Hz), 5.21 (s, 2H), 3.46-3.32 (m, 2H), 3.20-3.00 (m, 2H), 2.38-2.00 (m, 2H), 2.20 (s, 3H), 1.70-1.56 (m, 2H), 1.06-0.82 (m, 5H), 0.80-0.58 (m, 2H), 0.18 (s, 6H).

Prepared according to Procedure C using Compound 22 (100 mg), the crude product was purified on a silica gel column using 3% ethanol in dichloromethane to obtain 69% of the required product (64 mg).

$^1$H NMR (300 MHz, δ, CDCl$_3$) 8.24 (d, 1H, J=7.5 Hz), 8.00 (d, 1H, J=8.4 Hz), 7.86-7.60 (m, 2H), 7.69 (s, 1H), 7.05 (bs, 1H), 5.71 (d, 1H, J=16.5 Hz), 5.28 (d, 1H, J=16.5 Hz), 5.20 (s, 2H), 3.50-3.32 (m, 2H), 3.20-3.00 (m, 2H), 2.00-1.80 (m, 2H), 1.80-1.58 (m, 2H), 1.02 (t, 3H, J=7.2 Hz), 0.98-0.82 (m, 2H), 0.74-0.58 (m, 2H), 0.18 (s, 6H).

MS (m/z, M+1): 588

28. Synthesis of acetic acid (4S)-11-(2-{dimethyl-[3-(3-phenylureido)-propyl]-silanyl}-ethyl)-4-ethyl-3,13-dioxo-3,4,12,13-tetrahydro-1H-2-oxa-6,12a-diaza-dibenzo[b,h]fluoren-4-yl ester (Compound 24)

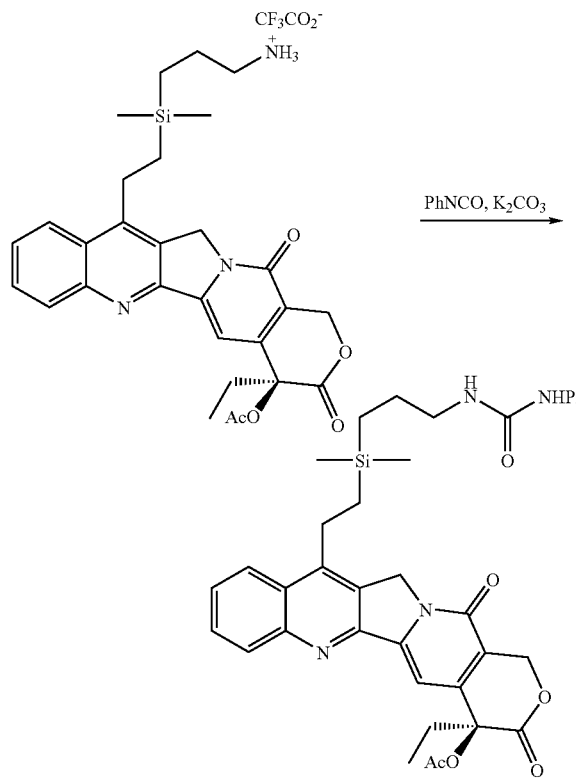

The required product was prepared according to Procedure E, above, using Compound 21 and phenyl isocyanate. The required product was obtained in 50% yield.

$^1$H NMR (300 MHz, δ, CDCl$_3$) 8.25 (d, 1H, J=7.8 Hz), 8.1 (d, 1H, J=8.2 Hz), 7.90-7.60 (m, 3H), 7.44-6.85 (m, 5H), 5.80 (bs, 1H), 5.72 (d, 1H, J=16.7 Hz), 5.44 (d, 1H, J=16.5 Hz), 5.27 (s, 2H), 3.50-3.25 (m, 2H), 3.20-3.00 (m, 2H), 2.40-2.00 (m, 2H), 2.24 (s, 3H), 1.80-1.50 (4H), 1.00 (t, 3H, J=7.5 Hz), 1.00-0.70 (m, 4H), 0.13 (s, 3H), 0.12 (s, 3H).

29. Synthesis of (4S)-1-(3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-propyl)-3-phenylurea (Compound 25)

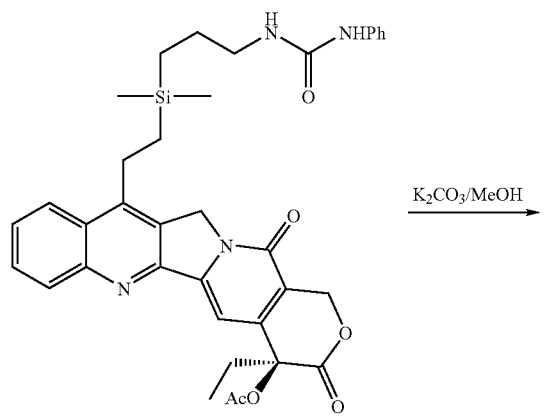

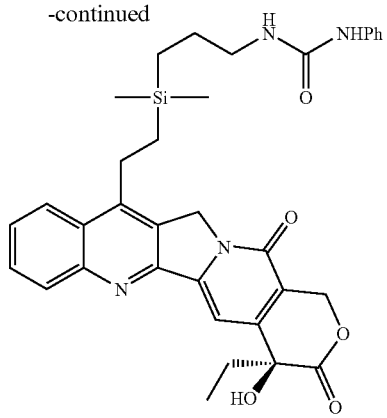

Prepared according to Procedure C, above, using Compound 24, the crude product was purified on a silica gel column using 2% ethanol in dichloromethane to obtain the required product in 80% yield.

$^1$H NMR (300 MHz, δ, DMSO) 8.39 (s, 1H), 8.17 (d, 2H, J=8.7 Hz), 7.84 (t, 1H, J=7.5 Hz), 7.73 (t, 1H, J=7.5 Hz), 7.42-7.25 (m, 3H), 7.17 (t, 2H, J=7.8 Hz), 6.84 (t, 1H, J=7.4 Hz), 6.54 (s, 1H), 6.18 (t, 1H, J=5.4 Hz), 5.44 (s, 2H), 5.33 (s, 2H), 3.25-3.00 (m, 4H), 2.00-1.80 (m, 2H), 1.60-1.40 (m, 2H), 1.05-0.80 (m, 5H), 0.75-0.58 (m, 2H), 0.16 (s, 6H).

MS (m/z, M+1): 611

30. Synthesis of acetic acid (4S)-11-(2-{[3-(3,3-diethylureido)-propyl]-dimethylsilanyl}-ethyl)-4-ethyl-3,13-dioxo-3,4,12,13-tetrahydro-1H-2-oxa-6,12a-diaza-dibenzo[b,h]fluoren-4-yl ester (Compound 26)

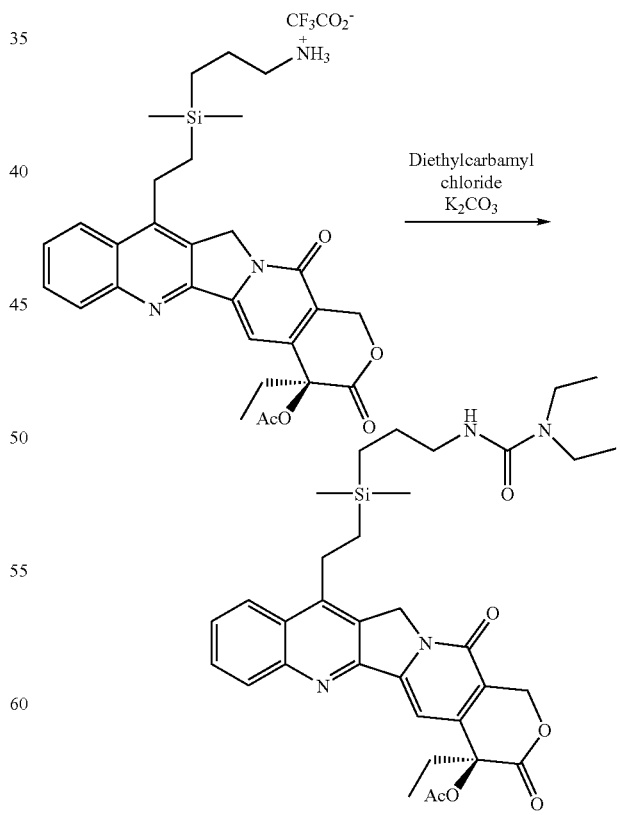

The required product was prepared according to Procedure E, above, using Compound 21 and diethylcarbamyl chloride. The required product was obtained in 70% yield.

¹H NMR (300 MHz, δ, CDCl₃) 8.22 (d, 1H, J=7.5 Hz), 8.05 (d, 1H, J=7.8 Hz), 7.85-7.60 (m, 2H), 7.20 (s, 1H), 5.64 (d, 1H, J=16.5 Hz), 5.40 (d, 1H, J=16.5 Hz), 5.21 (s, 2H), 3.25 (q, 4H, J=7.1 Hz), 3.20-3.00 (m, 2H), 2.40-2.00 (m, 2H), 2.21 (s, 3H), 1.65-1.42 (m, 2H), 1.13 (t, 6H, J=7.2 Hz), 1.05-0.82 (m, 5H), 0.75-0.57 (m, 2H), 0.17 (s, 6H).

31. Synthesis of (4S)-11-diethyl-3-(3-{[2-(4-ethyl-4-hydroxy-3,13-dioxo-3,4,12,13-tetrahydro-1H-oxa-6,12a-diaza-dibenzo[b,h]fluoren-11-yl)-ethyl]-dimethyl-silanyl}-propyl)-urea (Compound 27)

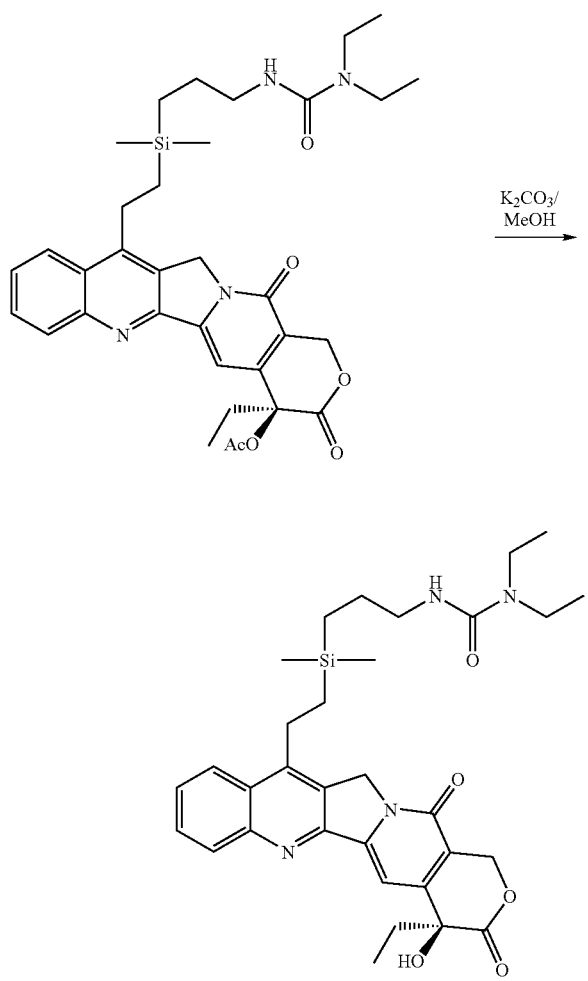

Prepared according to Procedure C, above, using Compound 26, the crude product was purified on a silica gel column using 2% ethanol in dichloromethane to obtain the required product in 76% yield.

¹H NMR (300 MHz, δ, CDCl₃) 8.27 (d, 1H, J=7.5 Hz), 8.05 (d, 1H, J=7.8 Hz), 7.73 (s, 1H), 7.85-7.60 (m, 2H), 5.75 (d, 1H, J=16.5 Hz), 5.31 (d, 1H, J=16.5 Hz), 5.25 (s, 2H), 3.26 (q, 4H, J=7.1 Hz), 3.20-3.00 (m, 2H), 2.00-1.80 (m, 2H), 1.70-1.42 (m, 2H), 1.15 (t, 6H, J=7.2 Hz), 1.05 (t, 3H, J=7.4 Hz), 1.00-0.84 (m, 2H), 0.75-0.58 (m, 2H), 0.18 (s, 6H).

MS (m/z, M+1): 591

32. Synthesis of acetic acid (4S)-11-(2-{[3-(3,3-dimethylureido)-propyl]-dimethylsilanyl}-ethyl)-4-ethyl-3,13-dioxo-3,4,12,13-tetrahydro-1H-2-oxa-6,12a-diaza-dibenzo[b,h]fluoren-4-yl ester (Compound 28)

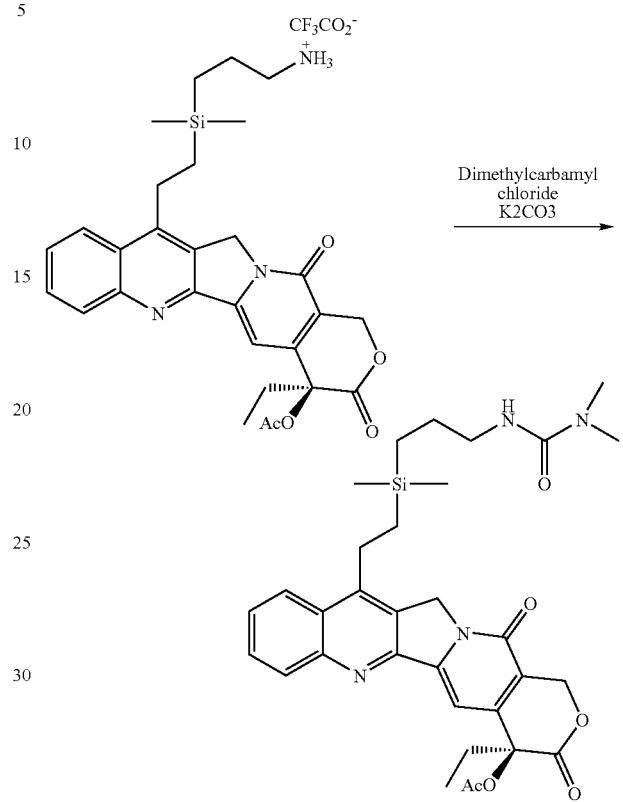

The required product was prepared according to Procedure E, above, using Compound 21 and dimethylcarbamyl chloride. The required product was obtained in 72% yield.

¹H NMR (300 MHz, δ, CDCl₃) 8.21 (d, 1H, J=8.4 Hz), 8.05 (d, 1H, J=8.4 Hz), 7.85-7.60 (m, 2H), 7.21 (s, 1H), 5.65 (d, 1H, J=17.1 Hz), 5.38 (d, 1H, J=17.1 Hz), 5.22 (s, 2H), 4.64 (bs, 1H), 3.30-3.19 (m, 2H), 3.20-3.00 (m, 2H), 2.89 (s, 6H), 2.40-2.00 (m, 2H), 2.20 (s, 3H), 1.65-1.42 (m, 2H), 1.05-0.82 (m, 5H), 0.75-0.58 (m, 2H), 0.16 (s, 6H).

33. Synthesis of (4S)-3-(3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-propyl)-1,1-dimethylurea (Compound 29)

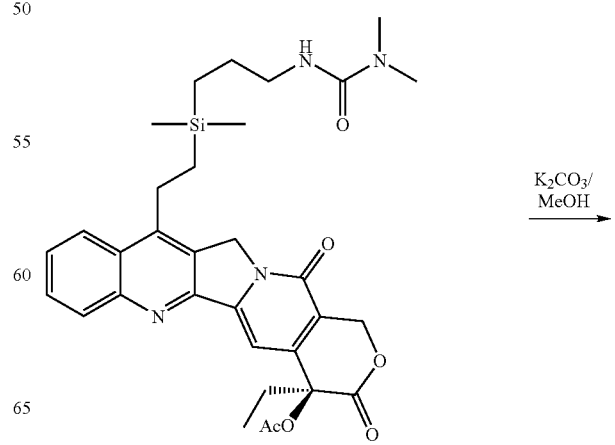

-continued

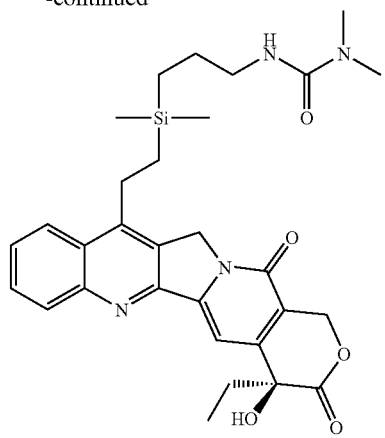

Prepared according to Procedure C, above, using Compound 28, the crude product was purified on a silica gel column using 2% ethanol in dichloromethane to obtain the required product in 71% yield.

$^1$H NMR (300 MHz, δ, CDCl$_3$) 8.25 (d, 1H, J=7.8 Hz), 8.04 (d, 1H, J=7.8 Hz), 7.90-7.60 (m, 1H), 3.34-3.20 (m, 2H), 3.20-3.00 (m, 2H), 2.90 (s, 6H), 2.00-1.78 (m, 2H), 1.70-1.42 (m, 2H), 1.04 (t, 3H, J=7.5 Hz), 1.00-0.82 (m, 2H), 0.75-0.58 (m, 2H), 0.18 (s, 6H).

MS (m/z, M+1): 563

34. Synthesis of (4S)-11-[2-(dimethyl-[1,2,4]triazol-1-ylmethylsilanyl)-ethyl]-4-ethyl-4-hydroxy-1,12-dihydro-4H-2-oxa-6,12a-diaza-dibenzo[b,h]fluorene-3,13-dione (Compound 30)

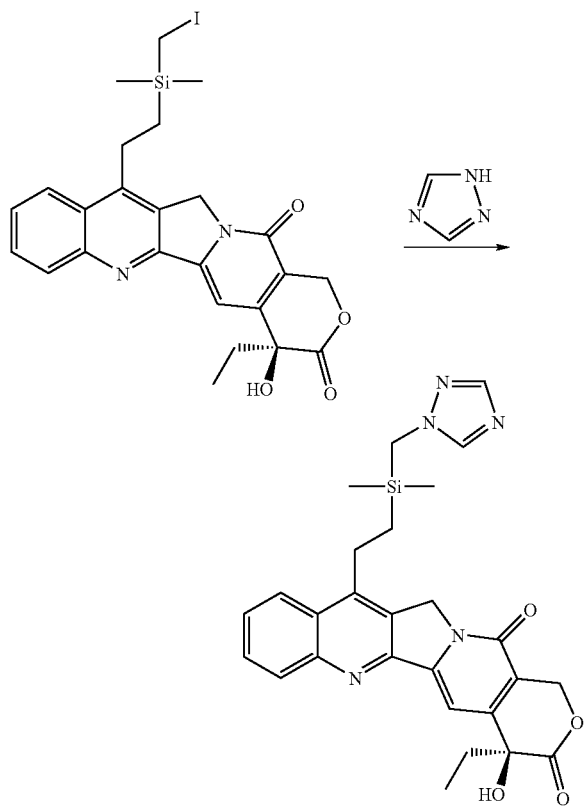

A solution of Compound 4 (60 mg), 1,2,4-triazole (22 mg) and NaHCO$_3$ (26 mg) in dry N,N-dimethylformamide (1 mL) was heated at 70° C. for 5 hours under argon. The N,N-dimethylformamide was removed from the reaction mixture under vacuum and the residue was directly eluted on a silica gel column using 4% ethanol in dichloromethane to obtain the required product in 79% yield (43 mg).

$^1$H NMR (300 MHz, δ, CDCl$_3$) 8.66 (bs, 1H), 8.32 (d, 1H, J=8.1 Hz), 8.22 (s, 1H), 8.09 (d, 1H, J=7.8 Hz), 7.90-7.78 (m, 2H), 7.70 (t, 1H, J=7.2 Hz), 5.71 (d, 1H, J=16.5 Hz), 5.34 (s, 2H), 5.28 (d, 1H, J=16.5 Hz), 4.03 (s, 2H), 3.38-3.18 (m, 2H), 2.00-1.80 (m, 2H), 1.25-1.10 (m, 2H), 1.03 (t, 3H, J=7.4 Hz), 0.32 (s, 3H), 0.31 (s, 3H).

MS (m/z, M+1): 516

35. Synthesis of (4S)-11-{2-[dimethyl-(2-oxo-2H-pyridin-1-ylmethyl)-silanyl]-ethyl}-4-ethyl-4-hydroxy-1,12-dihydro-4H-2-oxa-6,12a-diaza-dibenzo[b,h]fluorene-3,13-dione (Compound 31)

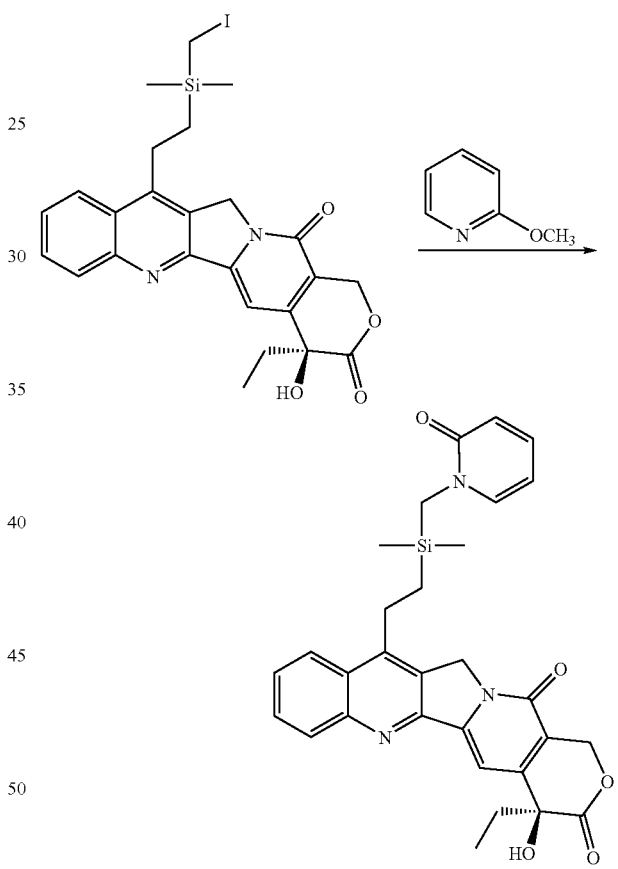

A solution of Compound 4 (60 mg) and 2-methoxypyridine (0.11 mL) in N,N-dimethylformamide (1 mL) was heated at 70° C. for 16 hours. The reaction mixture was concentrated under vacuum and the residue was directly eluted on a silica gel column using 4% ethanol in dichloromethane to obtain the required product in 44% yield (25 mg).

$^1$H NMR (300 MHz, δ, CDCl$_3$) 8.18 (d, 1H, J=8.2 Hz), 8.06 (d, 1H, J=8.3 Hz), 7.82-7.52 (m, 2H), 7.66 (s, 1H), 7.41-7.20 (m, 2H), 6.69 (d, 1H, J=9.3 Hz), 6.30-6.12 (m, 1H), 5.73 (d, 1H, J=16.2 Hz), 5.29 (d, 1H, J=16.2 Hz), 5.17 (s, 2H), 3.80-3.60 (m, 2H), 3.24-3.00 (m, 2H), 2.05-1.78 (m, 2H), 1.12-0.86 (m, 5H), 0.27 (s, 3H), 0.25 (s, 3H). m/z 542 [M+H]$^+$

36. Synthesis of (4S)-11-[2-(dimethyl-pyrrolidin-1-ylmethyl-silanyl)-ethyl]-4-ethyl-4-hydroxy-1,12-dihydro-4H-2-oxa-6,12a-diaza-dibenzo[b,h]fluorene-3,13-dione (Compound 32)

37. Synthesis of (4S)-11-{2-[dimethyl-(1-methyl-1H-imidazol-2-ylsulfanylmethyl)-silanyl]-ethyl}-4-ethyl-4-hydroxy-1,12-dihydro-4H-2-oxa-6,12a-diaza-dibenzo[b,h]fluorene-3,13-dione (Compound 33)

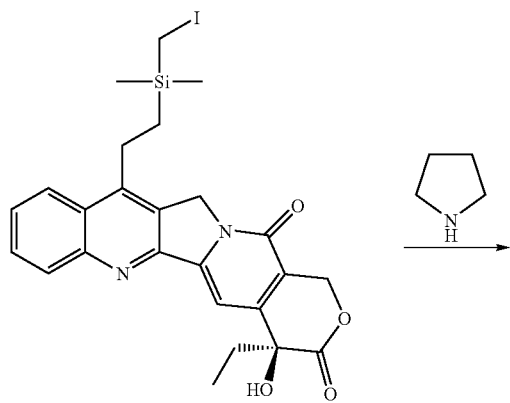

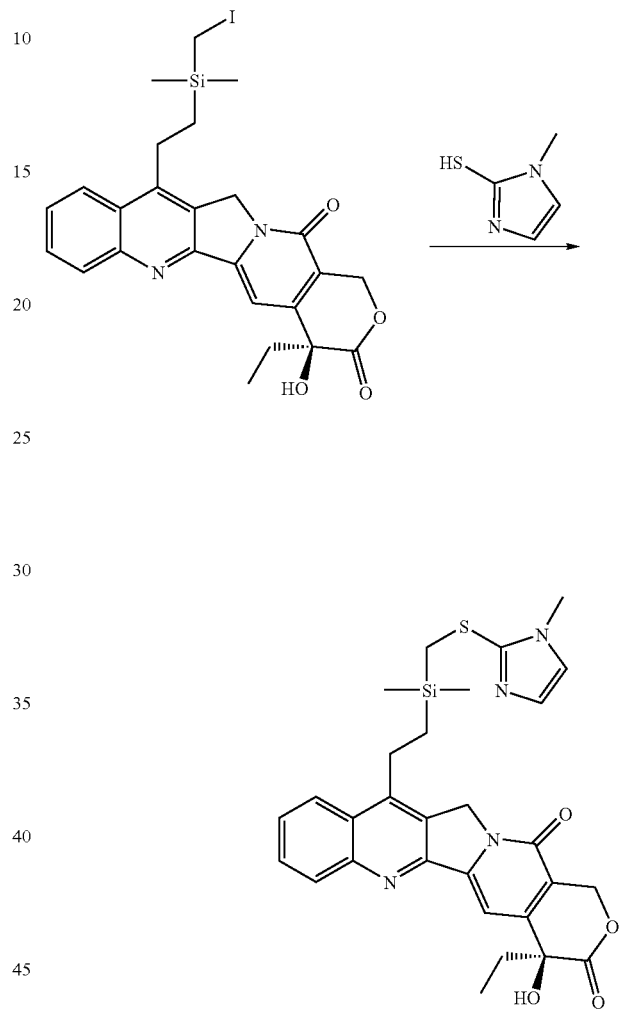

A slurry of Compound 4 (60 mg) and $K_2CO_3$ (43 mg) in deionized water (1 mL) was stirred at room temperature for 30 min. To the resulting reaction mixture, t-BuOH (1 mL) and pyrrolidine (52 µL) were added and heated at 70° C. for 5 hours. The reaction mixture was then concentrated under reduced pressure and the residue was dissolved in acetic acid (10 mL) and stirred at room temperature for 2 hours. The acetic acid solution was concentrated again under vacuum. Finally, the residue was partitioned between chloroform (2×15 mL) and 7% aqueous $NaHCO_3$ solution (5 mL). The collective organic layers were dried, concentrated and purified on a silica gel using 10% ethanol in dichloromethane to afford the required product in 83% yield (45 mg).

$^1$H NMR (300 MHz, δ, $CDCl_3$) 8.24-8.12 (m, 2H), 7.82-7.57 (m, 2H), 7.66 (s, 1H), 5.74 (d, 1H, J=16.5 Hz), 5.27 (d, 1H, J=16.4 Hz), 5.23 (s, 2H), 3.25-3.08 (m, 2H), 2.65 (bs, 4H), 2.26 (s, 2H), 2.00-1.78 (m, 6H), 1.12-0.95 (m, 5H), 0.26 (s, 6H).

MS (m/z, M+1): 518

Prepared according to Procedure F using Compound 4 and 2-mercapto-1-methylimidazole, the crude product was purified on a silica gel column using 3% ethanol in dichloromethane to obtain the pure product in quantitative yields.

$^1$H NMR (300 MHz, δ, $CDCl_3$) 8.20 (d, 1H, J=7.5 Hz), 8.16 (d, 1H, J=8.7 Hz), 7.79 (t, 1H, J=6.9 Hz), 7.77-7.62 (m, 1H), 7.65 (s, 1H), 7.01 (d, 1H, J=1.8 Hz), 5.74 (d, 1H, J=16.2 Hz), 5.40-5.20 (m, 3H), 3.78 (s, 1H), 3.73 (s, 3H), 3.38-3.20 (m, 2H), 3.03 (bs, 2H), 2.00-1.80 (m, 2H), 1.24-1.10 (m, 2H), 1.04 (t, 3H, J=7.4 Hz), 0.35 (s, 6H).

MS (m/z, M+1): 561

38. Synthesis of (4S)-11-{2-[(4,5-dihydro-thiazol-2-ylsulfanylmethyl)-dimethylsilanyl]-ethyl}-4-ethyl-4-hydroxy-1,12-dihydro-4H-2-oxa-6,12a-diaza-dibenzo[b,h]fluorene-3,13-dione (Compound 34)

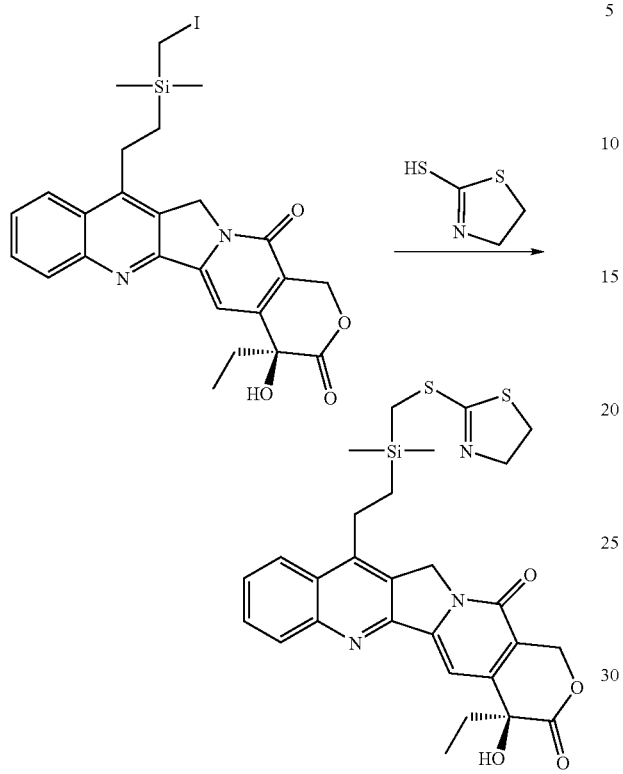

Prepared according to Procedure F using Compound 4 and 2-mercaptothiazoline, the crude product was purified on a silica gel column using 3% ethanol in dichloromethane to obtain the pure product in 65% yields.

$^1$H NMR (300 MHz, δ, CDCl$_3$) 8.20 (d, 1H, J=7.8 Hz), 8.09 (d, 1H, J=7.5 Hz), 7.84-7.60 (m, 2H), 7.66 (s, 1H), 5.74 (d, 1H, J=16.5 Hz), 5.40-5.20 (m, 3H), 4.37 (t, 2H, J=8.0 Hz), 3.61 (t, 2H, J=8.1 Hz), 3.30-3.10 (m, 2H), 2.86 (bs, 2H), 2.00-1.80 (m, 2H), 1.20-1.08 (m, 2H), 1.04 (t, 3H, J=7.5 Hz), 0.33 (s, 6H).

MS (m/z, M+1): 566

39. Synthesis of (4S)-4-ethyl-4-hydroxy-11-{2-[(2-hydroxy-ethylsulfanylmethyl)-dimethyl-silanyl]-ethyl}-1,12-dihydro-4H-2-oxa-6,12a-diaza-dibenzo[b,h]fluorene-3,13-dione (Compound 35)

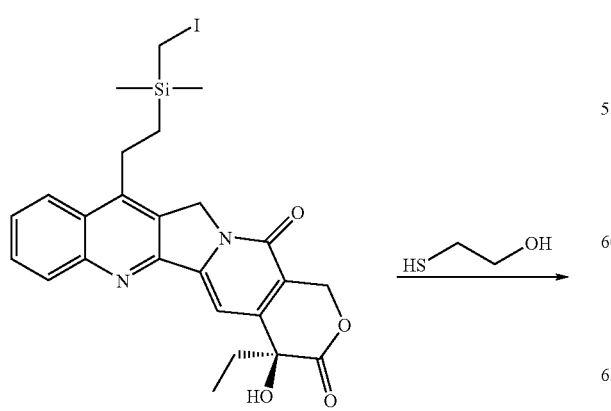

Prepared according to Procedure F using Compound 4 and 2-mercaptoethanol, the crude product was purified on a silica gel column using 3% ethanol in dichloromethane to obtain the pure product in 83% yields.

$^1$H NMR (300 MHz, δ, CDCl$_3$) 8.30 (d, 1H, J=8.4 Hz), 8.10 (d, 1H, J=7.8 Hz), 7.84 (s, 1H), 7.84-7.74 (m, 1H), 7.68 (t, 1H, J=7.2 Hz), 5.72 (d, 1H, J=16.5 Hz), 5.42 (s, 2H), 5.28 (d, 1H, J=16.2 Hz), 3.92 (t, 2H, J=5.7 Hz), 3.34-3.18 (m, 2H), 2.87 (t, 2H, J=5.6 Hz), 2.06 (dd, 2H, J=12.3, 15.0 Hz), 2.00-1.80 (m, 2H), 1.20-0.98 (m, 5H), 0.27 (s, 3H), 0.25 (s, 3H).

MS (m/z, M+1): 525

40. Synthesis of (4S)-11-[2-(azidomethyldimethylsilanyl)-ethyl]-4-ethyl-4-hydroxy-1,12-dihydro-4H-2-oxa-6,12a-diaza-dibenzo[b,h]fluorene-3,13-dione (Compound 36)

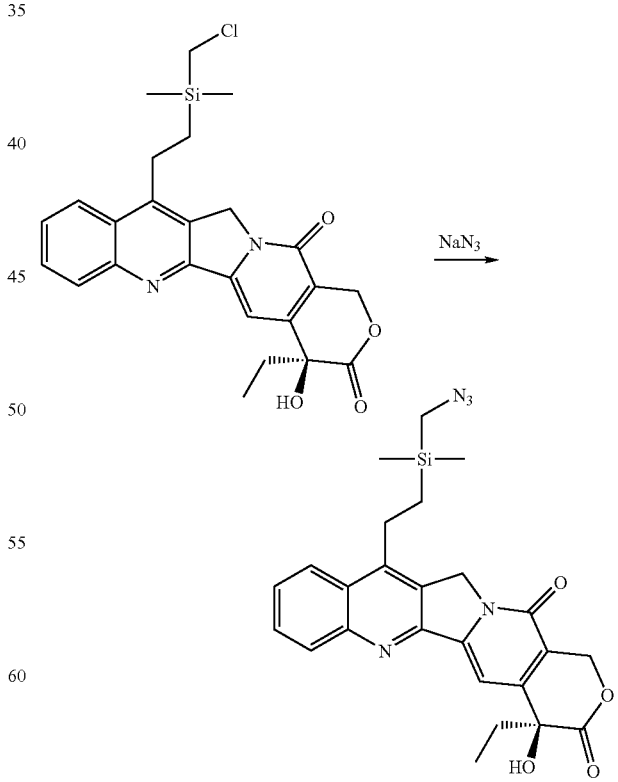

A slurry of Compound 3 (950 mg) and sodium azide (255 mg) in dry N,N-dimethylformamide (10 mL) was heated at 70° C. for 3 hours under argon. The N,N-dimethylformamide was removed from the reaction mixture under vacuum and directly eluted on a silica gel using 2% ethanol in dichloromethane to afford the required product in 83% yield (800 mg).

$^1$H NMR (300 MHz, δ, CDCl$_3$) 8.28 (d, 1H, J=7.8 Hz), 8.08 (d, 1H, J=8.4 Hz), 7.84-7.60 (m, 2H), 7.73 (s, 1H), 5.76 (d, 1H, J=16.5 Hz), 5.31 (d, 1H, J=16.5 Hz), 5.26 (s, 2H), 3.22-3.06 (m, 2H), 3.00 (s, 2H), 2.00-1.80 (m, 2H), 1.20-0.96 (m, 5H), 0.29 (s, 6H).

41. Synthesis of (4S)-4-chloro-N-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)-benzenesulfonamide (Compound 37)

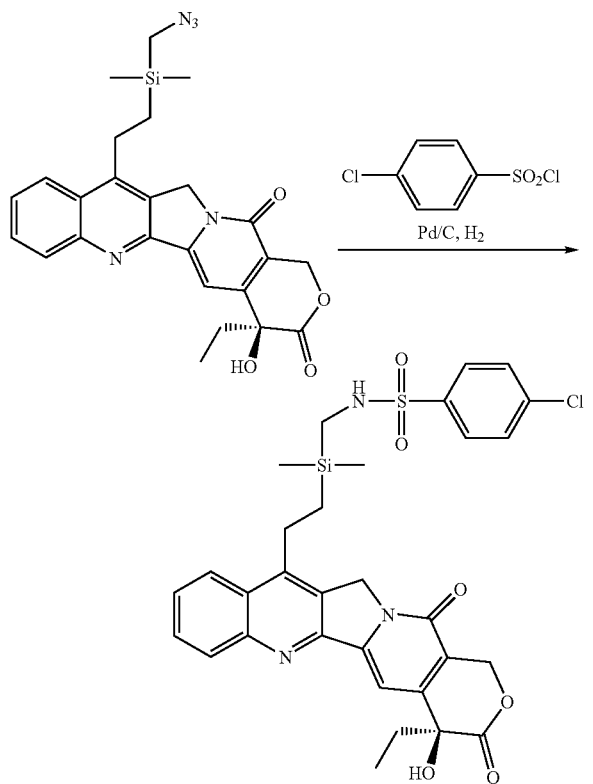

A slurry of Compound 36 (85 mg) and Pd/C (16 mg, 10%) in a mixture of methanol (4 mL) and ethyl acetate (2 mL) containing trifluoroacetic acid (0.1 mL) was hydrogenated under balloon pressure of hydrogen for 3 days. Solvents were dried off under vacuum and the resulting residue was taken up in dry tetrahydrofuran (2 mL) and K$_2$CO$_3$ (48 mg) and 4-chlorobenzenesulfonyl chloride (44 mg) were added and stirred at room temperature for 1 hour. The reaction mixture was concentrated again under reduced pressure and the residue was purified on a silica gel column using 2% ethanol in dichloromethane to afford the required product in 53% yield (59 mg).

$^1$H NMR (300 MHz, δ, CDCl$_3$) 8.20 (d, 1H, J=7.8 Hz), 8.07 (d, 1H, J=8.2 Hz), 7.88-7.50 (m, 2H), 7.82 (d, 2H, J=8.7 Hz), 7.63 (s, 1H), 7.50 (d, 2H, J=8.7 Hz), 5.71 (d, 1H, J=16.5 Hz), 5.26 (d, 1H, J=16.5 Hz), 5.19 (s, 2H), 4.70 (m, 1H), 3.22-3.00 (m, 2H), 2.50 (d, 2H), 2.00-1.80 (m, 2H), 1.10-0.95 (m, 5H), 0.22 (s, 3H), 0.21 (s, 3H).

42. Synthesis of acetic acid (4S)-11-[2-(azidomethyldimethylsilanyl)-ethyl]-4-ethyl-3,13-dioxo-3,4,12,13-tetrahydro-1H-2-oxa-6,12a-diaza-dibenzo[b,h]fluoren-4-yl ester (Compound 38)

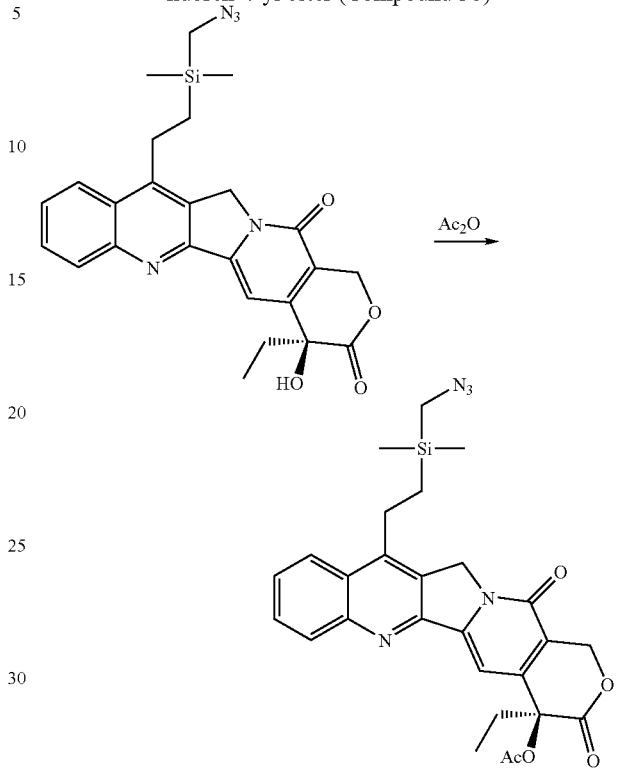

Prepared according to Procedure B using Compound 36, the crude product was purified on a silica gel column using 1% ethanol in dichloromethane to obtain the pure product in 97% yield.

$^1$H NMR (300 MHz, δ, CDCl$_3$) 8.28 (d, 1H, J=7.8 Hz), 8.10 (d, 1H, J=8.4 Hz), 7.90-7.60 (m, 2H), 7.28 (s, 1H), 5.68 (d, 1H, J=16.5 Hz), 5.40 (d, 1H, J=16.5 Hz), 5.25 (d, 2H, J=0.9 Hz), 3.24-3.08 (m, 2H), 3.00 (s, 2H), 2.40-2.04 (m, 2H), 2.22 (s, 3H), 1.20-0.96 (m, 5H), 0.29 (s, 6H).

43. Synthesis of trifluoroacetate (4S)-{[2-(4-acetoxy-4-ethyl-3,13-dioxo-3,4,12,13-tetrahydro-1H-2-oxa-6,12a-diaza-dibenzo[b,h]fluoren-11-yl)-ethyl]-dimethylsilanyl}-methylammonium (Compound 39)

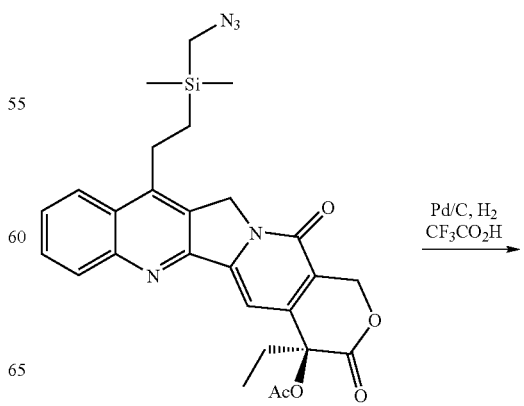

-continued

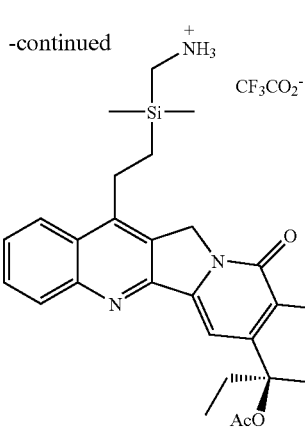

Prepared according to Procedure D using Compound 38, the required product was obtained in quantitative yields.

44. Synthesis of acetic acid (4S)-11-(2-{dimethyl-[(3-phenylureido)-methyl]-silanyl}-ethyl)-4-ethyl-3,13-dioxo-3,4,12,13-tetrahydro-1H-2-oxa-6,12a-diaza-dibenzo[b,h]fluoren-4-yl ester (Compound 40)

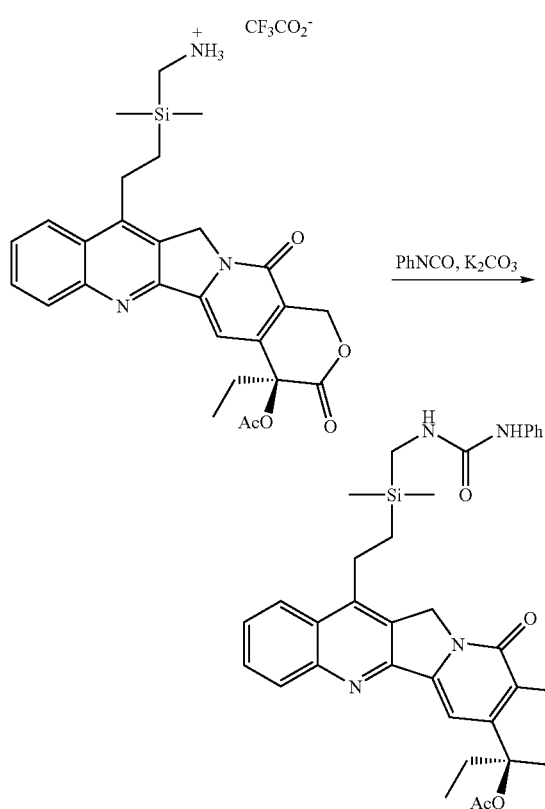

The required product was prepared according to Procedure E, above, using Compound 39 and phenyl isocyanate. The required product was obtained in 43% yield.

$^1$H NMR (300 MHz, δ, DMSO) 8.22 (d, 1H, J=8.2 Hz), 8.07 (d, 1H, J=8.4 Hz), 7.79 (t, 1H, J=7.5 Hz), 7.62 (t, 1H, J=7.2 Hz), 7.40-6.90 (m, 6H), 5.66 (d, 1H, J=16.5 Hz), 5.38 (d, 1H, J=16.5 Hz), 5.30-5.10 (m, 2H), 5.10 (bs, 1H), 3.22-3.06 (m, 2H), 2.89 (bs, 2H), 2.40-2.00 (m, 2H), 2.19 (s, 3H), 1.10-0.90 (m, 5H), 0.22 (s, 3H), 0.21 (s, 3H).

45. Synthesis of (4S)-1-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)-3-phenylurea (Compound 41)

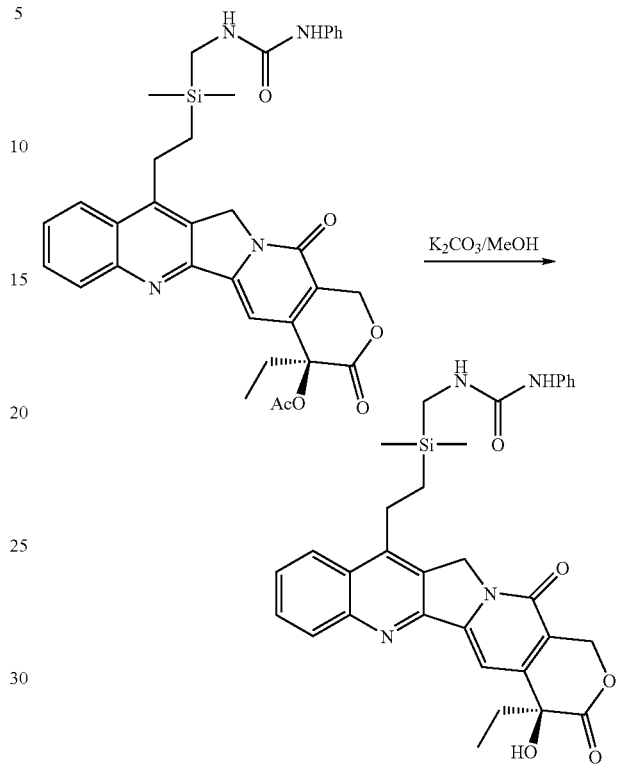

Prepared according to Procedure C using Compound 40, the crude product was purified on a silica gel column using 2% ethanol in dichloromethane to obtain the required product in 68% yield.

$^1$H NMR (300 MHz, δ, DMSO) 8.40 (s, 1H), 8.23 (d, 1H, J=8.1 Hz), 8.15 (d, 1H, J=8.7 Hz), 7.81 (t, 1H, J=7.4 Hz), 7.60 (t, 1H, J=7.7 Hz), 7.41 (d, 2H, J=7.5 Hz), 7.32 (s, 1H), 7.21 (t, 2H, J=8.0 Hz), 6.87 (t, 1H, J=7.2 Hz), 6.53 (s, 1H), 6.04 (t, 1H, J=5.1 Hz), 5.44 (s, 2H), 5.35 (s, 2H), 3.30-3.10 (m, 2H), 2.75 (d, 2H, J=5.1 Hz), 2.00-1.80 (m, 2H), 1.10-0.90 (m, 2H), 0.88 (t, 3H, J=7.2 Hz), 0.22 (s, 6H).

46. Synthesis of acetic acid (4S)-11-{2-[(3,3-diethyl-ureidomethyl)-dimethyl-silanyl]-ethyl}-4-ethyl-3,13-dioxo-3,4,12,13-tetrahydro-1H-2-oxa-6,12a-diaza-dibenzo[b,h]fluoren-4-yl ester (Compound 42)

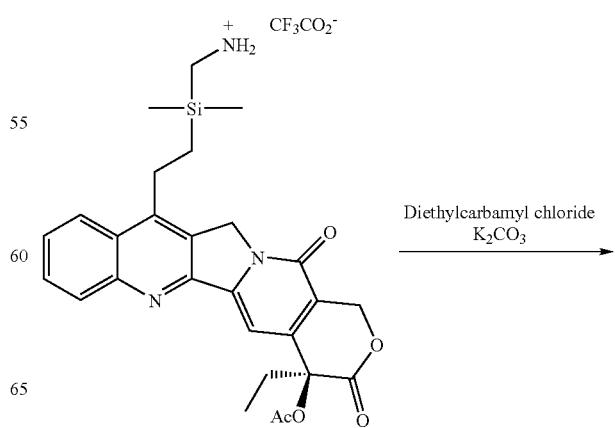

-continued

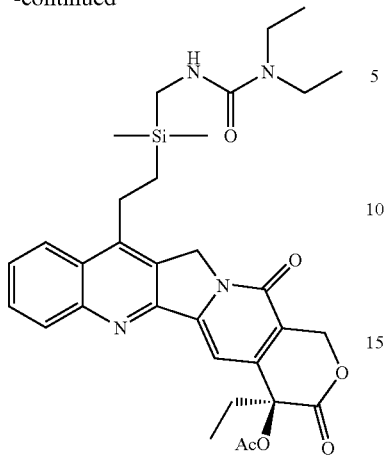

The required product was prepared according to Procedure E, above, using Compound 39 and diethylcarbamyl chloride. The required product was obtained in 55% yield.

¹H NMR (300 MHz, δ, CDCl₃) 8.22 (d, 1H, J=8.4 Hz), 8.15 (d, 1H, J=8.4 Hz), 7.83-7.60 (m, 2H), 7.26 (s, 1H), 5.65 (d, 1H, J=16.5 Hz), 5.40 (d, 1H, J=16.5 Hz), 5.23 (s, 2H), 3.29 (q, 4H, J=7.2 Hz), 3.25-3.10 (m, 2H), 2.90 (d, 2H), 2.40-2.00 (m, 2H), 2.21 (s, 3H), 1.14 (t, 6H, J=7.1 Hz), 1.08-0.88 (m, 5H), 0.23 (s, 6H).

47. Synthesis of (4S)-1,1-diethyl-3-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)-urea (Compound 43)

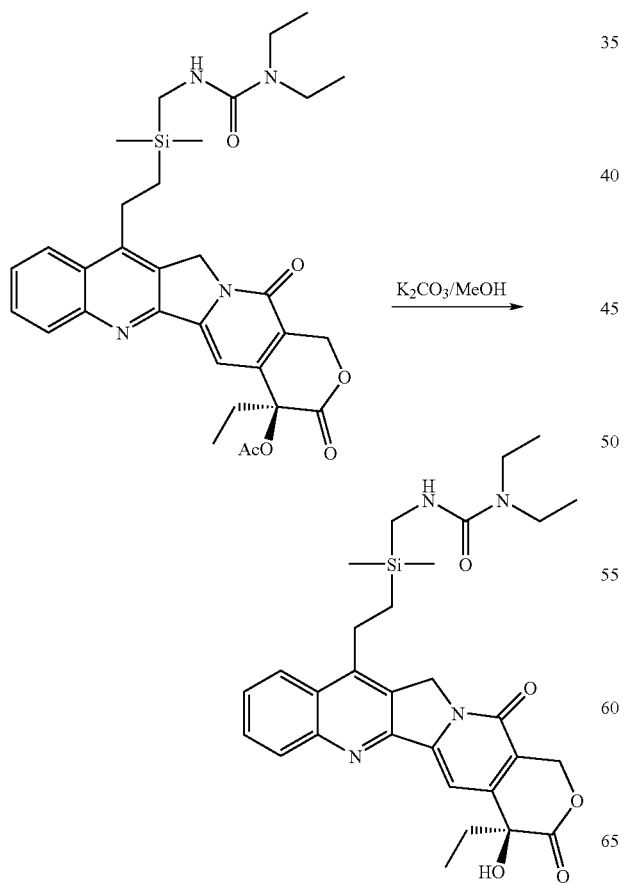

Prepared according to Procedure C using Compound 42, the crude product was purified on a silica gel column using 2% ethanol in dichloromethane to obtain the required product in 86% yield.

¹H NMR (300 MHz, δ, CDCl₃) 8.26 (d, 1H, J=8.4 Hz), 8.14 (d, 1H, J=8.7 Hz), 7.85-7.60 (m, 2H), 7.72 (s, 1H), 5.76 (d, 1H, J=16.5 Hz), 5.31 (d, 1H, J=16.5 Hz), 5.26 (s, 2H), 3.29 (q, 4H, J=7.2 Hz), 3.28-3.08 (m, 2H), 2.91 (bs, 2H), 2.00-1.80 (m, 2H), 1.18 (t, 6H, J=7.2 Hz), 1.05 (t, 3H, J=7.4 Hz), 1.10-0.92 (m, 2H), 0.25 (s, 6H).

48. Synthesis of acetic acid (4S)-11-{2-[(3,3-dimethylureidomethyl)-dimethylsilanyl]-ethyl}-4-ethyl-3,13-dioxo-3,4,12,13-tetrahydro-1H-2-oxa-6,12a-diaza-dibenzo[b,h]fluoren-4-yl ester (Compound 44)

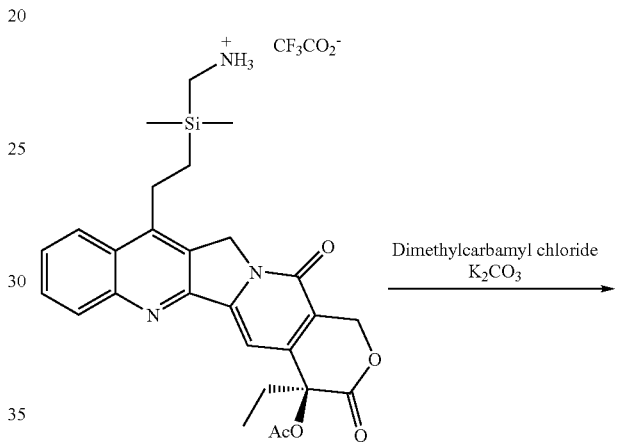

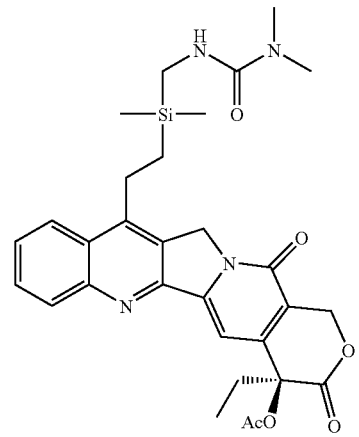

The required product was prepared according to Procedure E, above, using Compound 39 and dimethylcarbamyl chloride. The required product was obtained in 72% yield.

¹H NMR (300 MHz, δ, CDCl₃) 8.30-8.20 (m, 1H), 8.15 (d, 1H, J=8.1 Hz), 7.85-7.60 (m, 2H), 5.66 (d, 1H, J=16.5 Hz), 5.40 (d, 1H, J=16.5 Hz), 5.24 (s, 2H), 4.30-4.18 (m, 1H), 3.26-3.12 (m, 2H), 2.95 (s, 6H), 2.92-2.80 (m, 2H), 2.38-2.02 (m, 2H), 2.23 (s, 3H), 1.10-0.86 (m, 5H), 0.24 (s, 6H).

49. Synthesis of (4S)-3-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)-1,1-dimethyl-urea (Compound 45)

50. Synthesis of (4S)-4-Ethyl-4-hydroxy-11-[2-(hydroxydimethylsilanyl)-ethyl]-1,12-dihydro-4H-2-oxa-6,12a-diaza-dibenzo[b,h]fluorene-3,13-dione (Compound 46)

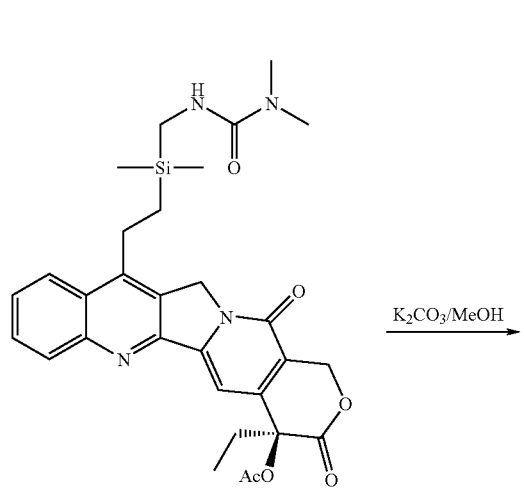

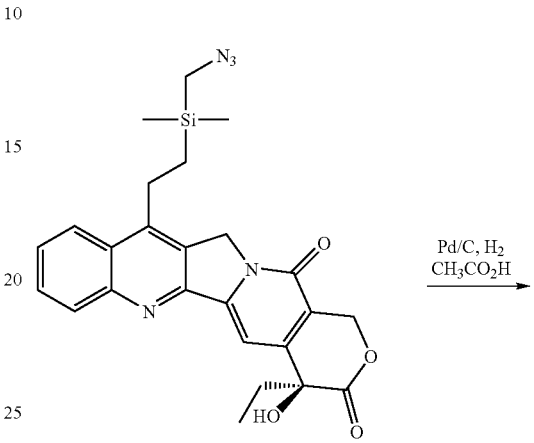

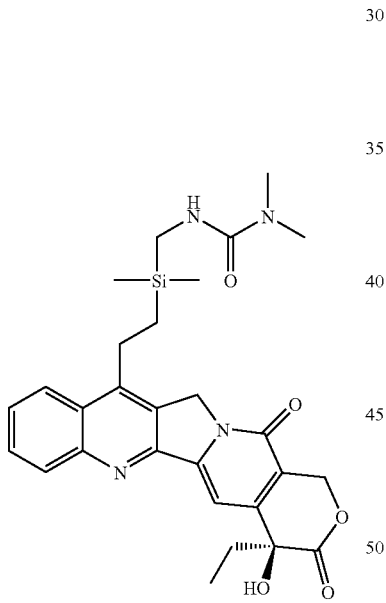

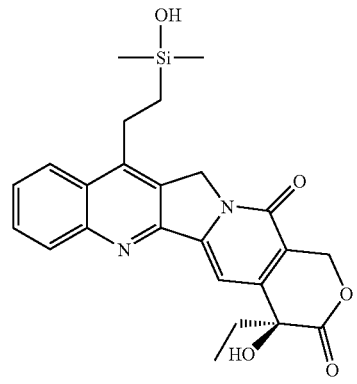

Prepared according to Procedure C using Compound 44, the crude product was purified on a silica gel column using 2% ethanol in dichloromethane to obtain the required product in 86% yield.

$^1$H NMR (300 MHz, δ, CDCl$_3$) 8.28 (d, 1H, J=8.4 Hz), 8.14 (d, 1H, J=8.4 Hz), 7.85-7.60 (m, 3H), 5.75 (d, 1H, J=16.5 Hz), 5.30 (d, 1H, J=16.5 Hz), 5.26 (s, 2H), 3.26-3.06 (m, 2H), 2.95 (s, 6H), 2.93-2.80 (m, 2H), 2.00-1.80 (m, 2H), 1.10-0.92 (m, 5H), 0.24 (s, 6H). m/z 535 [M+H]$^+$

Preparation according to Procedure D using Compound 36 and (5:1) methanol-acetic acid mixture, instead of TFA, afforded the required product in 60% yield.

$^1$H NMR (300 MHz, δ, CDCl$_3$) 8.19 (d, 1H, J=8.7 Hz), 8.09 (d, 1H, J=8.1 Hz), 7.77 (t, 1H, J=7.7 Hz), 7.69 (s, 1H), 7.65 (t, 1H, J=7.7 Hz), 5.73 (d, 1H, J=16.2 Hz), 5.29 (d, 1H, J=16.5 Hz), 5.28 (s, 2H), 3.30-3.10 (m, 2H), 2.02-1.75 (m, 2H), 1.20-0.85 (m, 5H), 0.28 (s, 6H).

MS (m/z, M+1): 451

Synthesis of Compound 47-Compound 50

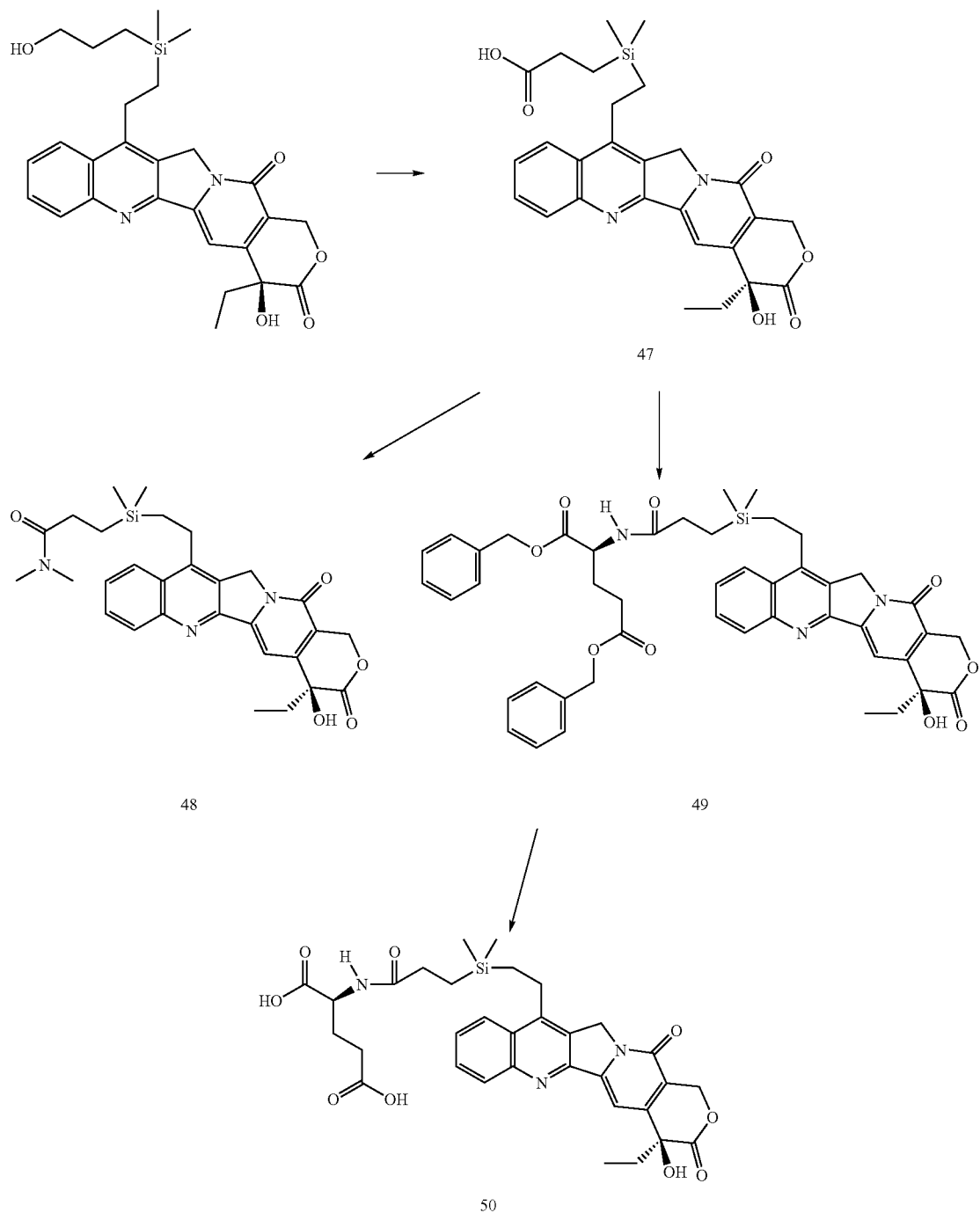

51. Preparation of 3-{[2-(4-Ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propionic acid (Compound 47)

A solution of 7-[2'-(3''-hydroxyl)propyldimethyl silanyl] ethyl camptothecin (110 mg, 0.23 mmol) in 40% sulfuric acid (2 ml) was cooled at ice bath. A solution of chromium trioxide (92 mg, 0.92 mmol) in 40% sulfuric acid (1 ml) was added. The resulted solution (green color) was stirred at room temperature for 16 hours. The reaction was quenched with ice (20 g) and extracted with methanol/chloroform (10/90). The combined organic extracts were dried over anhydrous sodium sulfate, filtrated through silica gel, and concentrated by rotary evaporation. Purification by radial preparative-layer chromatography (methanol/chloroform; 2/98 v/v) provided 100 mg of Compound 47 as a yellow solid. Exact mass m/z calcd for $C_{27}H_{31}N_2O_6Si^+$ 507.194591, found 507.19617.

52. Preparation of 3-{[2-(4-Ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-N,N-dimethyl-propionamide (Compound 48)

To a solution of Compound 47 (1 ml) was added 1-(3-dimethylaminopropyl)-3-ethylcarbodiimide hydrochloride (19 mg, 0.099 mmol) and 1-hydroxybenzotriazole (catalytic amount). Dimethylamine (0.04 ml, M=2 in tetrahydrofuran) and diisopropylethylamine (0.1 ml) were added to the above solution at ice bath. The resulted solution was stirred at room temperature for 3 days. The reaction was quenched with 1 N HCl and extracted with dichloromethane. The combined organic extracts were dried over anhydrous sodium sulfate, filtrated through silica gel, and concentrated by rotary evaporation. Purification by radial preparative-layer chromatography (ethyl acetate/hexanes 50/50 to methanol/chloroform 2/98) provided 12 mg of Compound 48 as a yellow solid.

$^1$H NMR (300 MHz, CDCl$_3$) δ 8.16 (d, 1H, J=7.5 Hz), 8.00 (d, 1H, J=8.1 Hz), 7.75-7.70 (m, 1H), 7.62-7.57 (m, 2H), 5.69 (d, 1H, J=16.5 Hz), 5.24 (d, 1H, J=16.5 Hz), 5.17 (s, 2H), 3.73 (s, 1H), 3.15-3.02 (m, 2H), 2.96 (s, 3H), 2.91 (s, 3H), 2.35-2.27 (m, 2H), 1.88-1.74 (m, 2H,), 1.00-0.92 (m, 7H), 0.13 (s, 6H).

53. Preparation of 2-(3-{[2-(4-Ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propionylamino)-pentanedioic acid dibenzyl ester (Compound 49)

To a solution of Compound 47 (150 mg, 0.30 mmol) in N,N-dimethylformamide (5 ml) was added 1-(3-dimethylaminopropyl)-3-ethylcarbodiimide hydrochloride (170 mg, 0.89 mmol), 1-hydroxybenzotriazole (catalytical amount), L-glutamate (215 mg, 0.59 mmol) and diisopropylethylamine (1 ml). The resulted solution was stirred at room temperature for 3 days. To the reaction mixture was added 20 ml of dichloromethane, washed with 1 N HCl (3×10 ml) and water (20 ml). The combined organic extracts were dried over anhydrous sodium sulfate, filtrated through silica gel, and concentrated by rotary evaporation. Purification by radial preparative-layer chromatography (ethyl acetate/hexanes 50/50 to methanol/chloroform 2/98 v/v) provided Compound 49 as a yellow solid.

$^1$H NMR (300 MHz, CDCl$_3$) δ 8.25 (d, 1H, J=8.4 Hz), 8.05 (d, 1H, J=8.1 Hz), 7.82-7.77 (m, 1H), 7.70-7.64 (m, 2H), 7.37-7.27 (m, 10H), 6.35 (d, 1H, J=7.8 Hz), 5.73 (d, 1H, J=16.2 Hz), 5.28 (d, 1H, J=16.2 Hz), 5.22 (s, 2H), 5.13 (s, 2H), 5.07 (s, 2H), 4.74-4.64 (m, 1H), 3.79 (s, 1H), 3.15-3.02 (m, 2H), 2.55-1.98 (m, 6H), 1.98-1.84 (m, 2H,), 1.05-0.92 (m, 7H), 0.185 (d, 6H, J=1.2 Hz).

54. Preparation of 2-(3-{[2-(4-Ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propionylamino)-pentanedioic acid (Compound 50)

To a solution of Compound 49 (25 mg) in dimethoxyethane (1 ml) and ethanol (1 ml) was added 10% palladium on charcoal (10 mg). The mixture was stirred under hydrogen balloon pressure for 16 hours at room temperature. The resulted mixture was filtrated through Celite and the solvents were removed by rotary evaporation. The residue was purified by prepared TLC plate, eluting with methanol/dichloromethane (50/50), to afford Compound 50 as a yellow solid.

$^1$H NMR (300 MHz, DMSO) δ8.21-8.15 (m, 2H), 7.85 (t, 1H, J=7.2 Hz), 7.54 (t, 1H, J=7.2 Hz), 7.53 (d, 1H, J=7.5 Hz), 7.33 (s, 1H), 6.53 (s, 1H), 5.44 (s, 2H), 5.34 (s, 2H), 4.18-4.11 (m, 1H), 3.18-3.12 (m, 2H), 2.48-1.47 (m, 8H), 0.95-0.86 (m, 7H), 0.14 (s, 6 Hz); MS (m/z, M+1) 636.5.

55. Synthesis of 11-{2-[Dimethyl-(3-triethylsilanyloxy-propyl)-silanyl]-ethyl}-4-ethyl-4-hydroxy-1,12-dihydro-4H-2-oxa-6,12a-diaza-dibenzo[b,h]fluorene-3,13-dione (Compound 51)

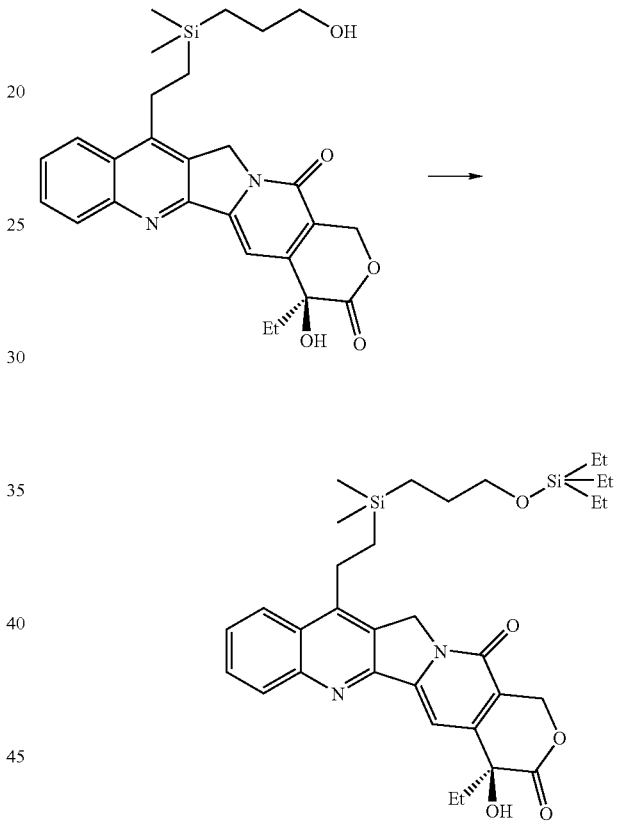

To a solution of 7-[2-(3-hydroxypropyldimethylsilanyl)] ethylcamptothecin (986 mg, 2 mmol) and pyridine (8.1 mL, 100 mmol) in dichloromethane (20 mL) at −78° C. was added chlorotriethylsilane (1.01 mL, 6 mmol) dropwise. The resulting mixture was stirred for 2 hours at −78° C. The reaction was quenched with saturated sodium bicarbonate solution, and aqueous layer was extracted with dichloromethane. The organic layer was separated, dried over sodium sulfate and concentrated to afford yellow oil, which was purified by column chromatographer to afford the pure product (Yield: 90%).

$^1$H NMR (300 MHz, CDCl$_3$): δ 0.18 (s, 6H), 0.64 (m, 8H), 0.96 (m, 11H), 1.05 (t, J=7.5 Hz, 3H), 1.91 (m, 2H), 1.59 (m, 2H), 3.12 (m, 2H), 3.60 (t, J=6.9 Hz, 2H), 3.72 (s, 1H), 5.24 (s, 2H), 5.33 (d, J=15.5 Hz, 1H), 5.79 (d, J=15.5 Hz, 1H), 7.66 (m, 2H), 7.81 (m, 1H), 8.05 (d, J=7.5 Hz, 1H), 8.24 (d, J=8.7 Hz, 1H).

56. Synthesis of Carbonic acid benzyl ester 11-{2-[dimethyl-(3-triethylsilanyloxy-propyl)-silanyl]-ethyl}-4-ethyl-3,13-dioxo-3,4,12,13-tetrahydro-1H-2-oxa-6,12a-diaza-dibenzo[b,h]fluoren-4-yl ester (Compound 52)

57. Synthesis of Carbonic acid benzyl ester 4-ethyl-11-{2-[(3-hydroxy-propyl)-dimethyl-silanyl]-ethyl}-3,13-dioxo-3,4,12,13-tetrahydro-1H-2-oxa-6,12a-diaza-dibenzo[b,h]fluoren-4-yl ester (Compound 53)

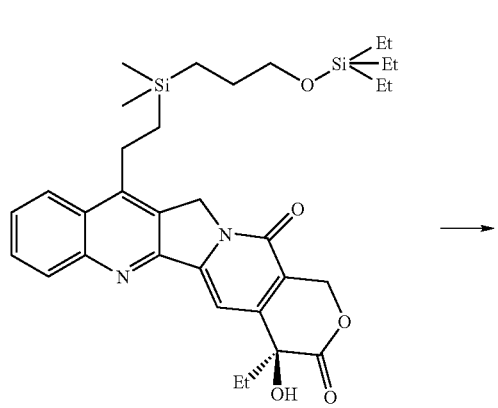

To a solution of Compound 51 (1.21 g, 2 mmol), 4-dimethylaminopyridine (244 mg, 2 mmol) and pyridine (1.62 mL, 20 mmol) in dichloromethane (20 mL) at −10° C. was added phosgene (20% in toluene, 2.10 mL, 4 mmol) dropwise. The resulting mixture was stirred for 15 minutes at −10° C. Benzyl alcohol (0.83 mL, 8 mmol) was added and the resulting mixture was stirred at 21° C. for 2 hours. The reaction was quenched with saturated sodium bicarbonate solution, and aqueous layer was extracted with dichloromethane. The combined organic layers were dried over sodium sulfate and concentrated to afford yellow oil, which was chromatographed to give the desired product (Yield: 47%).

$^1$H NMR (300 MHz, CDCl$_3$): δ 0.18 (s, 6H), 0.64 (m, 8H), 0.97 (m, 14H), 1.59 (m, 2H), 2.20 (m, 2H), 3.12 (m, 2H), 3.61 (t, J=6.9 Hz, 2H), 5.14 (m, 2H), 5.24 (s, 2H), 5.40 (d, J=17.1 Hz, 1H), 5.72 (d, J=17.1 Hz, 1H), 7.30 (m, 6H), 7.69 (t, J=6.0 Hz, 1H), 7.82 (t, J=8.4 Hz, 1H), 8.05 (d, J=7.8 Hz, 1H), 8.24 (d, J=8.4 Hz, 1H).

A mixture of Compound 52 (1.70 g, 2.3 mmol), hydrofluoric acid (48% in water, 1.8 mL, 46 mmol), and pyridine (4.5 mL, 55 mmol) in 20 mL of acetonitrile was stirred at 21° C. for 14 hours. The reaction was quenched with saturated sodium bicarbonate solution, and aqueous layer was extracted with dichloromethane. The combined organic layers were dried over sodium sulfate and concentrated to afford yellow oil, which was chromatographed to give the desired product (Yield: 48%).

$^1$H NMR (300 MHz, CDCl$_3$): δ 0.19 (s, 6H), 0.72 (m, 2H), 0.97 (m, 5H), 1.65 (m, 2H), 2.22 (m, 2H), 3.15 (m, 2H), 3.68 (m, 2H), 5.14 (m, 2H), 5.25 (s, 2H), 5.40 (d, J=17.1 Hz, 1H), 5.69 (d, J=17.1 Hz, 1H), 7.30 (m, 6H), 7.69 (t, J=6.0 Hz, 1H), 7.82 (t, J=8.4 Hz, 1H), 8.05 (d, J=7.8 Hz, 1H), 8.24 (d, J=8.4 Hz, 1H).

58. Synthesis of Benzoic acid 3-{[2-(4-benzyloxy-carbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 54)

59. Synthesis of Benzoic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 55)

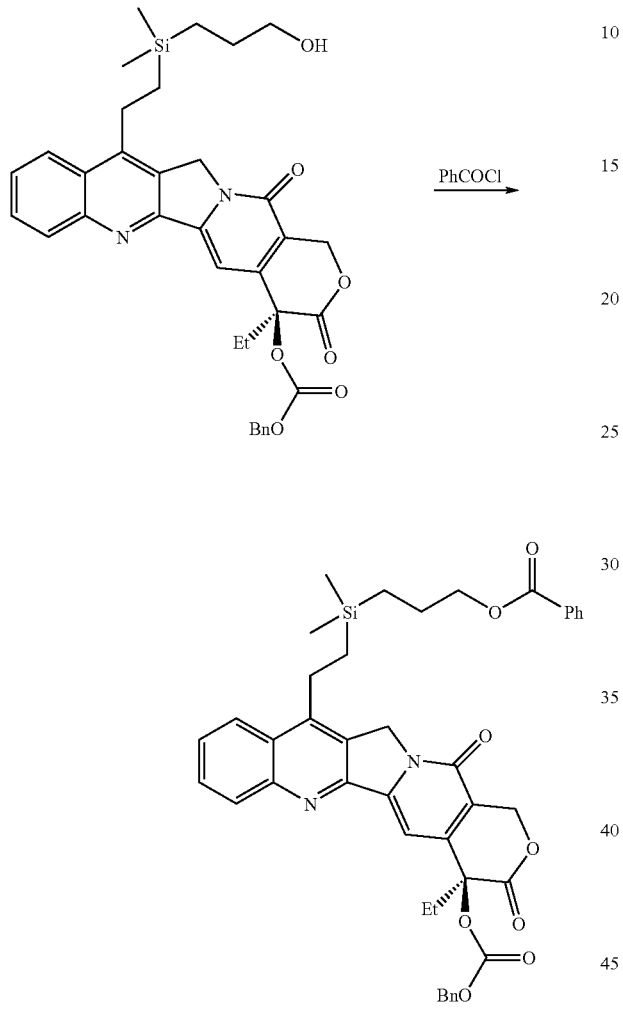

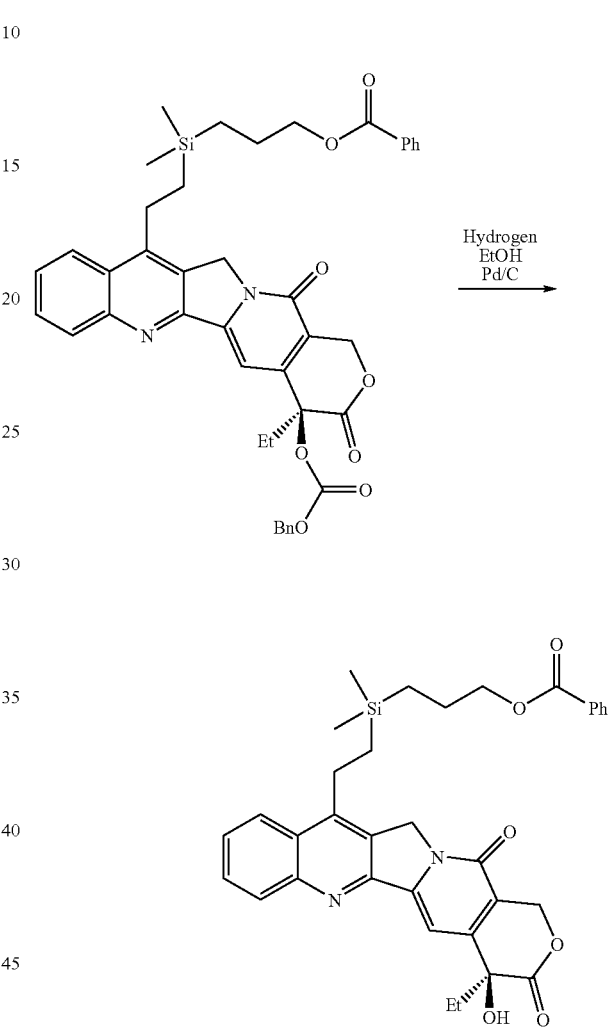

A mixture of Compound 53 (200 mg, 0.32 mmol), 4-dimethylaminopyridine (78 mg, 0.64 mmol), and benzoyl chloride (55 µL, 0.48 mmol) in 6.4 mL of dichloromethane was stirred at 21° C. for 5 hours. The reaction was quenched with saturated sodium bicarbonate solution, and aqueous layer was extracted with dichloromethane. The combined organic layers were dried over sodium sulfate and concentrated to afford a crude product, which was chromatographed to give the desired product.

$^1$H NMR (300 MHz, CDCl$_3$): δ 0.23 (s, 6H), 0.76 (m, 2H), 0.97 (m, 5H), 1.82 (m, 2H), 2.22 (m, 2H), 3.15 (m, 2H), 4.33 (t, J=6.9 Hz, 2H), 5.14 (m, 2H), 5.24 (s, 2H), 5.40 (d, J=17.1 Hz, 1H), 5.69 (d, J=17.1 Hz, 1H), 7.30 (m, 6H), 7.44 (t, J=7.8 Hz, 2H), 7.57 (m, 1H), 7.69 (t, J=6.0 Hz, 1H), 7.82 (t, J=8.4 Hz, 1H), 8.05 (d, J=7.8 Hz, 1H), 8.24 (d, J=8.4 Hz, 1H).

A mixture of Compound 53 (20 mg, 0.027 mmol), 10% palladium on carbon (4 mg, 20%) in 1 mL of ethanol was hydrogenated for 17 hours at a balloon pressure of hydrogen at 21° C. The catalyst was removed by filtration over celite and the filtrate was evaporated to give a crude product, which was chromatographed to give the desired product.

$^1$H NMR (300 MHz, CDCl$_3$): δ 0.23 (s, 6H), 0.76 (m, 2H), 0.97 (m, 2H), 1.82 (m, 2H), 1.05 (t, 3H), 1.88 (m, 4H), 3.14 (m, 2H), 4.33 (t, J=6.9 Hz, 2H), 5.25 (s, 2H), 5.31 (d, J=16.5 Hz, 1H), 5.76 (d, J=16.5 Hz, 1H), 7.43 (t, J=7.5 Hz, 2H), 7.57 (m, 1H), 7.66 (m, 2H), 7.82 (t, J=8.4 Hz, 1H), 8.05 (m, 3H), 8.24 (d, J=8.4 Hz, 1H).

60. Synthesis of Furan-2-carboxylic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 56)

61. Synthesis of Furan-2-carboxylic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 57)

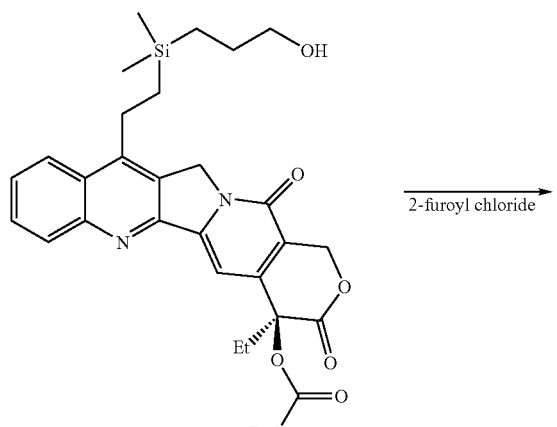

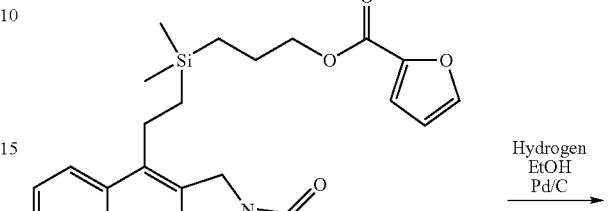

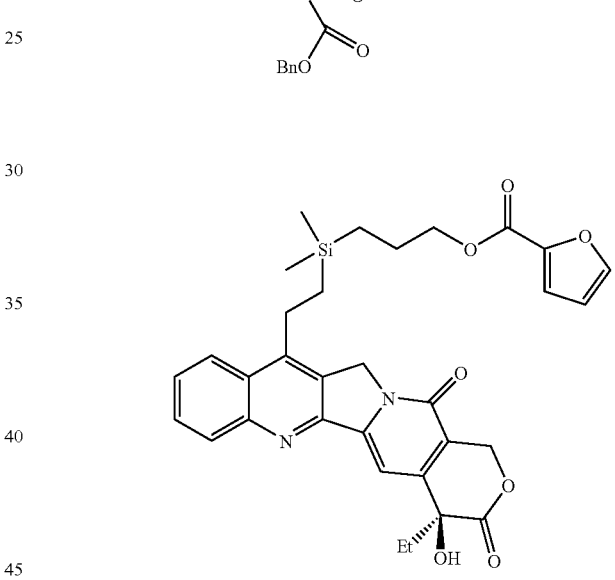

A mixture of Compound 53 (162 mg, 0.26 mmol), 4-dimethylaminopyridine (63 mg, 0.52 mmol), and 2-furoyl chloride (62 mg, 0.47 mmol) in 6.0 mL of dichloromethane was stirred at 21° C. for 5 hours. The reaction was quenched with saturated sodium bicarbonate solution, and aqueous layer was extracted with dichloromethane. The combined organic layers were dried over sodium sulfate and concentrated to afford a crude product, which was chromatographed to give the desired product.

$^1$H NMR (300 MHz, CDCl$_3$): δ 0.22 (s, 6H), 0.76 (m, 2H), 0.97 (m, 5H), 1.82 (m, 2H), 2.22 (m, 2H), 3.15 (m, 2H), 4.32 (t, J=7.2 Hz, 2H), 5.14 (m, 2H), 5.24 (s, 2H), 5.40 (d, J=17.1 Hz, 1H), 5.71 (d, J=17.1 Hz, 1H), 6.50 (m, 1H), 7.20 (m, 1H), 7.30 (m, 6H), 7.58 (s 1H), 7.69 (t, J=6.0 Hz, 1H), 7.82 (t, J=8.4 Hz, 1H), 8.05 (d, J=7.8 Hz, 1H), 8.24 (d, J=8.4 Hz, 1H).

A mixture of Compound 56 (180 mg, 0.25 mmol), 10% palladium on carbon (36 mg, 20%) in 6 mL of ethanol was hydrogenated for 18 hours at a balloon pressure of hydrogen at 21° C. The catalyst was removed by filtration over celite and the filtrate was evaporated to give a crude product, which was chromatographed to give the desired product.

$^1$H NMR (300 MHz, CDCl$_3$): δ 0.21 (s, 6H), 0.73 (m, 2H), 0.97 (m, 2H), 1.04 (t, 3H), 1.88 (m, 4H), 3.15 (m, 2H), 3.71 (s, 2H), 4.31 (t, J=6.9 Hz, 2H), δ 5.25 (s, 2H), 5.32 (d, J=16.2 Hz, 1H), 5.76 (d, J=16.2 Hz, 1H), 6.50 (m, 1H), 7.20 (d, J=3.9 Hz, 1H), 7.57 (s 1H), 7.67 (m, 2H), 7.82 (t, J=7.2 Hz, 1H), 8.05 (d, J=7.8 Hz, 1H), 8.24 (d, J=7.5 Hz, 1H).

62. Synthesis of Thiophene-2-carboxylic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 58)

63. Synthesis of Acetic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 59)

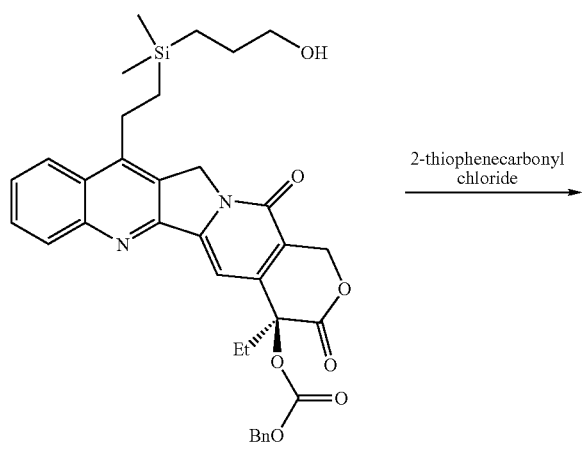

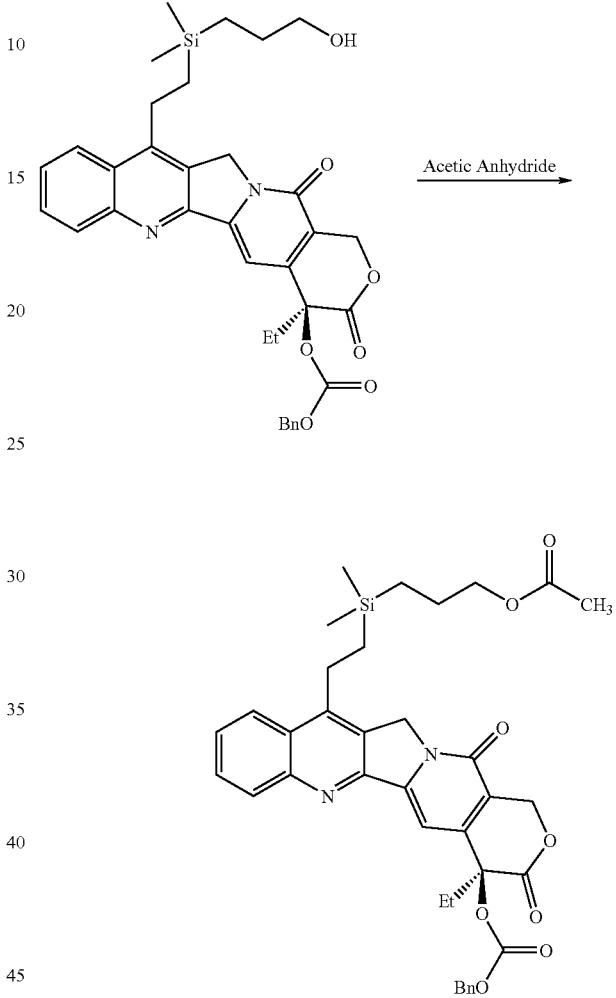

A mixture of Compound 53 (162 mg, 0.26 mmol), 4-dimethylaminopyridine (63 mg, 0.52 mmol), and 2-thiophenecarbonyl chloride (50 μL, 0.47 mmol) in 6.0 mL of dichloromethane was stirred at 21° C. for 5 hours. The reaction was quenched with saturated sodium bicarbonate solution, and aqueous layer was extracted with dichloromethane. The combined organic layers were dried over sodium sulfate and concentrated to afford a crude product, which was chromatographed to give the desired product.

$^1$H NMR (300 MHz, CDCl$_3$): δ 0.22 (s, 6H), 0.76 (m, 2H), 0.97 (m, 5H), 1.82 (m, 2H), 2.22 (m, 2H), 3.15 (m, 2H), 4.32 (t, J=6.9 Hz, 2H), 5.14 (m, 2H), 5.24 (s, 2H), 5.40 (d, J=16.2 Hz, 1H), 5.71 (d, J=16.2 Hz, 2H), 6.50 (m, 1H), 7.08 (m, 1H), 7.30 (m, 6H), 7.56 (m, 1H), 7.69 (t, J=6.0 Hz, 1H), 7.82 (m, 2H), 8.05 (d, J=7.8 Hz, 1H), 8.24 (d, J=8.4 Hz, 1H).

A mixture of Compound 53 (200 mg, 0.32 mmol), Pyridine (1.26 mL), and acetic anhydride (0.3 mL, 2.9 mmol) in 6.0 mL of dichloromethane was stirred at 21° C. for 5 hours. The reaction was quenched with saturated sodium bicarbonate solution, and aqueous layer was extracted with dichloromethane. The combined organic layers were dried over sodium sulfate and concentrated to afford a crude product, which was chromatographed to give the desired product.

$^1$H NMR (300 MHz, CDCl$_3$): δ 0.20 (s, 6H), 0.67 (m, 2H), 0.97 (m, 5H), 1.70 (m, 2H), 2.07 (s, 3H), 2.22 (m, 2H), 3.15 (m, 2H), 4.07 (t, J=6.9 Hz, 2H), 5.14 (m, 2H), 5.24 (s, 2H), 5.40 (d, J=17.1 Hz, 1H), 5.71 (d, J=17.1 Hz, 1H), 7.30 (m, 6H), 7.69 (t, J=6.0 Hz, 1H), 7.82 (m, 2H), 8.05 (d, J=7.8 Hz, 1H), 8.24 (d, J=8.4 Hz, 1H).

64. Synthesis of Acetic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 60)

65. Synthesis of Cyclobutanecarboxylic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 61)

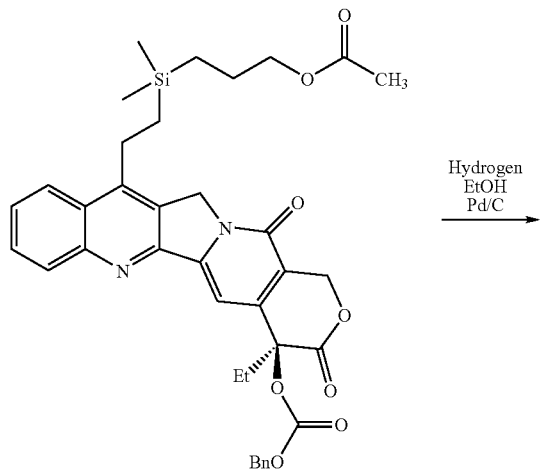

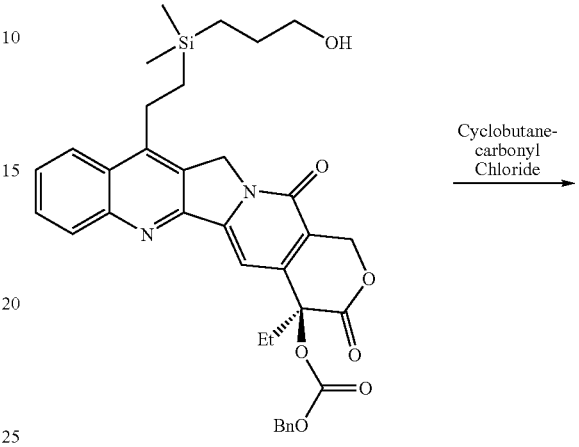

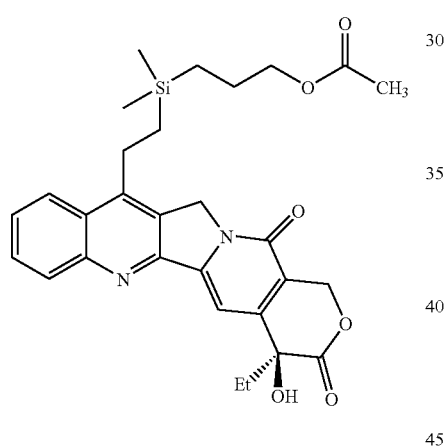

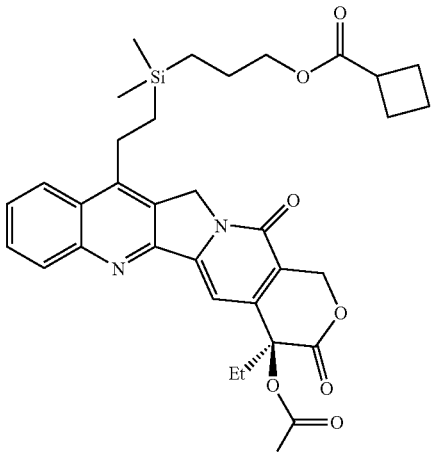

A mixture of Compound 59 (180 mg, 0.27 mmol), 10% palladium on carbon (36 mg, 20%) in 6 mL of ethanol was hydrogenated for 18 hours at a balloon pressure of hydrogen at 21° C. The catalyst was removed by filtration over celite and the filtrate was evaporated to give a crude product, which was chromatographed to give the desired product.

$^1$H NMR (300 MHz, CDCl$_3$): δ 0.20 (s, 6H), 0.67 (m, 2H), 0.97 (m, 2H), 1.04 (t, J=7.5 Hz, 3H), 1.67 (m, 2H), 1.90 (m, 2H), 2.07 (s, 3H), 3.11 (m, 2H), δ 3.71 (s, 1H), 4.07 (t, J=6.9 Hz, 2H), 5.25 (s, 2H), 5.32 (d, J=16.2 Hz, 1H), 5.76 (d, J=16.2 Hz, 1H), 7.67 (m, 2H),), 7.82 (t, J=7.2 Hz, 1H), 8.05 (d, J=7.8 Hz, 1H), 8.24 (d, J=7.5 Hz, 1H).

A mixture of Compound 53 (70 mg, 0.11 mmol), 4-dimethylaminopyridine (27 mg, 0.22 mmol), and cyclobutanecarbonyl chloride (26 mg, 0.22 mmol) in 2.0 mL of dichloromethane was stirred at 21° C. for 5 hours. The reaction was quenched with saturated sodium bicarbonate solution, and aqueous layer was extracted with dichloromethane. The combined organic layers were dried over sodium sulfate and concentrated to afford a crude product, which was chromatographed to give the desired product.

$^1$H NMR (300 MHz, CDCl$_3$): δ 0.20 (s, 6H), 0.67 (m, 2H), 0.97 (m, 5H), 1.70 (m, 3H), 1.93 (m, 2H), 2.25 (m, 6H), 3.12 (m, 2H), 4.07 (t, J=7.2 Hz, 2H), 5.14 (m, 2H), 5.24 (s, 2H), 5.40 (d, J=17.1 Hz, 1H), 5.71 (d, J=17.1 Hz, 1H), 7.30 (m, 6H), 7.69 (t, J=6.0 Hz, 1H), 7.82 (d, J=8.4 Hz, 1H), 8.05 (d, J=7.8 Hz, 1H), 8.24 (d, J=8.4 Hz, 1H).

66. Synthesis of Cyclobutanecarboxylic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 62)

67. Synthesis of Isoxazole-5-carboxylic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 63)

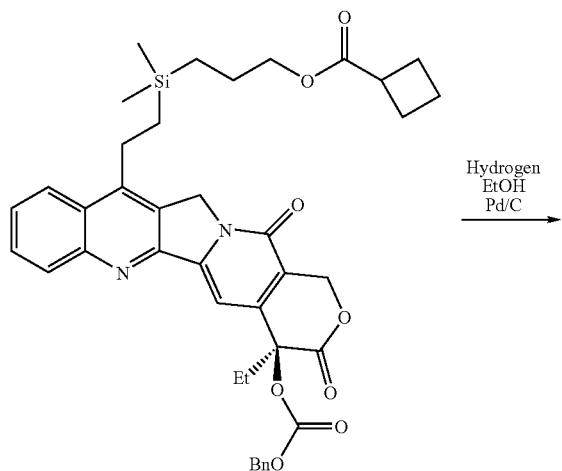
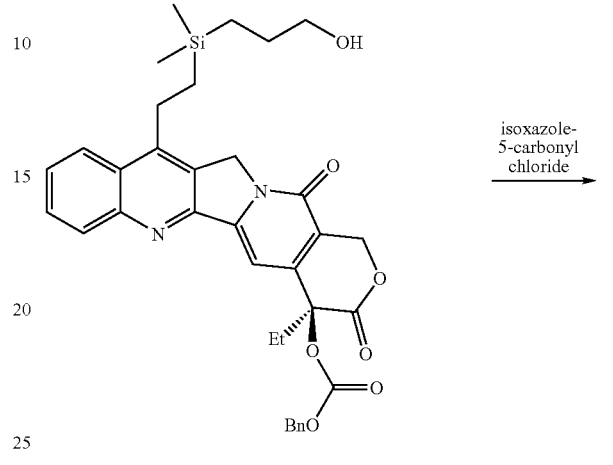
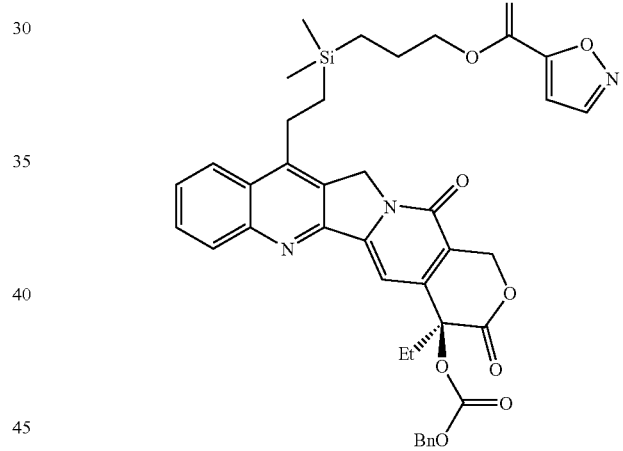

A mixture of Compound 61 (70 mg, 0.1 mmol), 10% palladium on carbon (20 mg, 20%) in 20 mL of ethanol was hydrogenated for 18 hours at a balloon pressure of hydrogen at 21° C. The catalyst was removed by filtration over celite and the filtrate was evaporated to give a crude product, which was chromatographed to give the desired product.

$^1$H NMR (300 MHz, CDCl$_3$): δ 0.20 (s, 6H), 0.67 (m, 2H), 0.97 (m, 2H), 1.05 (t, J=7.5 Hz, 3H), 1.67 (m, 3H), 1.90 (m, 4H), 2.21 (m, 4H), 3.11 (m, 2H), 3.70 (s, 1H), 4.07 (t, J=6.9 Hz, 2H), 5.25 (s, 2H), 5.32 (d, J=16.5 Hz, 1H), 5.76 (d, J=16.5 Hz, 1H), 7.67 (t, J=6.0 Hz, 1H), 7.82 (t, J=8.4 Hz, 1H), 8.05 (d, J=7.8 Hz, 1H), 8.24 (d, J=8.4 Hz, 1H).

A mixture of Compound 53 (70 mg, 0.11 mmol), 4-dimethylaminopyridine (30 mg, 0.25 mg), and isoxazole-5-carbonyl chloride (35 μL, 0.22 mmol) in 3.0 mL of dichloromethane was stirred at 21° C. for 5 hours. The reaction was quenched with saturated sodium bicarbonate solution, and aqueous layer was extracted with dichloromethane. The combined organic layers were dried over sodium sulfate and concentrated to afford a crude product, which was chromatographed to give the desired product.

$^1$H NMR (300 MHz, CDCl$_3$): δ 0.23 (s, 6H), 0.74 (m, 2H), 0.97 (m, 5H), 1.82 (m, 2H), 2.22 (m, 2H), 3.12 (m, 2H), 4.35 (t, J=6.9 Hz, 2H), 5.14 (m, 2H), 5.24 (s, 2H), 5.40 (d, J=17.4 Hz, 1H), 5.71 (d, J=17.4 Hz, 1H), 6.98 (d, J=1.8 Hz, 1H), 7.30 (m, 6H), 7.69 (t, J=6.0 Hz, 1H), 7.82 (t, J=8.4 Hz, 1H), 8.05 (d, J=7.8 Hz, 1H), 8.24 (d, J=8.4 Hz, 1H), 8.36 (d, J=1.8 Hz, 1H).

68. Synthesis of 2,3-Dihydro-isoxazole-5-carboxylic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester (Compound 64)

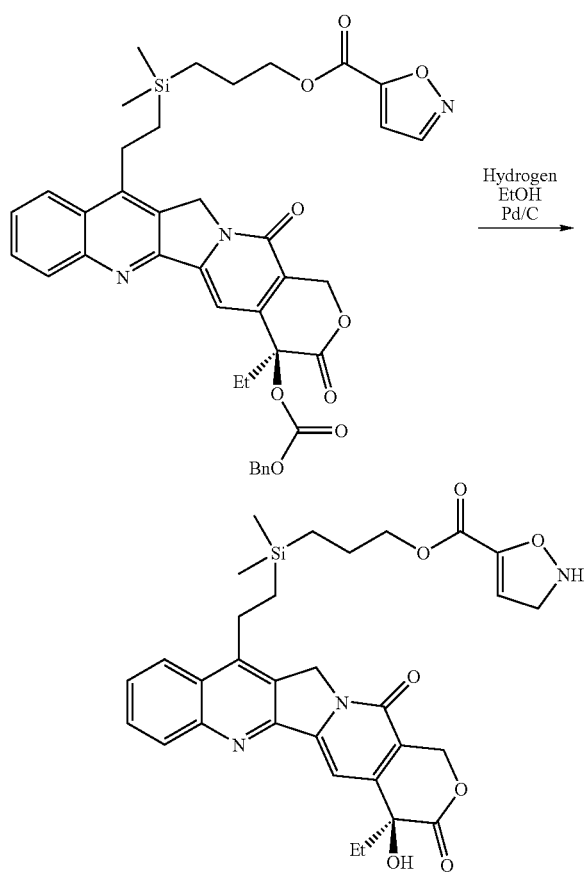

A mixture of Compound 63 (70 mg, 0.1 mmol), 10% palladium on carbon (20 mg, 20%) in 20 mL of ethanol was hydrogenated for 18 hours at a balloon pressure of hydrogen at 21° C. The catalyst was removed by filtration over celite and the filtrate was evaporated to give a crude product, which was chromatographed to give the desired product.

$^1$H NMR (300 MHz, CDCl$_3$): δ 0.20 (s, 6H), 0.71 (m, 2H), 0.97 (m, 2H), 1.04 (t, 3H), 1.88 (m, 4H), 3.15 (m, 2H), 3.70 (s, 1H), 4.24 (t, J=6.9 Hz, 2H), 5.25 (s, 2H), 5.32 (d, J=16.2 Hz, 1H), 5.65 (br, 1H), 5.76 (d, J=16.2 Hz, 1H), 5.93 (m, 1H), 7.16 (m, 2H), 7.67 (m, 2H), 7.82 (t, J=8.4 Hz, 1H), 8.05 (d, J=7.8 Hz, 1H), 8.24 (d, J=8.4 Hz, 1H). [M+H]$^+$: 590.7.

IV. Karenitecin® (BNP1350) Cytotoxicity Experiments in A2780/WT and DX5 Cells

Each of the testing conditions used in this study in both A2780/WT (wild-type) and A2780/DX5 cells were repeated in five to fifteen experiments that were performed on separate days. Each experiment consisted of one microtiter plate with at least eight individual assays of a given drug treatment condition on the plate. The sulforhodamine B (SRB) assay was used to assess cytotoxicity and absorbance at 570 nm ($A_{570}$) in order to calculate the percentage of cell control (or percent cell survival) for the various treatment conditions in the plate wells.

Reagents

Roswell Park Memorial Institute (RPMI 1640) medium, fetal bovine serum (FBS), and L-glutamine were purchased from Gibco BRL. Drugs were dissolved in sterile dimethylsulfoxide (DMSO), from American Type Culture Collection (ATCC) for stock solutions (2.5 to 5.0 mM). Subsequent dilutions were made using cell culture medium (prior to adding the drug to cells). SRB was purchased from Sigma and dissolved in 1.0 percent acetic acid. Trichloroacetic acid was purchased from VWR International.

Instrumentation

Cells were manipulated in a Class IIA/B3 Biological Safety Cabinet (Forma Scientific) and maintained at 37° C. in a humidified atmosphere containing 5% CO$_2$ in a water-jacketed cell culture incubator (Forma Scientific). Cells were counted using a Coulter-Z1 counter (Beckman-Coulter). Following drug treatment, plates were washed using a Biomek 2000 station (Beckman) and, following exposure to SRB dye, plates were washed using an automated plate washer (Model EL404, Bio-Tek Instruments). Percentage of control was correlated to $A_{570}$ values and determined using a Model EL800 plate reader (Bio-Tek Instruments).

Cell Growth and Viability

Population doubling times for the two cell lines used in this study encompassed a total of five cell doublings corresponding to approximately 5 days for A2780/WT and A2780/DX5 cells. A2780/WT and A2780/DX5 cells were cultured in RPMI 1640 medium supplemented with 10% fetal bovine serum and 1 mM of L-glutamine. Both cell lines were maintained as monolayered cultures in T-25 or T-75 flasks and then seeded to microtiter plate wells for experiments described herein. Prior to SRB assays, cell viability was monitored by evaluation of microtiter plate wells. Dead cells detach and float while living cells remain attached to the bottom of the cell well.

Cytotoxicity Assay (SRB Assay)

The sulforhodamine B (SRB) cytotoxicity assay (see, Skehan P, et al., New colorimetric cytotoxicity assay for anticancer-drug screening. *J. Natl. Cancer Inst.* 82:1107-1112 (1990)) was used to determine the cytotoxic effects of BNP1350, SN-38, topotecan, 9-NH$_2$-CPT, and 9-NO$_2$-CPT on cell growth in vitro. Briefly, after the medium was aspirated from individual plate wells, trichloroacetic acid (100 µL of 10.0% solution) was added to each well, and the plates were incubated at 4° C. for at least 1 hour. The plates were washed five-times with water using an automated microplate washer (Model EL 404, Bio-Tek Instruments), SRB solution (100 µL of 0.4 grams SRB dissolved in 100 mL 1.0 percent acetic acid) was added, and plates remained at room temperature for 15 minutes. The plates were then washed five-times using acetic acid (1.0%), air dried, and bound dye was solubilized in Tris base (150 µL, 10 mM). Plates were agitated (gently) for 5 minutes and the absorbance values of the SRB dye-protein adduct at a 570 nm wavelength ($A_{570}$) were determined using an automated microtiter plate reader equipped with an $A_{570}$ filter (Model EL800, BioTek Instruments).

TABLE VII

Summary of Cytotoxicity Experiments in A2780/WT and DX5 Cells

C7-Substituted Karenitecin® Analog

| Compound Number | $R_1$, $R_2$, or $R_3$ Group | A2780/ WT | A2780/ DX5 | IC50 Ratio |
|---|---|---|---|---|
| 1 | Vinyl | 13.0 | 21.8 | 1.68 |
| 3 | —$CH_2Cl$ | 10.0 | 14.5 | 1.45 |
| 4 | —$CH_2I$ | 15.7 | 27.0 | 1.72 |
| 6 | —$CH_2OAc$ | 9.3 | 21.1 | 2.27 |
| 7 | —$CH_2OH$ | 9.6 | 40.3 | 4.2 |
| 8 | —$CH_2$—S—CH$_2$—CH(NHBoc)(CO$_2$Me) | 39.8 | 110.4 | 2.77 |
| 9 | —$CH_2Sac$ | 64.7 | 125 | 1.94 |
| 10 | —$(CH_2)_3$—OH | 9.6 | 35.3 | 3.68 |
| 13 | —$(CH_2)_3$—$SO_2Ph$ | 8.5 | 53.5 | 6.3 |
| 14 | —$(CH_2)_3$—imidazolyl | 11.2 | 166.0 | 14.8 |
| 15 | —$(CH_2)_3$—triazolyl | 9.0 | 62.4 | 6.9 |
| 16 | —$(CH_2)_3$—$N(CH_3)_2$ | 23.6 | 511.9 | 21.7 |
| 17 | —$(CH_2)_3$—(2-pyridonyl) | 16.0 | 186.0 | 11.6 |
| 18 | —$(CH_2)_3$—$P(O)(OCH_3)_2$ | 58.6 | 686.6 / 16.4 | 11.7 |
| 23 | —$(CH_2)_3$—$NHCOCF_3$ | 16.9 | 55.8 | 3.3 |
| 25 | —$(CH_2)_3$—NH—C(O)—NHPh | 23.4 | 152.0 | 6.5 |
| 27 | —$(CH_2)_3$—NH—C(O)—$N(CH_2CH_3)_2$ | 65.2 | 470.2 | 7.21 |

TABLE VII-continued

Summary of Cytotoxicity Experiments in A2780/WT and DX5 Cells

C7-Substituted Karenitecin® Analog

| Compound Number | R₁, R₂, or R₃ Group | A2780/ WT | A2780/ DX5 | IC50 Ratio |
|---|---|---|---|---|
| 29 | —(CH₂)₃—NH—C(O)—N(CH₃)₂ | 27.5 | 312.3 | 11.4 |
| 30 | —CH₂—(1,2,4-triazol-1-yl) | 7.7 | 60.4 | 7.8 |
| 31 | —CH₂—(2-pyridon-1-yl) | 12.1 | 98.5 | 8.1 |
| 32 | —CH₂—(pyrrolidin-1-yl) | 46.4 | 319.3 | 6.9 |
| 33 | —CH₂—S—(1-methylimidazol-2-yl) | 9.7 | 57.8 | 6.0 |
| 34 | —CH₂—S—(4,5-dihydrothiazol-2-yl) | 20.3 | 55.5 | 2.7 |
| 35 | —CH₂—S—(CH₂)₂—OH | 8.2 | 21.6 | 2.6 |
| 37 | —CH₂—NH—SO₂—C₆H₄—Cl | 207.1 | 844.6 | 4.08 |
| 41 | —CH₂—NH—C(O)—NHPh | 23.2 | 259.2 | 11.2 |
| 43 | —CH₂—NH—C(O)—N(CH₂CH₃)₂ | 68.9 | 295.0 | 4.28 |

TABLE VII-continued

Summary of Cytotoxicity Experiments in A2780/WT and DX5 Cells

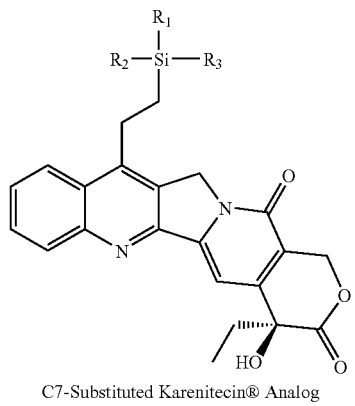

C7-Substituted Karenitecin® Analog

| Compound Number | $R_1$, $R_2$, or $R_3$ Group | A2780/ WT | A2780/ DX5 | IC50 Ratio |
|---|---|---|---|---|
| 45 | —CH$_2$—NH—C(O)—N(CH$_3$)$_2$ | 36.1 | 178.4 | 4.9 |
| 46 | —OH | 10.0 | 50.0 | 5.0 |
| 47 | —(CH$_2$)$_2$—CO$_2$H | 200.3 | 629.1 | 3.1 |
| 48 | —(CH$_2$)$_2$—CON(CH$_3$)$_2$ | 42.3 | 163.9 | 3.9 |
| 49 | NHCO(CH$_2$)$_2$— with BnO$_2$C and CO$_2$Bn | >2000 | >2000 | |
| 50 | NHCO(CH$_2$)$_2$— with HO$_2$C and CO$_2$H | 1699.3 | >2000 | 1699.3 |
| 55 | —(CH$_2$)$_3$—OBz | 24.0 | 111.5 | 4.6 |
| 57 | —(CH$_2$)$_3$—O—C(O)-furan | 12.3 | 29.2 | 2.4 |
| 60 | —(CH$_2$)$_3$—OAc | 10.6 | 32.1 | 3 |
| 62 | —(CH$_2$)$_3$—O—C(O)-cyclobutyl | 10.4 | 39.2 | 3.77 |
| 64 | —(CH$_2$)$_3$—O—C(O)-isoxazole | 14.0 | 59.8 | 4.27 |

It is generally held that an IC50 ratio of ≦2.0 indicates the potential for high toxicity against tumor cells.

V. Calculation of Free Camptothecin Analogs in Human Plasma

Stocks of various camptothecin analogs were prepared in DMSO. Phosphate buffer was prepared from analytical grade reagents and regenerated cellulose membranes with 12-14 kD molecular weight cut-off (MWCO) were purchased from Spectrum Laboratories. Samples were incubated 48 hours or longer at room temperature until equilibrium was reached. Experiments to determine the percent of free camptothecin/Karenitecin® analogs were performed in triplicate. Optimum HPLC detection conditions for each camptothecin/Karenitecin® analog were developed using traditional HPLC methods. The results are shown in Table VIII, below.

TABLE VIII

Percent of Free Camptothecin Analogs in Human Plasma (100 nM Compound Concentrations)

| Compound | Human Plasma |
|---|---|
| CPT | 0 |
| Topotecan | 100 |
| CPT-11 | 85 |
| SN-22 | 1 |
| SN-38 | 15 |
| Karenitecin (BNP1350) | 1.2 |
| Compound 1 (BNP10000) | 2 |
| Compound 3 (BNP10001) | 1 |
| Compound 6 (BNP10003) | 5 |
| Compound 10 (BNP10006) | 3.4 |
| Compound 30 (BNP10021) | 8 |

From Table VIII, above, it can be concluded that the novel C7-modified Karenitecin® analogs of the present invention possess lower affinity to human plasma proteins, in comparison to, e.g., SN22, camptothecin (CPT), and even Karenitecin®. Thus, the C7-modified Karenitecin® analogs improve plasma protein binding properties, while concomitantly maintaining the lactone stability and chemotherapeutic potency.

All patents, publications, scientific articles, web sites, and the like, as well as other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicant reserves the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicant reserves the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in the written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y". The letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicant reserves the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. An anti-cancer camptothecin analog selected from the group consisting of: 11-(4S)-[2-(dimethylvinylsilanyl)-ethyl]-4-ethyl-4-hydroxy-1,12-dihydro-4H-2-oxa-6,12a-diaza-dibenzo[b,h]fluorene-3,13-dione; 11-(4S)-[2-(dimethylvinylsilanyl)-ethyl]-4-ethyl-3,13-dioxo-3,4,12,13-tetrahydro-1H-2-oxa-6,12a-diaza-dibenzo[b,h]fluoren-4-yl ester; 11-(4S)-[2-(chloromethyldimethylsilanyl)-ethyl]-4-ethyl-4-hydroxy-1,12-dihydro-4H-2-oxa-6,12a-diaza-dibenzo[b,h]fluorene-3,13-dione; 11-(4S)-[2-(iodomethyldimethylsilanyl)-ethyl]-4-ethyl-4-hydroxy-1,12-dihydro-4H-2-oxa-6,12a-diaza-dibenzo[b,h]fluorene-3,13-dione; 11-(4S)-{2-[(benzylaminomethyl)-dimethylsilanyl]-ethyl}-4-ethyl-4-hydroxy-1,12-dihydro-4H-2-oxa-6,12a-diaza-dibenzo[b,h]fluorene-3,13-dione; Acetic acid-(4S)-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl ester; (4S)-4-ethyl-4-hydroxy-11-[2-(hydroxymethyldimethylsilanyl)-ethyl]-1,12-dihydro-4H-2-oxa-6,12a-diaza-dibenzo[b,h]fluorene-3,13-dione; (2R,4S)-2-tert-butoxycarbonylamino-3-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-methylsulfanyl)-propionic acid methyl ester; Thioacetic acid S-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)ester; 4S-4-ethyl-4-hydroxy-11-{2-[(3-hydroxypropyl)-dimethylsilanyl]-ethyl}-1,12-dihydro-4H-2-oxa-6,12a-diaza-dibenzo[b,h]fluorene-3,13-dione; (4S)-11-{2-[(3-bromopropyl)-dimethylsilanyl]-ethyl}-4-ethyl-4-hydroxy-1,12-dihydro-4H-2-oxa-6,12a-diaza-dibenzo[b,h]fluorene-3,13-dione; (4S)-11-{2-[(3-iodopropyl)-dimethylsilanyl]-ethyl}-4-ethyl-4-hydroxy-1,12-dihydro-4H-2-oxa-6,12a-diaza-dibenzo[b,h]fluorene-3,13-dione; (4S)-11-{2-[(3-benzenesulfonylpropyl)-dimethylsilanyl]-ethyl}-4-ethyl-4-hydroxy-1,12-dihydro-4H-2-oxa-6,12a-diaza-dibenzo[b,h]fluorene-3,13-dione; (4S)-4-ethyl-4-hydroxy-11-{2-[(3-imidazol-1-yl-propyl)-dimethyl-silanyl]-ethyl}-1,12-dihydro-4H-2-oxa-6,12a-diaza-dibenzo[b,h]fluorene-3,13-dione; (4S)-11-{2-[dimethyl-(3-[1,2,4]triazol-1-yl-propyl)-silanyl]-ethyl}-4-ethyl-4-hydroxy-1,12-dihydro-4H-2-oxa-6,12a-diaza-dibenzo[b,h]fluorene-3,13-dione; (4S)-11-{2-[(3-dimethylaminopropyl)-dimethylsilanyl]-ethyl}-4-ethyl-4-hydroxy-1,12-dihydro-4H-2-oxa-6,12a-diaza-dibenzo[b,h]fluorene-3,13-dione; (4S)-11-(2-{dimethyl-[3-(2-oxo-2H-pyridin-1-yl)-propyl]-silanyl}-ethyl)-4-ethyl-4-hydroxy-1,12-dihydro-4H-2-oxa-6,12a-diaza-dibenzo[b,h]fluorene-3,13-dione; (4S)-(3-{[2-(4-ethyl-4-hydroxy-1,12-hydroxy-3,13-dioxo-3,4,12,13-tetrahydro-1H-2-oxa-6,12a-diaza-dibenzo[b,h]fluoren-11-yl)-ethyl]-dimethylsilanyl}-propyl)-phosphonic acid dimethyl ester; (4S)-acetic acid 11-{2-[(3-bromopropyl)-dimethylsilanyl]-ethyl}-4-ethyl-3,13-dioxo-3,4,12,13-tetrahydro-1H-2-oxa-6,12a-diaza-dibenzo[b,h]fluoren-4-yl ester; (4S)-acetic acid 11-{2-[(3-azidopropyl)-dimethylsilanyl]-ethyl}-4-ethyl-3,13-dioxo-3,4,12,13-tetrahydro-1H-2-oxa-6,12a-diaza-dibenzo[b,h]fluoren-4-yl ester; Trifluoroacetate-(4S)-3-{[2-(4-acetoxy-4-ethyl-3,13-dioxo-3,4,12,13-tetrahydro-1H-2-oxa-6,12a-diaza-dibenzo[b,h]fluoren-11-yl)-ethyl]-dimethylsilanyl}-propylammonium; acetic acid (4S)-11-(2-{dimethyl-[3-(2,2,2-trifluoroacetylamino)-propyl]-silanyl}-ethyl)-4-ethyl-3,13-dioxo-3,4,12,13-tetrahydro-1H-2-oxa-6,12a-diaza-dibenzo[b,h]fluoren-4-yl ester; (4S)—N-(3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl)-2,2,2-trifluoro-acetamide; Acetic acid (4S)-11-(2-{dimethyl-[3-(3-phenylureido)-propyl]-silanyl}-ethyl)-4-ethyl-3,13-dioxo-3,4,12,13-tetrahydro-1H-2-oxa-6,12a-diaza-dibenzo[b,h]fluoren-4-yl ester; (4S)-1-(3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-propyl)-3-phenylurea; Acetic acid (4S)-11-(2-{[3-(3,3-diethylureido)-propyl]-dimethylsilanyl}-ethyl)-4-ethyl-3,13-dioxo-3,4,12,13-tetrahydro-1H-2-oxa-6,12a-diaza-dibenzo[b,h]fluoren-4-yl ester; (4S)-1,1-diethyl-3-(3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl)-urea; Acetic acid (4S)-11-(2-{[(3,3-dimethylureido)-propyl]-dimethylsilanyl}-ethyl)-4-ethyl-3,13-dioxo-3,4,12,13-tetrahydro-1H-2-oxa-6,12a-diaza-dibenzo[b,h]fluoren-4-yl ester; (4S)-3-(3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-propyl)-1,1-dimethylurea; (4S)-11-[2-(dimethyl-[1,2,4]triazol-1-ylmethylsilanyl)-ethyl]-4-ethyl-4-hydroxy-1,12-dihydro-4H-2-oxa-6,12a-diaza-dibenzo[b,h]fluorene-3,13-dione; (4S)-11-{2-[dimethyl-(2-oxo-2H-pyridin-1-ylmethyl)-silanyl]-ethyl}-4-ethyl-4-hydroxy-1,12-dihydro-4H-2-oxa-6,12a-diaza-dibenzo[b,h]fluorene-3,13-dione; (4S)-11-[2-(dimethyl-pyrrolidin-1-ylmethyl-silanyl)-ethyl]-4-ethyl-4-hydroxy-1,12-dihydro-4H-2-oxa-6,12a-diaza-dibenzo[b,h]fluorene-3,13-dione; (4S)-11-{2-[dimethyl-(1-methyl-1H-imidazol-2-ylsulfanylmethyl)-silanyl]-ethyl}-4-ethyl-4-hydroxy-1,12-dihydro-4H-2-oxa-6,12a-diaza-dibenzo[b,h]fluorene-3,13-dione; (4S)-11-{2-[(4,5-dihydro-thiazol-2-ylsulfanylmethyl)-dimethylsilanyl]-ethyl}-4-ethyl-4-hydroxy-1,12-dihydro-4H-2-oxa-6,12a-diaza-dibenzo[b,h]fluorene-3,13-dione; (4S)-4-ethyl-4-hydroxy-11-{2-[(2-hydroxy-ethylsulfanylmethyl)-dimethyl-silanyl]-ethyl}-1,12-dihydro-4H-2-oxa-6,12a-diaza-dibenzo[b,h]fluorene-3,13-dione; (4S)-11-[2-(azidomethyldimethylsilanyl)-ethyl]-4-ethyl-4-hydroxy-1,12-dihydro-4H-2-oxa-6,12a-diaza-dibenzo[b,h]fluorene-3,13-dione; (4S)-4-chloro-N-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)-benzenesulfonamide; Acetic acid (4S)-11-[2-(azidomethyldimethylsilanyl)-ethyl]-4-ethyl-3,13-dioxo-3,4,12,13-tetrahydro-1H-2-oxa-6,12a-diaza-dibenzo[b,h]fluoren-4-yl ester; trifluoroacetate; (4S)-{[2-(4-acetoxy-4-ethyl-3,13-dioxo-3,4,12,13-tetrahydro-1H-2-oxa-6,12a-diaza-dibenzo[b,h]fluoren-11-yl)-ethyl]-dimethylsilanyl}-methylammonium; Acetic acid (4S)-11-(2-{dimethyl-[(3-phenylureido)-methyl]-silanyl}-ethyl)-4-ethyl-3,13-dioxo-3,4,12,13-tetrahydro-1H-2-oxa-6,12a-diaza-dibenzo[b,h]fluoren-4-yl ester; (4S)-1-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)-3-phenylurea; acetic acid (4S)-11-{2-[(3,3-diethylureidomethyl)-dimethyl-silanyl]-ethyl}-4-ethyl-3,13-dioxo-3,4,12,13-tetrahydro-1H-2-oxa-6,12a-diaza-dibenzo[b,h]fluoren-4-yl ester; (4S)-1,1-diethyl-3-({[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethylsilanyl}-methyl)-urea; Acetic acid (4S)-11-{2-[(3,3-dimethylureidomethyl)-dimethylsilanyl]-ethyl}-4-ethyl-3,13-dioxo-3,4,12,13-tetrahydro-1H-2-oxa-6,12a-diaza-dibenzo[b,h]fluoren-4-yl ester; (4S)-3-({[2-(4-ethyl-4-hydroxy-3,4,12,13-tetrahydro-1H-2-oxa-6,12a-diazadibenzo[b,h]fluoren-11-yl)-ethyl]-dimethylsilanyl}-methyl)-1,1-dimethyl-urea; (4S)-4-Ethyl-4-hydroxy-11-[2-(hydroxydimethylsilanyl)-ethyl]-1,12-dihydro-4H-2-oxa-6,12a-diaza-dibenzo[b,h]fluorene-3,13-dione; 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propionic acid; 3-{[2-(4-Ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-N,N-dimethyl-propionamide; 2-(3-{[2-(4-Ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propionylamino)-pentanedioic acid dibenzyl ester; 2-(3-{[2-(4-Ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propionylamino)-pentanedioic acid; 11-{2-[Dimethyl-(3-triethylsilanyloxy-propyl)-silanyl]-ethyl}-4-ethyl-4-hydroxy-1,12-dihydro-4H-2-oxa-6,12a-diaza-dibenzo[b,h]fluorene-3,13-dione; Carbonic acid benzyl ester 11-{2-[dimethyl-(3-triethylsilanyloxy-propyl)-silanyl]-ethyl}-4-ethyl-3,13-dioxo-3,4,12,13-tetrahydro-1H-2-oxa-6,12a-diaza-dibenzo[b,h]fluoren-4-yl ester; Carbonic acid benzyl ester 4-ethyl-11-{2-[(3-hydroxy-propyl)-dimethyl-silanyl]-ethyl}-3,13-dioxo-3,4,12,13-tetrahydro-1H-2-oxa-6,12a-diaza-dibenzo[b,h]fluoren-4-yl ester; Benzoic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester; Benzoic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester; Furan-2-carboxylic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester; Furan-2-carboxylic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester; Thiophene-2-carboxylic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester; Acetic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester; Acetic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester; Cyclobutanecarboxylic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester; Cyclobutanecarboxylic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester; Isoxazole-5-carboxylic acid 3-{[2-(4-benzyloxycarbonyloxy-4-ethyl-3,13-dioxo-3,4,12,13-tetrahydro-1H-2-oxa-6,12a-diaza-dibenzo[b,h]fluoren-11-yl)-ethyl]-dimethyl-silanyl}-propyl ester; 2,3-Dihydro-isoxazole-5-carboxylic acid 3-{[2-(4-ethyl-4-hydroxy-3,13-dioxo-3,4,12,13-tetrahydro-1H-2-oxa-6,12a-diaza-dibenzo[b,h]fluoren-11-yl)-ethyl]-dimethyl-silanyl}-propyl ester, and pharmaceutically-acceptable salts thereof.

2. An anti-cancer camptothecin analog having the following structural formula:

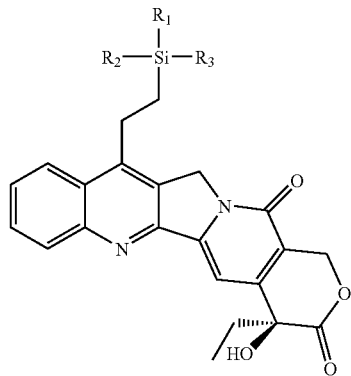

wherein $R_2$ is methyl; $R_3$ is methyl; and $R_1$ is selected from the group consisting of: Vinyl, Chloromethyl, Iodomethyl, Acetomethyl, Hydroxymethyl, Thioacetoxymethyl, Hydroxypropyl, 3-benzenesulfonylpropyl, 3-imidazol-1-yl-propyl, 3-[1,2,4]triazol-1-yl-propyl' 3-dimethylaminopropyl, 3-(2-oxo-2H-pyridin-1-yl)-propyl, the phosphoric acid derivative ($—(CH_2)_3—P(O)(OCH_3)_2$), Propyl trifluoroacetamide, 3-phenylurea, 3,3-diethylurea, 3,3-dimethylurea, [1,2,4]triazol-1-ylmethyl, 2-oxo-2H-pyridin-1-ylmethyl, pyrrolidin-1-ylmethyl, 1-methyl-1H-imidazol-2-ylsulfanylmethyl, 2-[4,5-dihydro-thiazol-2-ylsulfanylmethyl, 2-hydroxyethylsulfanylmethyl, 4-chlorobenzenesulfonamidomethyl, 3-phenylurea, 3,3-diethylurea, 3,3-dimethylurea, hydroxy, and pharmaceutically-acceptable salts thereof.

3. An anti-cancer camptothecin analog having the following structural formula:

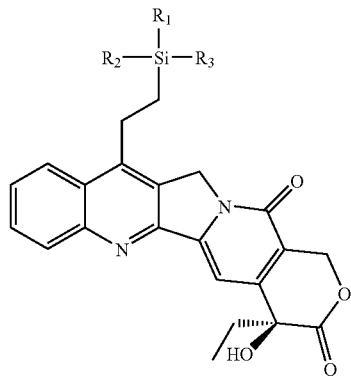

wherein $R_1$ is methyl; $R_3$ is methyl; and $R_2$ is selected from the group consisting of: Propionic acid, N,N-dimethylpropiomide, the

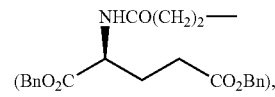

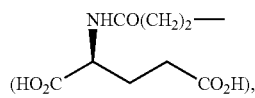

and pharmaceutically-acceptable salts thereof.

4. An anti-cancer camptothecin analog having the following structural formula:

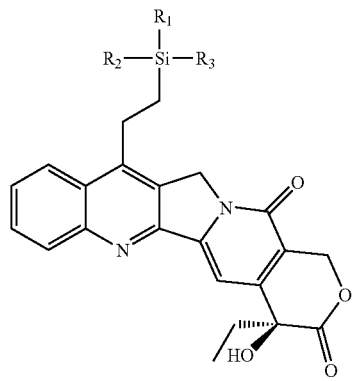

wherein $R_1$ is methyl; $R_2$ is methyl; and $R_3$ is selected from the group consisting of: the

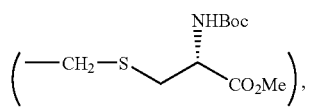

Propyl benzoate, 2-furoyloxypropyl, Acetoxypropyl, cyclobutanecarbonyloxypropyl, 5-oxazolecarbonyloxypropyl, and pharmaceutically-acceptable salts thereof.

5. The anti-cancer camptothecin analog of any one of claims 1-4, wherein the silicon is substituted with germanium.

6. A composition comprising a pharmaceutically-effective amount of an anti-cancer camptothecin analog of any one of claims 1-5 admixed with one or more pharmaceutically-acceptable carrier.

* * * * *